US006280974B1

(12) United States Patent
Miller et al.

(10) Patent No.: US 6,280,974 B1
(45) Date of Patent: Aug. 28, 2001

(54) RECOMBINANT FELINE CORONAVIRUS S PROTEINS

(75) Inventors: Timothy J. Miller, Malvern; Albert Paul Reed, Exton; Sharon R. Klepfer, Clifton Heights, all of PA (US); Nancy E. Pfeiffer, Seward; Brian T. Suiter, Lincoln, both of NE (US); Elaine V. Jones, Greenhill Farms, PA (US)

(73) Assignee: Pfizer Inc, New York, NY (US)

(*) Notice: Subject to any disclaimer, the term of this patent is extended or adjusted under 35 U.S.C. 154(b) by 0 days.

(21) Appl. No.: 08/392,459

(22) Filed: Feb. 22, 1995

Related U.S. Application Data

(63) Continuation of application No. 07/847,018, filed as application No. PCT/US91/08525 on Nov. 14, 1991, now abandoned, which is a continuation-in-part of application No. 07/698,927, filed on May 13, 1991, now abandoned, which is a continuation-in-part of application No. 07/613,066, filed on Nov. 14, 1990, now abandoned.

(51) Int. Cl.[7] .............................. A61K 39/29; C12Q 1/70

(52) U.S. Cl. ............................ 435/69.3; 435/5; 435/69.1; 435/91.1; 435/91.32; 435/320.1; 424/184.1; 424/186.1; 424/192.1; 424/196.11; 424/221.1; 536/23.1; 536/23.72; 536/24.1

(58) Field of Search .............................. 424/184.1, 186.1, 424/192.1, 196.11, 204.1, 221.1; 435/69.1, 69.3, 91.1, 91.32, 320.1, 5; 536/23.1, 23.72, 24.1

(56) References Cited

U.S. PATENT DOCUMENTS

| | | | | |
|---|---|---|---|---|
| 4,195,130 | | 3/1980 | Hoshino et al. | 435/235 |
| 4,293,653 | | 10/1981 | Horzinek et al. | 435/237 |
| 4,303,644 | * | 12/1981 | Davis | 424/89 |
| 4,358,535 | * | 11/1982 | Falkow et al. | 435/5 |
| 4,571,386 | | 2/1986 | Fishman et al. | 435/235 |
| 4,851,341 | * | 7/1989 | Hopp et al. | 435/68 |

FOREIGN PATENT DOCUMENTS

| | | | | |
|---|---|---|---|---|
| 0011864 | | 6/1980 | (EP) . | |
| 0011865 | | 6/1980 | (EP) . | |
| 0138242 | | 4/1985 | (EP) . | |
| 0 264 979 | * | 4/1988 | (EP) | C12N/15/00 |
| 0278541 | | 8/1988 | (EP) . | |
| 0310362 | | 4/1989 | (EP) . | |
| 0376744 | | 7/1990 | (EP) . | |
| 0411684 | | 2/1991 | (EP) . | |
| 8704624 | | 8/1987 | (WO) . | |
| 9013573 | | 11/1990 | (WO) . | |

OTHER PUBLICATIONS de Groot et al. J. Gen. Virol. 68: 2639–2646, 1987.*

De Groot et al. 1989 Virology vol. 171 pp. 493–502: Stably Expressed FIPV Peplomer Protein Induces Cell Fusion and Elicits Neutralizing Antibodies in Mice.*

Vennema et al., "Early Death after Feline Infectious Peritonits Virus Challenge due to Recombinant Vaccinia Virus Immunization", J. Virol. 64, 1407–1409 (1990).*

Lerner et al., in *Biology of Immunologic Disease*, F. J. Dixon et al., eds., HP Publishing Co., New York, pp. 331–338 (1983).*

Greene et al. "Subcloning", Meth. Enzymol. 152, 512–522 (1987).*

Christianson et al., "Characterization of a temperature sensitive feline infectious peritonitis coronavirus", Arch. Virol. 109, 185–196 (1989).*

Lutz, H., et al., 1986, Feline infectious peritonitis (FIP)—the present state of knowledge, J. Small Anim. Pract. 27: 108–116.

Pedersen, N.C., 1987, Virologic and immunologic aspects of feline infectious peritonitis virus infection, Adv. Exp. Med. Biol. 218:529–550.

Woods, R.D., and Pedersen, N.C., 1979, Cross–protection studies between feline infectious peritonitis and porcine transmissible gastroenteritis viruses, Vet. Microbiol. 4: 11–16.

Barlough, J.E., et al., 1985, Experimental inoculation of cats with human coronavirus 229E and subsequent challenge with feline infectious peritonitis virus, Can. J. Comp. Med. 49: 303–307.

Barlough, J.E., et al., 1984, Experimental inoculation of cats with canine coronavirus and subsequent challenge with feline infectious peritonitis virus, Lab. Anim. Sci. 34: 592–597.

Stoddart, C.A., et al., 1988, Attempted immunisation of cats against feline infectious peritonitis using canine coronavirus, Res. Vet. Sci. 45: 383–388.

Posthumus, W.P.A., et al., 1990, Analysis and simulation of a neutralizing epitope of transmissible gastroenteritis virus, J. Virol. 64: 3304–3309.

Pedersen, N.C., 1983, Attempted immunization of cats against feline infectious peritonitis using avirulent live virus or sublethal amounts of virulent virus, Am J. Vet. Res. 44: 229–234.

DeGroot, R.J., et al., 1987, cDNA cloning and sequence analysis of the gene encoding the peplomer protein of feline infectious peritonitis virus, J. Gen. Virol. 68: 2639–2646.

Gerber, J.D., et al., 1990, Protection against feline Infectious peritonitis by intranasal inoculation of a temperature–sensitive FIPV vaccine, Vaccine 8: 536–542.

(List continued on next page.)

*Primary Examiner*—Marianne P. Allen
*Assistant Examiner*—Mary K Zeman
(74) *Attorney, Agent, or Firm*—Peter C. Richardson; Paul H. Ginsburg; Alan L. Koller

(57) ABSTRACT

The present invention provides polynucleotide molecules encoding portions of the S protein from feline infectious peritonitis virus (FIPV). The present invention further provides polynucleotide molecules encoding the entire S protein or portions thereof from feline enteric coronavirus (FECV). The polynucleotide molecules of the present invention are useful as diagnostic reagents.

9 Claims, 49 Drawing Sheets

OTHER PUBLICATIONS

August, J.R., 1984, Feline infectious peritonitis, Sm. Anim. Pract. 14: 971–984.

Fiscus, S.A., et al., 1987, Antigenic comparison of feline coronavirus isolates: evidence for markedly different peplomer glycoproteins, J. Virol. 61: 2607–2613.

DeGroot, R.J., et al., 1988, Sequence analysis of the 3' end of the feline coronavirus FIPV 79–1146 genome: comparison with the genome of porcine coronavirus TGEV reveals large insertions, J. Virol. 167: 370–276.

Hohdatsu, T., et al., 1991, Antigenic analysis of feline coronaviruses with monoclonal antibodies (Mabs): preparation of Mabs which discriminate between FIPV strain 79–1146 and FECV strain 79–1683, Vet. Microbiol. 28: 13–24.

Fiscus, S.A., et al., 1987, Epitope–specific antibody responses to virulent and avirulent feline infectious peritonis virus isolates, J. Clin. Microbiol. 25: 1529–1534.

Bae, I., et al., 1991, Differentiation of transmissible gastroenteritis virus from porcine respiratory coronavirus and other antigenically related coronaviruses by using cDNA probes specific for the 5' region of the S glycoprotein gene, J. Clin. Microbiol. 29: 215–218.

Jacobs, L., et al., 1987, The nucleotide sequence of the peplomer gene of porcine transmissible gastroenteritis virus (TGEV): comparison with the sequence of the peplomer protein of feline infectious peritonitis virus (FIPV), Virus Res., 8: 363–371.

* cited by examiner

FIG. 3-1

AR58-3 PCR expression clone
SEQ ID NO: 19- nucleotide sequence
SEQ ID NO: 20- amino acid sequence

```
ATG GAT CCC GAA TTC CAA GAA AAA ACA CAA TCT CTG TTT 39
Met Asp Pro Glu Phe Gln Glu Lys Thr Gln Ser Leu Phe
  1             5                  10

GCC AAC GCA TTT GGC TAC CCT GCC ACT CAC ACC ATT CAG 78
Ala Asn Ala Phe Gly Tyr Pro Ala Thr His Thr Ile Gln
     15                  20                  25

GGC CCT GGC CGC GTG AAT TTG ATT GGT GAA CAC ACC GAC 117
Ala Pro Gly Arg Val Asn Leu Ile Gly Glu His Thr Asp
             30                  35

TAC AAC GAC GGT TTC GTT CTG CCC TGC GCG ATT GAT TAT 156
Tyr Asn Asp Gly Phe Val Leu Pro Cys Ala Ile Asp Tyr
40                   45                  50

                           Xma
CAA ACC GTG ATC CCT AAT ACC CGG GGC ACT GGT AAT GCA 195
Gln Thr Val Ile Pro Asn Thr Arg Gly Thr Gly Asn Ala
         55                  60      ↑           65
                               first FIPV aa

CGT GGT AAA CCA TTA TTA TTT CAT GTG CAT GGT GAG CCT 234
Arg Gly Lys Pro Leu Leu Phe His Val His Gly Glu Pro
                 70          75

GTT AGT GTT ATT ATA TAT ATA TCG GCT TAT AGG GAT GAT 273
Val Ser Val Ile Ile Tyr Ile Ser Ala Tyr Arg Asp Asp
     80                  85                  90
```

FIG. 3-2

```
GTG CAA CAA AGG CCC CTT TTA AAA CAT GGG TTA GTG TGT 312
Val Gln Gln Arg Pro Leu Leu Lys His Gly Leu Val Cys
             95                 100

ATA ACT AAA AAT CGC CAT ATT AAC TAT GAA CAA TTC GCC 351
Ile Thr Lys Asn Arg His Ile Ser Tyr Glu Gln Phe Ala
105                 110             115

TCC AAC CAG TGG AAT TCC ACA TGT ACG GGT GCT GAC AGA 390
Ser Asn Gln Trp Asn Ser Thr Cys Thr Gly Ala Asp Arg
        120                 125             130

AAA ATT CCC TTC TCT GTC ATA CCC ACG GAC AAT ACA GGA 429
Lys Ile Pro Phe Ser Val Ile Pro Thr Asp Asn Gly Thr
                135             140

AAA ATC TAT GGT CTT GAG TGG AAT GAT GAC TTT GTT ACA 486
Lys Ile Tyr Gly Leu Glu Trp Asn Asp Asp Phe Val Thr
    145                 150

GCT TAT ATT AGT GGT CGT TCT TAT CAC TTG AAC ATC AAT 507
Ala Tyr Ile Ser Gly Arg Ser Tyr His Leu Asn Ile Asn
            160                 165

ACT AAT TGG TTT AAC AAT GTC ACA CTT TTG TAT TCA CGC 546
Thr Asn Trp Phe Asn Asn Val Thr Leu Leu Tyr Ser Arg
170             175                     180

                            Stu I
AGC AGC ACT GCT ACC TGG GAG GCC TAG                 573
Ser Ser Thr Ala Thr Trp Glu Ala End
        185                 ↑
                            Last FIPV aa
```

FIG. 4-1

DF2 FIPV, nucleotides 1- 4365 [SEQ ID NO:21]
DF2 FIPV, arnino acid 1- 1454 [SEQ ID NO:22]

**DF2-HP, nucleotides* 1- 2246 [SEQ ID NO:23]**
**DF2-HP, amino acids* 1- 748 [SEQ ID NO:24]**

```
ATG ATT GTG CTC GTA ACT TGC CTC TTG TTG TTA TGT TCA TAC CAC ACA  48
Met Ile Val Leu Val Thr Cys Leu Leu Leu Leu Cys Ser Tyr His Thr
  1               5                  10                  15

GTT TTG AGT ACA ACA AAT AAT GAA TGC ATA CAA GTT AAC GTA ACA CAA  96
Val Leu Ser Thr Thr Asn Asn Glu Cys Ile Gln Val Asn Val Thr Gln
             20                  25                  30

TTG GCT GGC AAT GAA AAC CTT ATC AGA GAT TTT CTG TTT AGT AAC TTT 144
Leu Ala Gly Asn Glu Asn Leu Ile Arg Asp Phe Leu Phe Ser Asn Phe
         35                  40                  45

AAA GAA GAA GGA AGT GTA GTT GTT GGT GGT TAT TAC CCT ACA GAG GTG 192
Lys Glu Glu Gly Ser Val Val Val Gly Gly Tyr Tyr Pro Thr Glu Val
     50                  55                  60

                                T* G*
TGG TAC AAC TGC TCT AGA ACA GCA CAA ACT ACT GCC TTT CAG TAT TTT 240
Trp Tyr Asn Cys Ser Arg Thr Ala Gln Thr Thr Ala Phe Gln Tyr Phe
 65                  70             Arg*     75                  80

AAT AAT ATA CAT GCC TTT TAT TTT GTT ATG GAA GCC ATG GAA AAT AGC 288
Asn Asn Ile His Ala Phe Tyr Phe Val Met Glu Ala Met Glu Asn Ser
                 85                  90                  95
```

FIG. 4-2

```
ACT GGT AAT GCA CGT GGT AAA CCA TTA TTA TTT CAT GTG CAT GGT GAG 336
Thr Gly Asn Ala Arg Gly Lys Pro Leu Leu Phe His Val His Gly Glu
 ↑          100                 105                 110
97 of WSU 1146
FIPV in 58-3;
AR58-3 amino acid #62

CCT GTT AGT GTT ATT ATA TAT ATA TCG GCT TAT AGG GAT GAT GTG CAA 384
Pro Val Ser Val Ile Ile Tyr Ile Ser Ala Tyr Arg Asp Asp Val Gln
        115                 120                 125

CAA AGG CCC CTT TTA AAA CAT GGG TTA GTG TGC ATA ACT AAA AAT CGC 432
Gln Arg Pro Leu Leu Lys His Gly Leu Val Cys Ile Thr Lys Asn Arg
    130             Glu*135                 140

CAT ATT AAC TAT GAA CAA TTC ACC TCC AAC CAG TGG AAT TCC ACA TGT 480
His Ile Asn Tyr Glu Gln Phe Thr Ser Asn Gln Trp Asn Ser Thr Cys
145                 150  ↑       ↑      155                 160
                    AR58-3       AR58-3
                 a.a. #116       a.a. #118

ACG GGT GCT GAC AGA AAA ATT CCT TTC TCT GTC ATA CCC ACG GAC AAT 528
Thr Gly Ala Asp Arg Lys Ile Pro Phe Ser Val Ile Pro Thr Asp Asn
                165                 170                 175

GGA ACA AAA ATC TAT GGT CTT GAG TGG AAT GAT GAC TTT GTT ACA GCT 576
Gly Thr Lys Ile Tyr Gly Leu Glu Trp Asn Asp Asp Phe Val Thr Ala
            180                 185                 190

TAT ATT AGT GGT CGT TCT TAT CAC TTG AAC ATC AAT ACT AAT TGG TTT 624
Tyr Ile Ser Gly Arg Ser Tyr His Leu Asn Ile Asn Thr Asn Trp Phe
        195              ↑  200                 205
                        AR58-3
                        a.a. #164
```

FIG. 4-3

```
AAC AAT GTC ACA CTT TTG TAT TCA CGC TCA AGC ACT GCT ACC TGG GAA 672
Asn Asn Val Thr Leu Leu Tyr Ser Arg Ser Ser Thr Ala Thr Trp Glu
    210                 215                 220

TAC AGT GCT GCA TAT GCT TAC CAA GGT GTT TCT AAC TTC ACT TAT TAC 720
Tyr Ser Ala Ala Tyr Ala Tyr Gln Gly Val Ser Asn Phe Thr Tyr Tyr
225                 230                 235                 240

AAG TTA AAT AAC ACC AAT GGT CTA AAA ACC TAT GAA TTA TGT GAA GAT 768
Lys Leu Asn Asn Thr Asn Gly Leu Lys Thr Tyr Glu Leu Cys Glu Asp
                245                 250                 255

TAT GAA CAT TGC ACT GGC TAT GCT ACC AAT GTA TTT GCT CCG ACA TCA 816
Tyr Glu His Cys Thr Gly Tyr Ala Thr Asn Val Phe Ala Pro Thr Ser
            260                 265                 270

                                         T*
GGT GGT TAC ATA CCT GAT GGA TTT AGT TTT AAC AAT TGG TTC TTG CTT 864
Gly Gly Tyr Ile Pro Asp Gly Phe Ser Phe Asn Asn Trp Phe Leu Leu
        275                 280                 285

ACA AAT AGT TCC ACT TTT GTT AGT GGC AGG TTT GTA ACA AAT CAA CCA 912
Thr Asn Ser Ser Thr Phe Val Ser Gly Arg Phe Val Thr Asn Gln Pro
    290                 295                 300

TTA TTG ATT AAT TGC TTG TGG CCA GTG CCC AGT TTT GGT GTA GCA GCA 960
Leu Leu Ile Asn Cys Leu Trp Pro Val Pro Ser Phe Gly Val Ala Ala
305                 310                 315                 320

CAA GAA TTT TGT TTT GAA GGT GCA CAG TTT AGC CAA TGT AAT GGT GTG 1008
Gln Glu Phe Cys Phe Glu Gly Ala Gln Phe Ser Gln Cys Asn Gly Val
                325                 330                 335
```

FIG. 4-4

```
TCT TTA AAT AAC ACA GTG GAT GTT ATT AGA TTC AAC CTT AAT TTC ACT 1056
Ser Leu Asn Asn Thr Val Asp Val Ile Arg Phe Asn Leu Asn Phe Thr
            340                 345                 350

                                 C*
GCA GAT GTA CAA TCT GGT ATG GGT GCT ACA GTA TTT TCA CTG AAT ACA 1104
Ala Asp Val Gln Ser Gly Met Gly Ala Thr Val Phe Ser Leu Asn Thr
        355                 360                 365

ACA GGT GGT GTC ATT CTT GAA ATT TCA TGT TAT AGT GAC ACA GTG AGT 1152
Thr Gly Gly Val Ile Leu Glu Ile Ser Cys Tyr Ser Asp Thr Val Ser
    370                 375                 380

GAG TCT AGT TCT TAC AGT TAT GGT GAA ATC CCG TTC GGC ATA ACT GAC 1200
Glu Ser Ser Ser Tyr Ser Tyr Gly Glu Ile Pro Phe Gly Ile Thr Asp
385                 390                 395                 400

GGA CCA CGA TAC TGT TAT GTA CTT TAC AAT GGC ACA GCT CTT AAA TAT 1248
Gly Pro Arg Tyr Cys Tyr Val Leu Tyr Asn Gly Thr Ala Leu Lys Tyr
                405                 410                 415

TTA GGA ACA TTA CCA CCC AGT GTA AAG GAA ATT GCT ATT AGT AAG TGG 1296
Leu Gly Thr Leu Pro Pro Ser Val Lys Glu Ile Ala Ile Ser Lys Trp
            420                 425                 430
```

FIG. 4-5

```
GGC CAT TTT TAT ATT AAT GGT TAC AAT TTC TTT AGC ACA TTT CCT ATT 1344
Gly His Phe Tyr Ile Asn Gly Tyr Asn Phe Phe Ser Thr Phe Pro Ile
        435                 440                 445

                                        T*
GGT TGT ATA TCT TTT AAT TTA ACC ACT GGT GCT AGT GGA GCT TTT TGG 1392
Gly Cys Ile Ser Phe Asn Leu Thr Thr Gly Ala Ser Gly Ala Phe Trp
    450                 455                 Val* 460

ACA ATT GCT TAC ACA TCG TAT ACT GAA GCA TTA GTA CAA GTT GAA AAC 1440
Thr Ile Ala Tyr Thr Ser Tyr Thr Glu Ala Leu Val Gln Val Glu Asn
465                 470                 475                 480

ACA GCT ATT AAA AAT GTG ACG TAT TGT AAC AGT CAC ATT AAT AAC ATT 1488
Thr Ala Ile Lys Asn Val Thr Tyr Cys Asn Ser His Ile Asn Asn Ile
                485                 490                 495

AAA TGT TCT CAA CTT ACT GCT AAT TTG AAT AAT GGA TTT TAT CCT GTT 1536
Lys Cys Ser Gln Leu Thr Ala Asn Leu Asn Asn Gly Phe Tyr Pro Val
            500                 505                 510

GCT TCA AGT GAA GTA GGT TTC GTT AAT AAG AGT GTT GTG TTA TTA CCT 1584
Ala Ser Ser Glu Val Gly Phe Val Asn Lys Ser Val Val Leu Leu Pro
        515                 520                 525

                T*
AGC TTT TTC ACA CAC ACC GCT GTC AAT ATA ACC ATT GAT CTT GGT ATG 1632
Ser Phe Phe Thr His Thr Ala Val Asn Ile Thr Ile Asp Leu Gly Met
    530         Tyr*    535                 540
```

FIG. 4-6

```
AAG CTT AGT GGT TAT GGT CAA CCC ATA GCC TCG ACA CTA AGT AAC ATC 1680
Lys Leu Ser Gly Tyr Gly Gln Pro Ile Ala Ser Thr Leu Ser Asn Ile
545                 550                 555                 560

ACA CTA CCA ATG CAG GAT AAC AAT ACT GAT GTG TAC TGT ATT CGT TCT 1728
Thr Leu Pro Met Gln Asp Asn Asn Thr Asp Val Tyr Cys Ile Arg Ser
                565                 570                 575

                            A*
AAC CAA TTC TCA GTT TAT GTT CCT TCC ACT TGC AAA AGT TCT TTA TGG 1776
Asn Gln Phe Ser Val Tyr Val Pro Ser Thr Cys Lys Ser Ser Leu Trp
            530                 His 585                 590

        C*
GAC AAT ATT TTT AAT CAA GAC TGC ACG GAT GTT TTA GAG GCT ACA GCT 1824
Asp Asn Ile Phe Asn Gln Asp Cys Thr Asp Val Leu Glu Ala Thr Ala
        595                 600                 605

GTT ATA AAA ACT GGT ACT TGT CCT TTC TCA TTT GAT AAA TTG AAC AAT 1872
Val Ile Lys Thr Gly Thr Cys Pro Phe Ser Phe Asp Lys Leu Asn Asn
    610                 615                 620

TAC TTG ACT TTT AAC AAG TTC TGT TTG TCG TTG AGT CCT GTT GGT GCT 1920
Tyr Leu Thr Phe Asn Lys Phe Cys Leu Ser Leu Ser Pro Val Gly Ala
625                 630                 635                 640

AAT TGC AAG TTT GAT GTT GCT GCA CGT ACA AGA ACC AAT GAG CAG GTT 1968
Asn Cys Lys Phe Asp Val Ala Ala Arg Thr Arg Thr Asn Glu Gln Val
                645                 650                 655

GTT AGA AGT CTA TAT GTA ATA TAT GAA GAA GGA GAC AAC ATA GTG GGT 2016
Val Arg Ser Leu Tyr Val Ile Tyr Glu Glu Gly Asp Asn Ile Val Gly
            660                 665                 670
```

FIG. 4-7

```
                G*
GTA CCG TCT GAT AAT AGC GGT CTG CAC GAT TTG TCT GTG CTA CAC CTA 2064
Val Pro Ser Asp Asn Ser Gly Leu His Asp Leu Ser Val Leu His Leu
        675     Asp         680                 685

GAC TCC TGT ACA GAT TAC AAT ATA TAT GGT AGA ACT GGT GTT GGT ATT 2112
Asp Ser Cys Thr Asp Tyr Asn Ile Tyr Gly Arg Thr Gly Val Gly Ile
    690                 695                 700

ATT AGA CGA ACT AAC AGT ACG CTA CTT AGT GGC TTA TAT TAC ACA TCA 2160
Ile Arg Arg Thr Asn Ser Thr Leu Leu Ser Gly Leu Tyr Tyr Thr Ser
705                 710                 715                 720

CTA TCA GGT GAT TTG TTA GGC TTT AAA AAT GTT AGT GAT GGT GTC ATT 2208
Leu Ser Gly Asp Leu Leu Gly Phe Lys Asn Val Ser Asp Gly Val Ile
                725                 730                 735

TAT TCT GTG ACG CCA TGT GAT GTA AGC GCA CAA GCG GCT GTT ATT GAT 2256
Tyr Ser Val Thr Pro Cys Asp Val Ser Ala Gln Ala Ala Val Ile Asp
            740                 745                 750

GGT GCC ATA GTT GGA GCT ATG ACT TCC ATT AAC AGT GAA CTG TTA GGT 2304
Gly Ala Ile Val Gly Ala Met Thr Ser Ile Asn Ser Glu Leu Leu Gly
        755                 760                 765

CTA ACA CAT TGG ACA ACG ACA CCT AAT TT~ TAT TAC TAC TCT ATA TAT 2352
Leu Thr His Trp Thr Thr Thr Pro Asn Ph~ Tyr Tyr Tyr Ser Ile Tyr
    770                 775                 780

AAT TAC ACA AGT GAG AGG ACT CGT GGC ACt GCA ATT GAC AGT AAC GAT 2400
Asn Tyr Thr Ser Glu Arg Thr Arg Gly Tht Ala Ile Asp Ser Asn Asp
785                 790                 795                 800
```

FIG. 4-8

```
GTT GAT TGT GAA CCT GTC ATA ACC TAT TCT AAT ATA GGT GTT TGT AAA 2448
Val Asp Cys Glu Pro Val Ile Thr Tyr Ser Asn Ile Gly Val Cys Lys
                805                 810                 815

AAT GGT GCT TTG GTT TTT ATT AAC GTC ACA CAT TCT GAC GGA GAC GTG 2496
Asn Gly Ala Leu Val Phe Ile Asn Val Thr His Ser Asp Gly Asp Val
            820                 825                 830

CAA CCA ATT AGC ACT GGT AAT GTC ACG ATA CCT ACA AAT TTT ACC ATA 2544
Gln Pro Ile Ser Thr Gly Asn Val Thr Ile Pro Thr Asn Phe Thr Ile
        835                 840                 845

TCT GTG CAA GTT GAA TAC ATG CAG GTT TAC ACT ACA CCA GTA TCA ATA 2592
Ser Val Gln Val Glu Tyr Met Gln Val Tyr Thr Thr Pro Val Ser Ile
    850                 855                 860

GAT TGT GCA AGA TAC GTT TGT AAT GGT AAC CCT AGA TGT AAC AAA TTG 2640
Asp Cys Ala Arg Tyr Val Cys Asn Gly Asn Pro Arg Cys Asn Lys Leu
865                 870                 875                 880

TTA ACA CAA TAT GTG TCT GCA TGT CAA ACT ATT GAA CAA GCA CTT GCA 2688
Leu Thr Gln Tyr Val Ser Ala Cys Gln Thr Ile Glu Gln Ala Leu Ala
                885                 890                 895

ATG GGT GCC AGA CTT GAA AAC ATG GAG GTT GAT TCC ATG TTG TTT GTC 2736
Met Gly Ala Arg Leu Glu Asn Met Glu Val Asp Ser Met Leu Phe Val
            900                 905                 910
```

FIG. 4-9

```
TCG GAA AAT GCC CTT AAA TTG GCA TCT GTT GAG GCG TTC AAT AGT ACA 2784
Ser Glu Asn Ala Leu Lys Leu Ala Ser Val Glu Ala Phe Asn Ser Thr
        915                 920                 925

GAA AAT TTA GAT CCT ATT TAC AAA GAA TGG CCT AGC ATA GGT GGT TCT 2832
Glu Asn Leu Asp Pro Ile Tyr Lys Glu Trp Pro Ser Ile Gly Gly Ser
    930                 935                 940

TGG CTA GGA GGT CTA AAA GAT ATA CTA CCG TCC CAT AAT AGC AAA CGT 2880
Trp Leu Gly Gly Leu Lys Asp Ile Leu Pro Ser His Asn Ser Lys Arg
945                 950                 955                 960

AAG TAT GGT TCT GCT ATA GAA GAT TTG CTT TTT GAT AAA GTT GTA ACA 2928
Lys Tyr Gly Ser Ala Ile Glu Asp Leu Leu Phe Asp Lys Val Val Thr
                965                 970                 975

TCT GGT TTA GGT ACA GTT GAT GAA GAT TAT AAA CGT TGT ACT GGT GGT 2976
Ser Gly Leu Gly Thr Val Asp Glu Asp Tyr Lys Arg Cys Thr Gly Gly
            980                 985                 990

TAC GAC ATA GCA GAC TTG GTG TGT GCT CAA TAT TAC AAT GGC ATC ATG 3024
Tyr Asp Ile Ala Asp Leu Val Cys Ala Gln Tyr Tyr Asn Gly Ile Met
        995                 1000                1005

GTT CTA CCA GGT GTA GCT AAT GCT GAC AAG ATG ACT ATG TAC ACA GCA 3072
Val Leu Pro Gly Val Ala Asn Ala Asp Lys Met Thr Met Tyr Thr Ala
    1010                1015                1020

TCA CTT GCA GGT GGT ATA ACA TTA GGT GCA CTT GGT GGT GGC GCC GTG 3120
Ser Leu Ala Gly Gly Ile Thr Leu Gly Ala Leu Gly Gly Gly Ala Val
1025                1030                1035                1040
```

FIG. 4-10

```
GCT ATA CCT TTT GCA GTA GCA GTA CAG GCT AGA CTT AAT TAT GTT GCT 3168
Ala Ile Pro Phe Ala Val Ala Val Gln Ala Arg Leu Asn Tyr Val Ala
                1045                1050                1055

CTA CAA ACT GAT GTA TTG AAT AAA AAC CAA CAG ATC CTG GCT AAT GCT 3216
Leu Gln Thr Asp Val Leu Asn Lys Asn Gln Gln Ile Leu Ala Asn Ala
            1060                1065                1070

TTC AAT CAA GCT ATT GGT AAC ATT ACA CAG GCT TTT GGT AAG GTT AAT 3264
Phe Asn Gln Ala Ile Gly Asn Ile Thr Gln Ala Phe Gly Lys Val Asn
        1075                1080                1085

GAT GCT ATA CAT CAA ACA TCA CAA GGT CTT GCC ACT GTT GCT AAA GCG 3312
Asp Ala Ile His Gln Thr Ser Gln Gly Leu Ala Thr Val Ala Lys Ala
    1090                1095                1100

TTG GCA AAA GTG CAA GAT GTT GTC AAC AcA CAA GGG CAA GCT TTA AGT 3360
Leu Ala Lys Val Gln Asp Val Val Asn Thr Gln Gly Gln Ala Leu Ser
1105                1110                1115                1120

CAC CTT ACA GTA CAA TTG CAA AAT AAT TTT CAA GCC ATT AGT AGT TCT 3408
His Leu Thr Val Gln Leu Gln Asn Asn Phe Gln Ala Ile Ser Ser Ser
                1125                1130                1135

ATT AGT GAT ATT TAT AAC AGG CTT GAC GAA CTG AGT GCT GAT GCA CAA 3456
Iie Ser Asp Ile Tyr Asn Arg Leu Asp Glu Leu Ser Ala Asp Ala Gln
            1140                1145                1150

GTT GAT AGG CTG ATT ACA GGT AGA CTT ACA GCA CTT AAT GCA TTT GTG 3504
Val Asp Arg Leu Ile Thr Gly Arg Leu Thr Ala Leu Asn Ala Phe Val
        1155                1160                1165
```

FIG. 4-11

```
TCT CAG ACT CTA ACC AGA CAA GCA GAG GTT AGG GCT AGT AGA CAA CTT 3552
Ser Gln Thr Leu Thr Arg Gln Ala Glu Val Arg Ala Ser Arg Gln Leu
    1170                1175                1180

GCC AAA GAC AAG GTT AAT GAA TGT GTT AGG TCT CAG TCT CAG AGA TTC 3600
Ala Lys Asp Lys Val Asn Glu Cys Val Arg Ser Gln Ser Gln Arg Phe
1185                1190                1195                1200

GGA TTC TGT GGT AAT GGT ACA CAT TTG TTT TCA CTA GCA AAT GCA GCA 3648
Gly Phe Cys Gly Asn Gly Thr His Leu Phe Ser Leu Ala Asn Ala Ala
                1205                1210                1215

CCA AAT GGC ATG ATT TTC TTT CAT ACA GTA CTA TTA CCA ACA GCT TAT 3696
Pro Asn Gly Met Ile Phe Phe His Thr Val Leu Leu Pro Thr Ala Tyr
            1220                1225                1230

GAA ACT GTA ACA GCT TGG TCA GGT ATT TGT GCT TCA GAT GGC GAT CGC 3744
Glu Thr Val Thr Ala Trp Ser Gly Ile Cys Ala Ser Asp Gly Asp Arg
        1235                1240                1245

ACT TTC GGA CTT GTC GTT AAA GAT GTG CAG TTG ACG TTG TTT CGT AAT 3792
Thr Phe Gly Leu Val Val Lys Asp Val Gln Leu Thr Leu Phe Arg Asn
    1250                1255                1260

CTA GAT GAC AAG TTC TAT TTG ACC CCC AGA ACT ATG TAT CAG CCT AGA 3840
Leu Asp Asp Lys Phe Tyr Leu Thr Pro Arg Thr Met Tyr Gln Pro Arg
1265                1270                1275                1280

GTT GCA ACT AGT TCT GAT TTT GTT CAA ATT GAA GGG TGT GAT GTG TTG 3888
Val Ala Thr Ser Ser Asp Phe Val Gln Ile Glu Gly Cys Asp Val Leu
                1285                1290                1295

TTT GTC AAC GCG ACT GTA ATT GAT TTG CCT AGT ATT ATA CCT GAC TAT 3936
Phe Val Asn Ala Thr Val Ile Asp Leu Pro Ser Ile Ile Pro Asp Tyr
            1300                1305                1310
```

FIG. 4-12

```
ATT GAC ATT AAT CAA ACT GTT CAA GAC ATA TTA GAA AAT TAC AGA CCA 3984
Ile Asp Ile Asn Gln Thr Val Gln Asp Ile Leu Glu Asn Tyr Arg Pro
        1315                1320                1325

AAC TGG ACT GTA CCT GAA TTT ACA CTT GAT ATT TTC AAC GCA ACC TAT 4032
Asn Trp Thr Val Pro Glu Phe Thr Leu Asp Ile Phe Asn Ala Thr Tyr
    1330                1335                1340

TTA AAT CTG ACT GGT GAA ATT GAT GAC TTA GAG TTT AGG TCA GAA AAG 4080
Leu Asn Leu Thr Gly Glu Ile Asp Asp Leu Glu Phe Arg Ser Glu Lys
1345                1350                1355                1360

CTA CAT AAC ACT ACA GTA GAA CTT GCC ATT CTC ATT GAT ACC ATT AAT 4128
Leu His Asn Thr Thr Val Glu Leu Ala Ile Leu Ile Asp Thr Ile Asn
                1365                1370                1375

AAT ACA TTA GTC AAT CTT GAA TGG CTC AAT AGA ATT GAA ACT TAT GTA 4176
Asn Thr Leu Val Asr Leu Glu Trp Leu Asn Arg Ile Glu Thr Tyr Val
            13BO                  1385 1390

AAA TGG CCT TGG TAT GTG TGG CTA CTG ATA GGT CTA GTA GTA GTA TTT 4224
Lys Trp Pro Trp Tyr Val Trp Leu Leu Ile Gly Leu Val Val Val Phe
        1395                1400                1405

TGC ATA CCA TTA CTG CTA TTT TGC TGT TTT AGC ACA GGT TGT TGT GGA 4272
Cys Ile Pro Leu Leu Leu Phe Cys Cys Phe Ser Thr Gly Cys Cys Gly
    1410                1415                1420

TGC ATA GGT TGT TTA GGA AGT TGT TGT CAC TCT ATA TGT AGT AGA AGA 4320
Cys Ile Gly Cys Leu Gly Ser Cys Cys His Ser Ile Cys Ser Arg Arg
1425                1430                1435                1440

CAA TTT GAA TAT TAT GAA CCA ATT GAA AAA GTG CAT GTC CAC 4362
Gln Phe Glu Tyr Tyr Glu Pro Ile Glu Lys Val His Val His
                1445                1450

TAA                                                             4365
```

FIG. 5-1

```
TS FIPV, nucleotides 1- 4365 [SEQ ID NO: 25]
TS FIPV, amino acids 1- 1454 [SEQ ID NO: 26]
```

**TS-BP, nucleotides* 1- 2246 [SEQ ID NO:27]**
**TS-BP, amino acids* 1- 748 [SEQ ID NO:28]**

```
ATG ATT GTG CTC GTA ACT TGC CTC TTG TTG TTA TGT TCA TAC CAC ACA 48
Met Ile Val Leu Val Thr Cys Leu Leu Leu Leu Cys Ser Tyr His Thr
  1               5                  10                  15
                                                     A*
GTT TTG AGT ACA ACA AAT AAT GAA TGC ATA CAA GTT AAC GTT ACA CAA 96
Val Leu Ser Thr Thr Asn Asn Glu Cys Ile Gln Val Asn Val Thr Gln
             20                  25                  30

TTG GCT GGC AAT GAA AAC CTT ATC AGA GAT TTT CTG TTT AGT AAC TTT 144
Leu Ala Gly Asn Glu Asn Leu Ile Arg Asp Phe Leu Phe Ser Asn Phe
         35                  40                  45

AAA GAA GAA GGA AGT GTA GTT GTT GGT GGT TAT TAC CCT ACA GAG GTG 192
Lys Glu Glu Gly Ser Val Val Val Gly Gly Tyr Tyr Pro Thr Glu Val
     50                  55                  60

TGG TAC AAC TGC TCT AGA ACA GCT CGA ACT ACT GCC TTT CAG TAT TTT 240
Trp Tyr Asn Cys Ser Arg Thr Ala Arg Thr Thr Ala Phe Gln Tyr Phe
65                   70                  75                  80

AAT AAT ATA CAT GCC TTT TAT TTT GTT ATG GAA GCC ATG GAA AAT AGC 288
Asn Asn Ile His Ala Phe Tyr Phe Val Met Glu Ala Met Glu Asn Ser
                 85                  90                  95
```

FIG. 5-2

```
ACT GGT AAT GCA CGT GGT AAA CCA TTA TTA TTT CAT GTG CAT GGT GAG 336
Thr Gly Asn Ala Arg Gly Lys Pro Leu Leu Phe His Val His Gly Glu
 ↑           100                 105                 110
97 of WSU 1146
FIPV in 58-3
corresponds to amino acid #62 of AR58-3

CCT GTT AGT GTT ATT ATA TAT ATA TCG GCT TAT AGG GAT GAT GTG CAA 384
Pro Val Ser Val Ile Ile Tyr Ile Ser Ala Tyr Arg Asp Asp Val Gln
        115                 120                 125

CAA AGG CCC CTT TTA AAA CAT GGG TTA GTG TGC ATA ACT AAA AAT CGC 432
Gln Arg Pro Leu Leu Lys His Gly Leu Val Cys Ile Thr Lys Asn Arg
    130                 135                 140

CAT ATT AAC TAT GAA CAA TTC ACC TCC AAC CAG TGG AAT TCC ACA TGT 480
His Ile Asn Tyr Glu Gln Phe Thr Ser Asn Gln Trp Asn Ser Thr Cys
145                     150  ↑      ↑        155                 160
                      AR58-3      AR58-3
                   a.a. #116      a.a. #118

ACG GGT GCT GAC AGA AAA ATT CCT TTC TCT GTC ATA CCC ACG GAC AAT 528
Thr Gly Ala Asp Arg Lys Ile Pro Phe Ser Val Ile Pro Thr Asp Asn
                165                 170                 175

GGA ACA AAA ATC TAT GGT CTT GAG TGG AAT GAT GAC TTT GTT ACA GCT 576
Gly Thr Lys Ile Tyr Gly Leu Glu Trp Asn Asp Asp Phe Val Thr Ala
            180                 185                 190
```

FIG. 5-3

```
TAT ATT AGT GGT CGT TCT TAT CAC TTG AAC ATC AAT ACT AAT TGG TTT 624
Tyr Ile Ser Gly Ara Ser Tyr His Leu Asn Ile Asn Thr Asn Trp Phe
        195                 200                 205

AAC AAT GTC ACA CTT TTG TAT TCA CGC TCA AGC ACT GCT ACC TGG GAA 672
Asn Asn Val Thr Leu Leu Tyr Ser Ara Ser Ser Thr Ala Thr Trp Glu
    210                 215                 220                ↑

                                            FIPV amino acid
                                        #223 from WSU 1146;
                                          AR58-3 a.a. #189

TAC AGT GCT GCA TAT GCT TAC CAA GGT GTT TCT AAC TTC ACT TAT TAC 720
Tyr Ser Ala Ala Tyr Ala Tyr Gln Gly Val Ser Asn Phe Thr Tyr Tyr
225                 230                 235                 240

AAG TTA AAT AAC ACC AAT GGT CTA AAA ACC TAT GAA TTA TGT GAA GAT 768
Lys Leu Asn Asn Thr Asn Gly Leu Lys Thr Tyr Glu Leu Cys Glu Asp
                245                 250                 255

TAT GAA CAT TGC ACT GGC TAT GCT ACC AAT GTA TTT GCT CCG ACA TCA 816
Tyr Glu His Cys Thr Gly Tyr Ala Thr Asn Val Phe Ala Pro Thr Ser
            260                 265                 270

GGT GGT TAC ATA CCT GAT GGA TTT AGT TTT AAT AAT TGG TTC TTG CTT 864
Gly Gly Tyr Ile Pro Asp Gly Phe Ser Phe Asn Asn Trp Phe Leu Leu
        275                 280                 285

ACA AAT AGT TCC ACT TTT GTT AGT GGC AGG TTT GTA ACA AAT CAA CCA 912
Thr Asn Ser Ser Thr Phe Val Ser Gly Arg Phe Val Thr Asn Gln Pro
    290                 295                 300
```

FIG. 5-4

```
                                                            C*
TTA TTG ATT AAT TGC TTG TGG CCA GTG CCC AGT TTT GGT GTA GTA GCA  960
Leu Leu Ile Asn Cys Leu Trp Pro Val Pro Ser Phe Gly Val Val Ala
305                 310                 315                 Ala*320

CAA GAA TTT TGT TTT GAA GGT GCA CAG TTT AGC CAA TGT AAT GGT GTG 1008
Gln Glu Phe Cys Phe Glu Gly Ala Gln Phe Ser Gln Cys Asn Gly Val
                325                 330                 335

TCT TTA AAT AAC ACA GTG GAT GTT ATT AGA TTC AAC CTT AAT TTC ACT 1056
Ser Leu Asn Asn Thr Val Asp Val Ile Arg Phe Asn Leu Asn Phe Thr
            340                 345                 350

GCA GAT GTA CAA TCT GGT ATG GGT GCT ACA GTA TTT TCA CTG AAT ACA 1104
Ala Asp Val Gln Ser Gly Met Gly Ala Thr Val Phe Ser Leu Asn Thr
        355                 360                 365

ACA GGT GGT GTC ATT CTT GAA ATT TCA TGT TAT AGT GAC ACA GTG AGT 1152
Thr Gly Gly Val Ile Leu Glu Ile Ser Cys Tyr Ser Asp Thr Val Ser
    370                 375                 380

GAG TCT AGT TCT TAC AGT TAT GGT GAA ATC CCG TTC GGC ATA ACT GAC 1200
Glu Ser Ser Ser Tyr Ser Tyr Gly Glu Ile Pro Phe Gly Ile Thr Asp
385                 390                 395                 400

GGA CCA CGA TAC TGT TAT GTA CTT TAC AAT GGC ACA GCT CTT AAA TAT 1248
Gly Pro Arg Tyr Cys Tyr Val Leu Tyr Asn Gly Thr Ala Leu Lys Tyr
                405                 410                 415

TTA GGA ACA TTA CCA CCC AGT GTA AAG GAA ATT GCT ATT AGT AAG TGG 1296
Leu Gly Thr Leu Pro Pro Ser Val Lys Glu Ile Ala Ile Ser Lys Trp
            420                 425                 430
```

FIG. 5-5

```
GGC CAT TTT TAT ATT AAT GGT TAC AAT TTC TTT AGC ACA TTT CCT ATT 1344
Gly His Phe Tyr Ile Asn Gly Tyr Asn Phe Phe Ser Thr Phe Pro Ile
        435                 440                 445

GAT TGT ATA TCT TTT AAT TTA ACC ACT GGT GTT AGT GGA GCT TTT TGG 1392
Asp Cys Ile Ser Phe Asn Leu Thr Thr Gly Val Ser Gly Ala Phe Trp
    450                 455                 460

ACA ATT GCT TAC ACA TCG TAT ACT GAA GCA TTA GTA CAA GTT GAA AAC 1440
Thr Ile Ala Tyr Thr Ser Tyr Thr Glu Ala Leu Val Gln Val Glu Asn
465                 470                 475                 480

ACA GCT ATT AAA AAT GTG ACG TAT TGT AAC AGT CAC ATT AAT AAC ATT 1488
Thr Ala Ile Lys Asn Val Thr Tyr Cys Asn Ser His Ile Asn Asn Ile
                485                 490                 495

AAA TGT TCT CAA CTT ACT GCT AAT TTG AAT AAT GGA TTT TAT CCT GTT 1536
Lys Cys Ser Gln Leu Thr Ala Asn Leu Asn A9n Gly Phe Tyr Pro Val
            500                 505                 510

GCT TCA AGT GAA GTA GGT TTC GTT AAT AAG AGT GTT GTG TTA TTA CCT 1584
Ala Ser Ser Glu Val Gly Phe Val Asn Lys Ser Val Val Leu Leu Pro
        515                 520                 525

AGC TTT TTC ACA TAC ACC GCT GTC AAT ATA ACC ATT GAT CTT GGT ATG 1632
Ser Phe Phe Thr Tyr Thr Ala Val Asn Ile Thr Ile Asp Leu Gly Met
    530                 535                 540

AAG CTT AGT GGT TAT GGT CAA CCC ATA GCC TCG ACA CTA AGT AAC ATC 1680
Lys Leu Ser Gly Tyr Gly Gln Pro Ile Ala Ser Thr Leu Ser Asn Ile
545                 550                 555                 560
```

FIG. 5-6

```
ACA CTA CCA ATG CAG GAT AAC AAT ACT GAT GTG TAC TGT ATT CGT TCT 1728
Thr Leu Pro Met Gln Asp Asn Asn Thr Asp Val Tyr Cys Ile Arg Ser
                565                 570                 575

AAC CAA TTC TCA GTT TAT GTT CAT TCC ACT TGC AAA AGT TCT TTA TGG 1776
Asn Gln Phe Ser Val Tyr Val His Ser Thr Cys Lys Ser Ser Leu Trp
            580                 585                 590

GAC AAT ATT TTT AAT CAA GAC TGC ACG GAT GTT TTA GAG GCT ACA GCT 1824
Asp Asn Ile Phe Asn Gln Asp Cys Thr Asp Val Leu Glu Ala Thr Ala
        595                 600                 605

GTT ATA AAA ACT GGT ACT TGT CCT TTC TCA TTT GAT AAA TTG AAC AAT 1872
Val Ile Lys Thr Gly Thr Cys Pro Phe Ser Phe Asp Lys Leu Asn Asn
    610                 615                 620

                    A*
TAC TTG ACT TTT AAC ACG TTC TGT TTG TCG TTG AGT CCT GTT GGT GCT 1920
Tyr Leu Thr Phe Asn Thr Phe Cys Leu Ser Leu Ser Pro Val Gly Ala
625                 Lys*                635                 640
                    630

AAT TGC AAG TTT GAT GTT GCT GCA CGT ACA AGA ACC AAT GAG CAG GTT 1968
Asn Cys Lys Phe Asp Val Ala Ala Arg Thr Arg Thr Asn Glu Gln Val
                645                 650                 655

                     G*
GTT AGA AGT CTA TAT ATA ATA TAT GAA GAA GGA GAC AAC ATA GTG GGT 2016
Val Arg Ser Leu Tyr Ile Ile Tyr Glu Glu Gly Asp Asn Ile Val Gly
            660     Val*        665                 670
```

FIG. 5-7

```
GTA CCG TCT GAT GAT AGC GGT CTG CAC GAT TTG TCT GTG CTA CAC CTA 2064
Val Pro Ser Asp Asp Ser Gly Leu His Asp Leu Ser Val Leu His Leu
        675                 680                 685

GAC TCC TGT ACA GAT TAC AAT ATA TAT GGT AGA ACT GGT GTT GGT ATT 2112
Asp Ser Cys Thr Asp Tyr Asn Ile Tyr Gly Arg Thr Gly Val Gly Ile
    690                 695                 700

ATT AGA CGA ACT AAC AGT ACG CTA CTT AGT GGC TTA TAT TAC ACA TCA 2160
Ile Arg Arg Thr Asn Ser Thr Leu Leu Ser Gly Leu Tyr Tyr Thr Ser
705                 710                 715                 720

CTA TCA GGT GAT TTG TTA GGC TTT AAA AAT GTT AGT GAT GGT GTC ATT 2208
Leu Ser Gly Asp Leu Leu Gly Phe Lys Asn Val Ser Asp Gly Val Ile
                725                 730                 735

TAT TCT GTG ACG CCA TGT GAT GTA AGC GCA CAA GCG GCT GTT ATT GAT 2256
Tyr Ser Val Thr Pro Cys Asp Val Ser Ala Gln Ala Ala Val Ile Asp
            740                 745                 750

GGT GCC ATA GTT GGA GCT ATG ACT TCC ATT AAC AGT GAA CTG TTA GGT 2304
Gly Ala Ile Val Gly Ala Met Thr Ser Ile Asn Ser Glu Leu Leu Gly
        755                 760                 765

CTA ATA CAT TGG ACA ACG ACA CCT AAT TTT TAT TAC TAC TCT ATA TAT 2352
Leu Ile His Trp Thr Thr Thr Pro Asn Phe Tyr Tyr Tyr Ser Ile Tyr
    770                 775                 780

AAT TAC ACA AGT GAG AGG ACT CGT GGC ACT GCA ATT GAC AGT AAc GAT 2400
Asn Tyr Thr Ser Glu Arg Thr Arg Gly Thr Ala Ile Asp Ser Asn Asp
785                 790                 795                 800
```

FIG. 5-8

```
GTT GAT TGT GAA CCT GTC ATA ACC TAT TCT AAT ATA GGT GTT TGT AAA 2448
Val Asp Cys Glu Pro Val Ile Thr Tyr Ser Asn Ile Gly Val Cys Lys
                805                 810                 815

AAT GGT GCT TTG GTT TTT ATT AAC GTC ACA CAT TCT GAC GGA GAC GTG 2496
Asn Gly Ala Leu Val Phe Ile Asn Val Thr His Ser Asp Gly Asp Val
            820                 825                 830

CAA CCA ATT AGC ACT GGT AAT GTC ACG ATA CCT ACA AAT TTT ACC ATA 2544
Gln Pro Ile Ser Thr Gly Asn Val Thr Ile Pro Thr Asn Phe Thr Ile
        835                 840                 845

TCT GTG CAA GTT GAA TAC ATG CAG GTT TAC ACT ACA CCA GTA TCA ATA 2592
Ser Val Gln Val Glu Tyr Met Gln Val Tyr Thr Thr Pro Val Ser Ile
    850                 855                 860

GAT TGT GCA AGA TAC GTT TGT AAT GGT AAC CCT AGA TGT AAC AAA TTG 2640
Asp Cys Ala Arg Tyr Val Cys Asn Gly Asn Pro Arg Cys Asn Lys Leu
865                 870                 875                 880

TTA ACA CAA TAT GTG TCT GCA TGT CAA ACT ATT GAA CAA GCA CTT GCA 2688
Leu Thr Gln Tyr Val Ser Ala Cys Gln Thr Ile Glu Gln Ala Leu Ala
                885                 890                 895

~TG GGT GCC AGA CTT GAA AAC ATG GAG GTT GAT TCC ATG TTG TTT GTC 2736
Met Gly Ala Arg Leu Glu Asn Met Glu Val Asp Ser Met Leu Phe Val
            900                 905                 910

TCG GAA AAT GCC CTT AAA TTG GCA TCT GTT GAG GCG TTC AAT AGT ACA 2784
Ser Glu Asn Ala Leu Lys Leu Ala Ser Val Glu Ala Phe Asn Ser Thr
        915                 920                 925
```

FIG. 5-9

```
GAA AAT TTA GAT CCT ATT TAC AAA GAA TGG CCT AGC ATA GGT GGT TCT 2832
Glu Asn Leu Asp Pro Ile Tyr Lys Glu Trp Pro Ser Ile Gly Gly Ser
    930                 935                 940

TGG CTA GGA GGT CTA AAA GAT ATA CTA CCG TCC CAT AAT AGC AAA CGT 2880
Trp Leu Gly Gly Leu Lys Asp Ile Leu Pro Ser His Asn Ser Lys Arg
945                 950                 955                 960

AAG TAT GGT TCT GCT ATA GAA GAT TTG CTT TTT GAT AAA GTT GTA ACA 2928
Lys Tyr Gly Ser Ala Ile Glu Asp Leu Leu Phe Asp Lys Val Val Thr
                965                 970                 975

TCT GGT TTA GGT ACA GTT GAT GAA GAT TAT AAA CGT TGT ACT GGT GGT 2976
Ser Gly Leu Gly Thr Val Asp Glu Asp Tyr Lys Arg Cys Thr Gly Gly
            980                 985                 990

TAC GAC ATA GCA GAC TTG GTG TGT GCT CAA TAT TAC AAT GGC ATC ATG 3024
Tyr Asp Ile Ala Asp Leu Val Cys Ala Gln Tyr Tyr Asn Gly Ile Met
        995                 1000                1005

GTT CTA CCA GGT GTA GCT AAT GCT GAC AAG ATG ACT ATG TAC ACA GCA 3072
Val Leu Pro Gly Val Ala Asn Ala Asp Lys Met Thr Met Tyr Thr Ala
    1010                1015                1020

TCA CTT GCA GGT GGT ATA ACA TTA GGT GCA CTT GGT GGT GGC GCC GTG 3120
Ser Leu Ala Gly Gly Ile Thr Leu Gly Ala Leu Gly Gly Gly Ala Val
1025                1030                1035                1040

GCT ATA CCT TTT GCA GTA GCA GTA CAG GCT AGA CTT AAT TAT GTT GCT 3168
Ala Ile Pro Phe Ala Val Ala Val Gln Ala Arg Leu Asn Tyr Val Ala
                1045                1050                1055
```

FIG. 5-10

```
CTA CAA ACT GAT GTA TTG AAT AAA AAC CAA CAG ATC CTG GCT AAT GCT 3216
Leu Gln Thr Asp Val Leu Asn Lys Asn Gln Gln Ile Leu Ala Asn Ala
            1060                1065                1070

TTC AAT CAA GCT ATT GGT AAC ATT ACA CAG GCT TTT GGT AAG GTT AAT 3264
Phe Asn Gln Ala Ile Gly Asn Ile Thr Gln Ala Phe Gly Lys Val Asn
        1075                1080                1085

GAT GCT ATA CAT CAA ACA TCA CAA GGT CTT GCC ACT GTT GCT AAA GCG 3312
Asp Ala Ile His Gln Thr Ser Gln Gly Leu Ala Thr Val Ala Lys Ala
    1090                1095                1100

TTG GCA AAA GTG CAA GAT GTT GTC AAC ACA CAA GGG CAA GCT TTA AGT 3360
Leu Ala Lys Val Gln Asp Val Val Asn Thr Gln Gly Gln Ala Leu Ser
1105                1110                1115                1120

CAC CTT ACA GTA CAA TTG CAA AAT AAT TTT CAA GCC ATT AGT AGT TCT 3408
His Leu Thr Val Gln Leu Gln Asn Asn Phe Gln Ala Ile Ser Ser Ser
                1125                1130                1135

ATT AGT GAT ATT TAT AAC AGG CTT GAC GAA CTG AGT GCT GAT GCA CAA 3456
Iie Ser Asp Ile Tyr Asn Arg Leu Asp Glu Leu Ser Ala Asp Ala Gln
            1140                1145                1150

GTT GAT AGG CTG ATT ACA GGT AGA CTT ACA GCA CTT AAT GCA TTT GTG 3504
Val Asp Arg Leu Ile Thr Gly Arg Leu Thr Ala Leu Asn Ala Phe Val
        1155                1160                1165

TCT CAG ACT CTA ACC AGA CAA GCA GAG GTT AGG GCT AGT AGA CAA CTT 3552
Ser Gln Thr Leu Thr Arg Gln Ala Glu Val Arg Ala Ser Arg Gln Leu
    1170                1175                1180
```

FIG. 5-11

```
GCC AAA GAC AAG GTT AAT GAA TGT GTT AGG TCT CAG TCT CAG AGA TTC 3600
Ala Lys Asp Lys Val Asn Glu Cys Val Arg Ser Gln Ser Gln Arg Phe
1185                1190                1195                1200

GGA TTC TGT GGT AAT GGT ACA CAT TTG TTT TCA CTA GCA AAT GCA GCA 3648
Gly Phe Cys Gly Asn Gly Thr His Leu Phe Ser Leu Ala Asn Ala Ala
                1205                1210                1215

CCA AAT GGC ATG ATT TTC TTT CAT ACA GTA CTA TTA CCA ACA GCT TAT 3696
Pro Asn Gly Met Ile Phe Phe His Thr Val Leu Leu Pro Thr Ala Tyr
            1220                1225                1230

GAA ACT GTA ACA GCT TGG TCA GGT ATT TGT GCT TCA GAT GGC GAT CGC 3744
Glu Thr Val Thr Ala Trp Ser Gly Ile Cys Ala Ser Asp Gly Asp Arg
        1235                1240                1245

ACT TTC GGA CTT GTC GTT AAA GAT GTG CAG TTG ACG TTG TTT CGT AAT 3792
Thr Phe Gly Leu Val Val Lys Asp Val Gln Leu Thr Leu Phe Arg Asn
    1250                1255                1260

CTA GAT GAC AAG TTC TAT TTG ACC CCC AGA ACT ATG TAT CAG CCT AGA 3840
Leu Asp Asp Lys Phe Tyr Leu Thr Pro Arg Thr Met Tyr Gln Pro Arg
1265                1270                1275                1280

GTT GCA ACT AGT TCT GAT TTT GTT CAA ATT GAA GGG TGT GAT GTG TTG 3888
Val Ala Thr Ser Ser Asp Phe Val Gln Ile Glu Gly Cys Asp Val Leu
                1285                1290                1295

TTT GTC AAC GAG ACT GTA ATT GAT TTG CCT AGT ATT ATA CCT GAC TAT 3936
Phe Val Asn Ala Thr Val Ile Asp Leu Pro Ser Ile Ile Pro Asp Tyr
            1300                1305                1310
```

FIG. 5-12

```
ATT GAC ATT AAT CAA ACT GTT CAA GAC ATA TTA GAA AAT TAC AGA CCA 3984
Ile Asp Ile Asn Gln Thr Val Gln Asp Ile Leu Glu Asn Tyr Arg Pro
        1315                1320                1325

AAC TGG ACT GTA CCT GAA TTT ACA CTT GAT ATT TTC AAC ACA ACC TAT 4032
Asn Trp Thr Val Pro Glu Phe Thr Leu Asp Ile Phe Asn Thr Thr Tyr
    1330                1335                1340

TTA AAT CTG ACT GGT GAA ATT GAT GAC TTA GAG TTT AGG TCG GAA AAG 4080
Leu Asn Leu Thr Gly Glu Ile Asp Asp Leu Glu Phe Arg Ser Glu Lys
1345                1350                1355                1360

CTA CAT AAC ACT ACA GTA GAA CTT GCC ATT CTC ATT GAT AAC ATT AAT 4128
Leu His Asn Thr Thr Val Glu Leu Ala Ile Leu Ile Asp Asn Ile Asn
                1365                1370                1375

AAT ACA TTA GTC AAT CTT GAA TGG CTC AAT AGA ATT GAA ACT TAT GTA 4176
Asn Thr Leu Val Asn Leu Glu Trp Leu Asn Arg Ile Glu Thr Tyr Val
            1380                1385                1390

AAA TGG CCT TGG TAT GTG TGG CTA CTG ATA GGT TTA GTA GTA GTA TTT 4224
Lys Trp Pro Trp Tyr Val Trp Leu Leu Ile Gly Leu Val Val Val Phe
        1395                1400                1405

TGC ATA CCA TTA CTG CTA TTT TGC TGT TTT AGC ACA GGT TGT TGT GGA 4272
Cys Ile Pro Leu Leu Leu Phe Cys Cys Phe Ser Thr Gly Cys Cys Gly
    1410                1415                1420

TGC ATA GGT TGT TTA GGA AGT TGT TGT CAC TCT ATA TGT AGT AGA AGA 4320
Cys Ile Gly Cys Leu Gly Ser Cys Cys His Ser Ile Cys Ser Arg Arg
1425                1430                1435                1440

CAA TTT GAA AAT TAT GAA CCA ATT GAA AAA GTG CAT GTC CAC         4362
Gln Phe Glu Asn Tyr Glu Pro Ile Glu Lys Val His Val His
                1445                1450

TAA                                                             4365
```

FIG. 6

TN406, nucleotides 302 - 671 [SEQ ID NO:29]
TN406, amino acids 102 - 223 [SEQ ID NO:30]

```
GT GGT AAA CCA TTA TTA TTT CAT GTG CAT GGT GAG CCT 339
   Gly Lys Pro Leu Leu Phe His Val His Gly Glu Pro
   102             106                 111

GTT AGT GTT ATT ATA TAT ATA TCG GCT TAT AGG GAT GAT 378
Val Ser Val Ile Ile Tyr Ile Ser Ala Tyr Arg Asp Asp
        116                 121                 126

GTG CAA CAA AGG CCC CTT TTA AAA CAT GGG TTA GTG TGC 417
Val Gln Gln Arg Pro Leu Leu Lys His Gly Leu Val Cys
                131                 136

ATA ACT AAA AAT CGC CAT ATT AAC TAT GAA CAA TTC ACC 456
Ile Thr Lys Asn Arg His Ile Asn Tyr Glu Gln Phe Thr
    141                 146                 151

TCC AAC CAG TGG AAT.TCC ACA TGT ACG GGT GCT GAC AGA 495
Ser Asn Gln Trp Asn Ser Thr Cys Thr Gly Ala Asp Arg
            156                 161

AAA ATT CCT TTC TCT GTC ATA CCC ACG GAC AAT GGA ACA 534
Lys Ile Pro Phe Ser Val Ile Pro Thr Asp Asn Gly Thr
166                 171                 176

AAA ATC TAT GGT CTT GAG TGG AAT GAT GAC TTT GTT ACA 573
Lys Ile Tyr Gly Leu Glu Trp Asn Asp Asp Phe Val Thr
    181                 186                 191

GCT TAT ATT AGT GGT CGT TCT TAT CAC TTG AAC ATC AAT 612
Ala Tyr Ile Ser Gly Arg Ser Tyr His Leu Asn Ile Asn
            196                 201

ACT AAT TGG TTT AAC AAT GTC ACA CTT TTG TAT TCA CGC 651
Thr Asn Trp Phe Asn Asn Val Thr Leu Leu Tyr Ser Arg
206                 211                 216

TCA AGC ATT GCT ACC TGG GA                         671
Ser Ser Ile Ala Thr Trp
        221
```

FIG. 7-1

FECV, Nucleotides 1- 4365 [SEQ ID NO:31]
FECV, amino acids 1- 1454 [SEQ ID NO:32]

```
ATG ATT GTG CTC GTA ACT TGC CTC TTG TTG TTA TGC TCG TAC CAC ACT    48
Met Ile Val Leu Val Thr Cys Leu Leu Leu Leu Cys Ser Tyr His Thr
 1               5                  10                  15

GTT TCG AGT ACG TCA AAC AAT GAT TGT AGA CAA GTT AAC GTA ACA CAA    96
Val Ser Ser Thr Ser Asn Asn Asp Cys Arg Gln Val Asn Val Thr Gln
             20                  25                  30

TTA GCT GGC AAT GAA AAC CTT ATT AGA GAC TTT TTG TTT CAA AGT TTT   144
Leu Ala Gly Asn Glu Asn Leu Ile Arg Asp Phe Leu Phe Gln Ser Phe
         35                  40                  45

AAA GAA GAA GGA ATT GTA GTT GTT GGT GGT TAT TAC CCT ACA GAG GTG   192
Lys Glu Glu Gly Ile Val Val Val Gly Gly Tyr Tyr Pro Thr Glu Val
     50                  55                  60

TGG TAC AAC TGC TCT AGA ACA GCA ACT ACC ACT GCC TAT GAG TAT TTT   240
Trp Tyr Asn Cys Ser Arg Thr Ala Thr Thr Thr Ala Tyr Glu Tyr Phe
 65                  70                  75                  80

AAT AAT ATA CAT GCC TTT TAT TTT GAT ATG GAA GCT ATG GAA AAT AGC   288
Asn Asn Ile His Ala Phe Tyr Phe Asp Met Glu Ala Met Glu Asn Ser
                 85                  90                  95

ACT GGT AAT GCA CGT GGT AAA CCT CTA TTA TTT CAT GTT CAT GGT GAA   336
Thr Gly Asn Ala Arg Gly Lys Pro Leu Leu Phe His Val His Gly Glu
 ↑          100                 105                 110
97 of WSU 1146
amino acid #62 of AR58-3
```

FIG. 7-2

```
CCT GTT AGT ATC ATC ATA TAT ATA TCA GCT TAT GGG GAT GAT GTG CAA 384
Pro Val Ser Ile Ile Ile Tyr Ile Ser Ala Tyr Gly Asp Asp Val Gln
        115                 120                 125

CAA AGG CCA CTT TTA GAA CAT GGG TTA TTG TGC ATT ACT AAA AAT CGC 432
Gln Arg Pro Leu Leu Glu His Gly Leu Leu Cys Ile Thr Lys Asn Arg
    130                 135                 140

AAT ATT GAC TAT AAC ACC TTC ACC AGC AAC CAG TGG GAT TCC ATA TGT 480
Asn Ile Asp Tyr Asn Thr Phe Thr Ser Asn Gln Trp Asp Ser Ile Cys
145                 150                 155                 160

ACG GGT AAT GAC AGA AAA ATT CCT TTC TCT GTC ATA CCC AGG GAT AAT 528
Thr Gly Asn Asp Arg Lys Ile Pro Phe Ser Val Ile Pro Arg Asp Asn
                165                 170                 175

GGA ACA AAA ATC TAT GGG CTT GAG TGG AAT GAT GAA TTT GTT ACA GCG 576
Gly Thr Lys Ile Tyr Gly Leu Glu Trp Asn Asp Glu Phe Val Thr Ala
            180                 185                 190

TAT ATT AGT GGT CGT TCT TAT AAT TGG AAC ATC AAT AAT AAC TGG TTT 624
Tyr Ile Ser Gly Arg Ser Tyr Asn Trp Asn Ile Asn Asn Asn Trp Phe
        195                 200                 205

AAC AAT GTC ACA CTT TTG TAT TCA CGC TCA AGC ACT GCT ACC TGG GAA 672
Asn Asn Val Thr Leu Leu Tyr Ser Arg Ser Ser Thr Ala Thr Trp Glu
    210                 215                 220
```

FIG. 7-3

```
TAC AGT GCT GCA TAT GTT TAC CAA GGT GTT TCT AAC TTC ACT TAT TAC   720
Tyr Ser Ala Ala Tyr Val Tyr Gln Gly Val Ser Asn Phe Thr Tyr Tyr
225                 230                 235                 240

AAG TTA AAT AAC ACC AAT GGT TTA AAA ACC TAT GAA TTT TGT GAG GAT   768
Lys Leu Asn Asn Thr Asn Gly Leu Lys Thr Tyr Glu Phe Cys Glu Asp
                245                 250 ..              255

TAT GAA TAT TGC ACT GGC TAC GCC ACT AAT GTC TTT GCT CCA ACT GTG   816
Tyr Glu Tyr Cys Thr Gly Tyr Ala Thr Asn Val Phe Ala Pro Thr Val
            260                 265                 270

GGA GGT TAC ATA CCT GAT GGA TTT AGT TTT AAC AAT TGG TTT TTG CTT   864
Gly Gly Tyr Ile Pro Asp Gly Phe Ser Phe Asn Asn Trp Phe Leu Leu
        275                 280                 285

ACA AAT AGC TCC ACT TTT CTT AGT GGC AGA TTT GTA ACA AAC CAA CCA   912
Thr Asn Ser Ser Thr Phe Val Ser Gly Arg Phe Val Thr Asn Gln Pro
    290                 295                 300

CTA TTA GTT AAC TGC TTA TGG CCA GTG CCC AGT TTT GGT GTA GCA GCA   960
Leu Leu Val Asn Cys Leu Trp Pro Val Pro Ser Phe Gly Val Ala Ala
305                 310                 315                 320

CAA GAA TTT TGT TTT GAA GGT GCG CAG TTT AGT CAG TGT AGT GGT GTA   1008
Gln Glu Phe Cys Phe Glu Gly Ala Gln Phe Ser Gln Cys Ser Gly Val
            325                 330                 335

TCT TTA AAT AAC ACA GTA GAT GTT ATT AGA TTC AAT CTT AAT TTC ACC   1056
Ser Leu Asn Asn Thr Val Asp Val Ile Arg Phe Asn Leu Asn Phe Thr
            340                 345                 350
```

FIG. 7-4

```
GCA GAT GTA CAA TCT GGT ATG GGT GCT ACA GTG TTT TCG TTG AAT ACA 1104
Ala Asp Val Gln Ser Gly Met Gly Ala Thr Val Phe Ser Leu Asn Thr
        355                 360                 365

ACG GGT GGT GTC ATT CTT GAA GTT TCA TGT TAT AAT GAC ACA GTG AGT 1152
Thr Gly Gly Val Ile Leu Glu Val Ser Cys Tyr Asn Asp Thr Val Ser
    370                 375                 380

GAG TCT AGT TTT TAC AGT TAT GGT GAA ATT CCG TTC GGC ATA ACT GAT 1200
Glu Ser Ser Phe Tyr Ser Tyr Gly Glu Ile Pro Phe Gly Ile Thr Asp
385                 390                 395                 400

GGA CCA CGG TAC TGT TAT GTA CTT TAC AAT GGC ACA GCT CTT AAG TAT 1248
Gly Pro Arg Tyr Cys Tyr Val Leu Tyr Asn Gly Thr Ala Leu Lys Tyr
                405                 410                 415

TTA GGA ACA TTA CCA CCT AGT GTA AAG GAA ATT GCT ATT AGT AAG TGG 1296
Leu Gly Thr Leu Pro Pro Ser Val Lys Glu Ile Ala Ile Ser Lys Trp
            420                 425                 430

GGC CAT TTT TAT ATT AAT GGT TAC AAT TTC TTT AGC ACA TTT CCT ATT 1344
Gly His Phe Tyr Ile Asn Gly Tyr Asn Phe Phe Ser Thr Phe Pro Ile
        435                 440                 445

GAT TGT ATA TCT TTT AAC TTA ACC ACT GGT GAT AGT GGA GCT TTT TGG 1392
Asp Cys Ile Ser Phe Asn Leu Thr Thr Gly Asp Ser Gly Ala Phe Trp
    450                 455                 460

ACA ATT GCT TAC ACA TCG TAC ACT GAG GCA TTA GTA CAA GTT GAA AAC 1440
Thr Ile Ala Tyr Thr Ser Tyr Thr Glu Ala Leu Val Gln Val Glu Asn
465                 470                 475                 480
```

FIG. 7-5

```
ACA GCT ATT AAA AAG GTG ACG TAT TGT AAC AGT CAC ATT AAT AAC ATT 1488
Thr Ala Ile Lys Lys Val Thr Tyr Cys Asn Ser His Ile Asn Asn Ile
            485                 490                 495

AAG TGT TCT CAA CTT ACT GCT AAT TTG AAT AAT GGA TTT TAT CCT GTT 1536
Lys Cys Ser Gln Leu Thr Ala Asn Leu Asn Asn Gly Phe Tyr Pro Val
            500                 505                 510

GCT TCA AGT GAG GTT GGT CTT GTG AAT AAG AGT GTT GTG TTA TTA CCT 1584
Ala Ser Ser Glu Val Gly Leu Val Asn Lys Ser Val Val Leu Leu Pro
        515                 520                 525

ATC TTT TTC GCA CAT ACC GCT ATC AAT ATA ACC ATT GAT CTT GGT ATG 1632
Ile Phe Phe Ala His Thr Ala Ile Asn Ile Thr Ile Asp Leu Gly Met
    530                 535                 540

AAG CGT AGC GGT TAT GGT CAA CCC ATA GCA TCA ACA TTA AGT AAC ATT 1680
Lys Arg Ser Gly Tyr Gly Gln Pro Ile Ala Ser Thr Leu Ser Asn Ile
545                 550                 555                 560

ACA CTA CCA ATG CAG GAT AAT AAC ACA GAT GTG TAC TGT ATT CGT TCT 1728
Thr Leu Pro Met Gln Asp Asn Asn Thr Asp Val Tyr Cys Ile Arg Ser
            565                 570                 575

AAC CAG TTT TCA GTT TAT GTT CAT TCT ATT TGT AAG AGT TCT TTA TGG 1776
Asn Gln Phe Ser Val Tyr Val His Ser Ile Cys Lys Ser Ser Leu Trp
        580                 585                 590

GAC AAT ATT TTT AAT CAA GAA TGC ACG GAT GTT TTA GAT GCC ACA GCT 1824
Asp Asn Ile Phe Asn Gln Glu Cys Thr Asp Val Leu Asp Ala Thr Ala
        595                 600                 605
```

FIG. 7-6

```
GTT ATA AAG ACT GGT ACT TGT CCT TTC TCA TTT GAT AAA TTG AAC AAT 1872
Val Ile Lys Thr Gly Thr Cys Pro Phe Ser Phe Asp Lys Leu Asn Asn
    610                 615                 620

TAC TTA ACT TTT AAC AAG TTC TGT TTG TCG TTG AGT CCT GTT GGC GCT 1920
Tyr Leu Thr Phe Asn Lys Phe Cys Leu Ser Leu Ser Pro Val Gly Ala
625                 630                 635                 640

AAC TGC AAG TTT GAT GTT GCC GCA CGT ACA AGA ACC AAT GAG CAA GTT 1968
Asn Cys Lys Phe Asp Val Ala Ala Arg Thr Arg Thr Asn Glu Gln Val
                645                 650                 655

GTT AGA AGT CTA TAT GTA ATA TAT GAA GAA GGA GAC AAC ATA GTT GGT 2016
Val Arg Ser Leu Tyr Val Ile Tyr Glu Glu Gly Asp Asn Ile Val Gly
            660                 665                 670

GTA CCG TCT GAT AAT AGC GGT CTG CAC GAT TTG TCT GTG CTA CAC CTA 2064
Val Pro Ser Asp Asn Ser Gly Leu His Asp Leu Ser Val Leu His Leu
        675                 680                 685

GAC TCC TGT ACA GAG TAT AAT ATA TAT GGT AGA ACT GGT GTT GGT ATT 2112
Asp Ser Cys Thr Glu Tyr Asn Ile Tyr Gly Arg Thr Gly Val Gly Ile
    690                 695                 700

ATT AGA CAA ACT AAC AGT ACG CTA CTT AGC GGC TTA TAT TAC ACA TCA 2160
Ile Arg Gln Thr Asn Ser Thr Leu Leu Ser Gly Leu Tyr Tyr Thr Ser
705                 710                 715                 720

CTA TCA GGT GAT TTG TTA GGC TTT AAA AAT GTT AGT GAT GGT GTC ATC 2208
Leu Ser Gly Asp Leu Leu Gly Phe Lys Asn Val Ser Asp Gly Val Ile
                725                 730                 735
```

FIG. 7-7

```
TAT TCT GTG ACG CCA TGT GAT GTA AGC GCA CAA GCG 4CT GTT ATT GAT 2256
Tyr Ser Val Thr Pro Cys Asp Val Ser Ala Gln Ala Ala Val Ile Asp
            740                 745                 750

GGT GCC ATA GTT GGA GCT ATG ACT TCC ATT AAC AGT GAA CTG TTA GGT 2304
Gly Ala Ile Val Gly Ala Met Thr Ser Ile Asn Ser Glu Leu Leu Gly
        755                 760                 765

CTA AAA CAC TGG ACA ACA ACA CCT AAT TTT TAT TAC TAC TCT ATA TAT 2352
Leu Lys His Trp.Thr Thr Thr Pro Asn Phe Tyr Tyr Tyr Ser Ile Tyr
    770                 775                 780

AAT TAT ACA AAT GAG AGG ACT CGT GGC ACT GCA ATT GAC AGT AAC GAT 2400
Asn Tyr Thr Asn Glu Arg Thr Arg Gly Thr Ala Ile Asp Ser Asn Asp
785                 790                 795                 800

GTT GAT TGT GAA CCT ATC ATA ACC TAT TCT AAC ATA GGT GTT TGT AAA 2448
Val Asp Cys Glu Pro Ile Ile Thr Tyr Ser Asn Ile Gly Val Cys Lys
                805                 810                 815

AAT GGT GCT TTG GTT TTT ATT AAC GTC ACA CAT TCT GAT GGA GAC GTG 2496
Asn Gly Ala Leu Val Phe Ile Asn Val Thr His Ser Asp Gly Asp Val
            820                 825                 830

CAA CCA ATT AGC ACT GGT ACT GTC ACG ATA CCT ACA AAC TTT ACC ATA 2544
Gln Pro Ile Ser Thr Gly Thr Val Thr Ile Pro Thr Asn Phe Thr Ile
        835                 840                 845

TCT GTG CAA GTC GAA TAC ATT CAG GTT ACC CCT ACA CCA GTA TCA ATA 2592
Ser Val Gln Val Glu Tyr Ile Gln Val Tyr Thr Thr Pro Val Ser Ile
    850                 855                 860
```

FIG. 7-8

```
GAT TGT GCA AGA TAC GTT TGC AAT GGT AAC CCT AGA TGT AAC AAA TTG   2640
Asp Cys Ala Arg Tyr Val Cys Asn Gly Asn Pro Arg Cys Asn Lys Leu
865                 870                 875                 880

TTA ACA CAA TAT GTT TCT GCA TGT CAA ACT ATT GAG CCA GCA CTT GCA   2688
Leu Thr Gln Tyr Val Ser Ala Cys Gln Thr Ile Glu Gln Ala Leu Ala
                885                 890                 895

ATG GGT GCC AGA CTT GAA AAC ATG GAG GTT GAT TCC ATG TTG TTC GTT   2736
Met Gly Ala Arg Leu Glu Asn Met Glu Val Asp Ser Met Leu Phe Val
            900                 905                 910

TCT GAA AAT GCC CTT AAA TTG GCA TCT GTT GAG GCG TTC AAT AGT ACA   2784
Ser Glu Asn Ala Leu Lys Leu Ala Ser Val Glu Ala Phe Asn Ser Thr
        915                 920                 925

GAA AAT TTA GAC CCT ATT TAC AAA GAA TGG CCT AAC ATA GGT GGT TCT   2832
Glu Asn Leu Asp Pro Ile Tyr Lys Glu Trp Pro Asn Ile Gly Gly Ser
    930                 935                 940

TGG TTA GGA GGT TTA AAA GAC ATA CTG CCG TCC CAT AAT AGC AAA CGT   2880
Trp Leu Gly Gly Leu Lys Asp Ile Leu Pro Ser His Asn Ser Lys Arg
945                 950                 955                 960

AAG TAT CGT TCT GCT ATA GAA GAC TTG CTT TTT GAT AAq GTT GTA ACT   2928
Lys Tyr Arg Ser Ala Ile Glu Asp Leu Leu Phe Asp Lys Val Val Thr
                965                 970                 975

TCT GGT TTA GGT ACA GTT GAT GAA GAT TAT AAA CGT TGT ACA GGT GGT   2976
Ser Gly Leu Gly Thr Val Asp Glu Asp Tyr Lys Arg Cys Thr Gly Gly
            980                 985                 990
```

FIG. 7-9

```
TAT GAC ATA GCC GAC TTA GTG TGT GCT CAA TAT TAC AiT GGC ATC ATG 3024
Tyr Asp Ile Ala Asp Leu Val Cys Ala Gln Tyr Tyr Asn Gly Ile Met
        995                     1000                    1005

GTG TTA CCT GGT GTA GCT AAT GAT GAC AAG ATG ACT ATG TAC ACA GCA 3072
Val Leu Pro Gly Val Ala Asn Asp Asp Lys Met Thr Met Tyr Thr Ala
    1010                    1015                    1020

TCT CTT GCA GGT GGT ATA ACA CTA GGT GCA CTT GGT GGT GGC GCC GTT 3120
Ser Leu Ala Gly Gly Ile Thr Leu Gly Ala Leu Gly Gly Gly Ala Val
1025                1030                    1035                1040

GCT ATA CCT TTT GCA GTA GCA GTT CAA GCT AGA CTT AAT TAT GTT GCT 3168
Ala Ile Pro Phe Ala Val Ala Val Gln Ala Arg Leu Asn Tyr Val Ala
                1045                    1050                1055

CTA CAA ACT GAT GTA TTG AAT AAA AAC CAG CAG ATC CTG GCT AAT GCT 3216
Leu Gln Thr Asp Val Leu Asn Lys Asn Gln Gln Ile Leu Ala Asn Ala
            1060                    1065                1070

TTC AAT CAA GCT ATT GGT AAC ATT ACA CAG GCA TTT GGC AAG GTT AAT 3264
Phe Asn Gln Ala Ile Gly Asn Ile Thr Gln Ala Phe Gly Lys Val Asn
        1075                    1080                    1085

GAT GCT ATA CAT CAA ACA TCA AAA GGT CTT GCA ACT GTT GCT AAA GCA 3312
Asp Ala Ile His Gln Thr Ser Lys Gly Leu Ala Thr Val Ala Lys Ala
    1090                    1095                    1100

TTG GCA AAA GTG CAA GAT GTT GTC AAC ACA CAA GGG CAA GCT TTA AGC 3360
Leu Ala Lys Val Gln Asp Val Val Asn Thr Gln Gly Gld Ala Leu Ser
1105                1110                    1115                1120
```

FIG. 7-10

```
CAC CTA ACA GTA CAA TTG CAA AAT AAT TTT CAA GCC ATT AGT AGC TCT 3408
His Leu Thr Val Gln Leu Gln Asn Asn Phe Gln Ala Ile Ser Ser Ser
                1125                1130                1135

ATT AGT GAT ATT TAT AAC AGG CTT GAC GAA CTG AGT GCT GAT GCA CAA 3456
Ile Ser Asp Ile Tyr Asn Arg Leu Asp Glu Leu Ser Ala Asp Ala Gln
            1140                1145                1150

GTT GAT AGG CTG ATT ACA GGA AGA CTT ACA GCA CTT AAT GCA TTT GTG 3504
Val Asp Arg Leu Ile Thr Gly Arg Leu Thr Ala Leu Asn Ala Phe Val
        1155                1160                1165

TCT CAG ACT CTA ACC AGA CAA GCG GAG GTT AGG GCT AGT AGA CAA CTT 3552
Ser Gln Thr Leu Thr Arg Gln Ala Glu Val Arg Ala Ser Arg Gln Leu
    1170                1175                1180

GCC AAG GAC AAG GTT AAT GAA TGT GTT AGA TCC CAA TCT CAG AGA TTT 3600
Ala Lys Asp Lys Val Asn Glu Cys Val Arg Ser Gln Ser Gln Arg Phe
1185                1190                1195                1200

GGA TTC TGT GGT AAT GGT ACA CAC TTG TTT TCA CTT GCA AAT GCA GCA 3648
Gly Phe Cys Gly Asn Gly Thr His Leu Phe Ser Leu Ala Asn Ala Ala
                1205                1210                1215

CCA AAT GGC ATG ATT TTC TTT CAT ACA GTG CTA TTA CCA ACG GCT TAT 3696
Pro Asn Gly Met Ile Phe Phe His Thr Val Leu Leu Pro Thr Ala Tyr
            1220                1225                1230

GAA ACT GTA ACA GCT TGG CCA GGT ATT TGT GCT TCA GAT GGC GAT CGC 3744
Glu Thr Val Thr Ala Trp Pro Gly Ile cys Ala Ser Asp Gly Asp Arg
        1235                1240                1245
```

FIG. 7-11

```
ACT TTT GGA CTT GTC GTT AAA GAT GTA CAG TTG ACG TTG TTT CGT AAC 3792
Thr Phe Gly Leu Val Val Lys Asp Val Gln Leu Thr Leu Phe Arg Asn
    1250                1255                1260

CTA GAT GAC AAG TTC TAT TTG ACT CCC AGA ACT ATG TAT CAG CCT AGA 3840
Leu Asp Asp Lys Phe Tyr Leu Thr Pro Arg Thr Met Tyr Gln Pro Arg
1265                1270                1275                1280

GCT GCA ACT AGT TCT GAT TTT GTT CAA ATT GAG GGG TGC GAT GTG TTG 3888
Ala Ala Thr Ser Ser Asp Phe Val Gln Ile Glu Gly Cys Asp Val Leu
                1285                1290                1295

TTT GTC AAT GCA ACT GTA ATT GAC TTG CCT AGT ATT ATA CCT GAC TAT 3936
Phe Val Asn Ala Thr Val Ile Asp Leu Pro Ser Ile Ile Pro Asp Tyr
            1300                1305                1310

ATT GAC ATC AAT CAG ACT GTT CAA GAT ATA TTA GAA AAT TAC AGA CCA 3984
Ile Asp Ile Asn Gln Thr Val Gln Asp Ile Leu Glu Asn Tyr Arg Pro
        1315                1320                1325

AAC TGG ACT GTA CCT GAA TTG ACA CTT GAT ATT TTT AAC GCA ACC TAT 4032
Asn Trp Thr Val Pro Glu Leu Thr Leu Asp Ile Phe Asn Ala Thr Tyr
    1330                1335                1340

TTA AAT CTG ACT GGT GAA ATT GAT GAC TTA GAA TTT AGG TCA GAA AAG 4080
Leu Asn Leu Thr Gly Glu Ile Asp Asp Leu Glu Phe Arg Ser Glu Lys
1345                1350                1355                1360

CTA CAC AAT ACC ACT GTA GAA CTT GCC ATT CTC ATT GAC AAC ATT AAC 4128
Leu His Asn Thr Thr Val Glu Leu Ala Ile Leu Ile Asp Asn Ile Asn
                1365                1370                1375
```

FIG. 7-12

```
AAC ACA TTA GTC AAT CTT GAA TGG CTC AAT AGA ATT GAA ACT TAT GTA 4176
Asn Thr Leu Val Asn Leu Glu Trp Leu Asn Arg Ile Glu Thr Tyr Val
            1380                1385                1390

AAA TGG CCT TGG TAT GTG TGG CTA CTA ATA GGC TTA GTA GTA ATA TTT 4224
Lys Trp Pro Trp Tyr Val Trp Leu Leu Ile Gly Leu Val Val Ile Phe
        1395                1400                1405

TGC ATA CCA TTA TTG CTA TTT TGC TGT TGT AGT ACA GGT TGT TGT GGA 4272
Cys Ile Pro Leu Leu Leu Phe Cys Cys Cys Ser Thr Gly Cys Cys Gly
    1410                1415                1420

TGC ATA GGT TGC TTA GGA AGT TGT TGT CAC TCT ATG TGT AGT AGA AGA 4320
Cys Ile Gly Cys Leu Gly Ser Cys Cys His Ser Met Cys Ser Arg Arg
1425                1430                1435                1440

CAA TTT GAA AAT TAT GAA CCA ATT GAA AAA GTG CAT GTC CAC         4362
Gln Phe Glu Asn Tyr Glu Pro Ile Glu Lys Val His Val His
                1445                1450

TAA                                                             4365
```

FIG. 8

UCD-2, nucleotides 1- 377 [SEQ ID NO:53]
UCD-2, amino acids 1- 125 [SEQ ID NO:54]

```
AAT GCT CGT GGT AAA CCA TTA TTA TTT CAT GTG CAT GGT GAG CCT GTT 48
Asn Ala Arg Gly Lys Pro Leu Leu Phe His Val His Gly Glu Pro Val
1                5                  10                  15

AGT GTT ATT ATA TAT ATA TCG GCT TAT AGG GAT GAT GTG CAA CAA AGG 96
Ser Val Ile Ile Tyr Ile Ser Ala Tyr Arg Asp Asp Val Gln Gln Arg
             20                  25                  30

CCC CTT TTA AAA CAT GGG TTA GTG TGC ATA ACT AAA AAT CGC CAT ATT 144
Pro Leu Leu Lys His Gly Leu Val Cys Ile Thr Lys Asn Arg His Ile
         35                  40                  45

AAC TAT GAA CAA TTC ACC TCC AAC CAG TGG AAT TCC ACA TGT ACG GGT 192
Asn Tyr Glu Gln Phe Thr Ser Asn Gln Trp Asn Ser Thr Cys Thr Gly
     50                  55                  60

GCT GAC AGA AAA ATT CCT TTC TCT GTC ATA CCC ACG GAC AAT GGA ACA 240
Ala Asp Arg Lys Ile Pro Phe Ser Val Ile Pro Thr Asp Asn Gly Thr
 65                  70                  75                  80

AAA ATC TAT GGT CTT GAG TGG AAT GAT GAC TTT GTT ACA GCT TAT ATT 288
Lys Ile Tyr Gly Leu Glu Trp Asn Asp Asp Phe Val Thr Ala Tyr Ile
                 85                  90                  95

AGT GGT CGT TCT TAT CAC TTG AAC ATC AAT ACT AAT TGG TTT AAC AAT 336
Ser Gly Arg Ser Tyr His Leu Asn Ile Asn Thr Asn Trp Phe Asn Asn
            100                 105                 110

GTC ACA CTT TTG TAT TCA CGC TCA AGC ACT GCT ACC TGG GA          377
Val Thr Leu Leu Tyr Ser Arg Ser Ser Thr Ala Thr Trp
        115                 120                 125
```

FIG. 9-1

Consensus Sequence
Nucleotides 1- 2246 [SEQ ID NO:33]
Amino acids 1- 748 [SEQ ID NO:34]

```
ATG ATT GTG CTC GTA ACT TGC CTC TTG TTG TTA TGT TCA 39
Met Ile Val Leu Val Thr Cys Leu Leu Leu Leu Cys Ser
  1             5                   10

TAC CAC ACA GTT TTG AGT ACA ACA AAT AAT GAA TGC ATA 78
Tyr His Thr Val Leu Ser Thr Thr Asn Asn Glu Cys Ile
     15                  20                  25

CAA GTT AAC GTA ACA CAA TTG GCT GGC AAT GAA AAC CTT 117
Gln Val Asn Val Thr Gln Leu Ala Gly Asn Glu Asn Leu
             30                  35

ATC AGA GAT TTT CTG TTT AGT AAC TTT AAA GAA GAA GGA 156
Ile Arg Asp Phe Leu Phe Ser Asn Phe Lys Glu Glu Gly
 40                  45                  50

AGT GTA GTT GTT GGT GGT TAT TAC CCT ACA GAG GTG TGG 195
Ser Val Val Val Gly Gly Tyr Tyr Pro Thr Glu Val Trp
         55                  60                  65

TAC AAC TGC TCT AGA ACA GCT CGA ACT ACT GCC TTT CAG 234
Tyr Asn Cys Ser Arg Thr Ala Arg Thr Thr Ala Phe Gln
                 70                  75

TAT TTT AAT AAT ATA CAT GCC TTT TAT TTT GTT ATG GAA 273
Tyr Phe Asn Asn Ile His Ala Phe Tyr Phe Val Met Glu
     80                  85                  90
```

FIG. 9-2

```
GCC ATG GAA AAT AGC ACT GGT AAT GCA CGT GGT AAA CCA 312
Ala Met Glu Asn Ser Thr Gly Asn Ala Arg Gly Lys Pro
             95                  100

TTA TTA TTT CAT GTG CAT GGT GAG CCT GTT AGT GTT ATT 351
Leu Leu Phe His Val His Gly Glu Pro Val Ser Val Ile
105                 110                 115

ATA TAT ATA TCG GCT TAT AGG GAT GAT GTG CAA CAA AGG 390
Ile Tyr Ile Ser Ala Tyr Arg Asp Asp Val Gln Gln Arg
        120                 125                 130

CCC CTT TTA AAA CAT GGG TTA GTG TGC ATA ACT AAA AAT 429
Pro Leu Leu Lys His Gly Leu Val Cys Ile Thr Lys Asn
                135                 140

CGC CAT ATT AAC TAT GAA CAA TTC ACC TCC AAC CAG TGG 468
Arg His Ile Asn Tyr Glu Gln Phe Thr Ser Asn Gln Trp
    145                 150                 155

AAT TCC ACA TGT ACG GGT GCT GAC AGA AAA ATT CCT TTC 507
Asn Ser Thr Cys Thr Gly Ala Asp Arg Lys Ile Pro Phe
            160                 165

TCT GTC ATA CCC ACG GAC AAT GGA ACA AAA ATC TAT GGT 546
Ser Val Ile Pro Thr Asp Asn Gly Thr Lys Ile Tyr Gly
170                 175                 180

CTT GAG TGG AAT GAT GAC TTT GTT ACA GCT TAT ATT AGT 585
Leu Glu Trp Asn Asp Asp Phe Val Thr Ala Tyr Ile Ser
        185                 190                 195
```

FIG. 9-3

```
GGT CGT TCT TAT CAC TTG AAC ATC AAT ACT AAT TGG TTT 624
Gly Arg Ser Tyr His Leu Asn Ile Asn Thr Asn Trp Phe
                200                 205

AAC AAT GTC ACA CTT TTG TAT TCA CGC TCA AGC ACT GCT 663
Asn Asn Val Thr Leu Leu Tyr Ser Arg Ser Ser Thr Ala
    210                 215                 220

ACC TGG GAA TAC AGT GCT GCA TAT GCT TAC CAA GGT GTT 702
Thr Trp Glu Tyr Ser Ala Ala Tyr Ala Tyr Gln Gly Val
            225                 230

TCT AAC TTC ACT TAT TAC AAG TTA AAT AAC ACC AAT GGT 741
Ser Asn Phe Thr Tyr Tyr Lys Leu Asn Asn Thr Asn Gly
235                 240                 245

CTA AAA ACC TAT GAA TTA TGT GAA GAT TAT GAA CAT TGC 780
Leu Lys Thr Tyr Glu Leu Cys Glu Asp Tyr Glu His Cys
        250                 255                 260

ACT GGC TAT GCT ACC AAT GTA TTT GCT CCG ACA TCA GGT 819
Thr Gly Tyr Ala Thr Asn Val Phe Ala Pro Thr Ser Gly
                265                 270

GGT TAC ATA CCT GAT GGA TTT AGT TTT AAY AAT TGG TTC 858
Gly Tyr Ile Pro Asp Gly Phe Ser Phe Asn Asn Trp Phe
    275                 280                 285
```

FIG. 9-4

```
TTG CTT ACA AAT AGT TCC ACT TTT GTT AGT GGC AGG TTT 897
Leu Leu Thr Asn Ser Ser Thr Phe Val Ser Gly Arg Phe
            290                 295

GTA ACA AAT CAA CCA TTA TTG ATT AAT TGC TTG TGG CCA 936
Val Thr Asn Gln Pro Leu Leu Ile Asn Cys Leu Trp Pro
300                 305                 310

GTG CCC AGT TTT GGT GTA GCA GCA CAA GAA TTT TGT TTT 957
Val Pro Ser Phe Gly Val Ala Ala Gln Glu Phe Cys Phe
        315                 320                 325

GAA GGT GCA CAG TTT AGC CAA TGT AAT GGT GTG TCT TTA 1014
Glu Gly Ala Gln Phe Ser Gln Cys Asn Gly Val Ser Leu
                330                 335

AAT AAC ACA GTG GAT GTT ATT AGA TTC AAC CTT AAT TTC 1053
Asn Asn Thr Val Asp Val Ile Arg Phe Asn Leu Asn Phe
    340                 345                 350

ACT GCA GAT GTA CAA TCT GGT ATG GGT GCT ACA GTA TTT 1092
Thr Ala Asp Val Gln Ser Gly Met Gly Ala Thr Val Phe
            355                 360

TCA CTG AAT ACA ACA GGT GGT GTC ATT CTT GAA ATT TCA 1131
Ser Leu Asn Thr Thr Gly Gly Val Ile Leu Glu Ile Ser
365                 370                 375

TGT TAT AGT GAC ACA GTG AGT GAG TCT AGT TCT TAC AGT 1170
Cys Tyr Ser Asp Thr Val Ser Glu Ser Ser Ser Tyr Ser
        380                 385                 390
```

FIG. 9-5

```
TAT GGT GAA ATC CCG TTC GGC ATA ACT GAC GGA CCA CGA 1209
Tyr Gly Glu Ile Pro Phe Gly Ile Thr Asp Gly Pro Arg
                395                 400

TAC TGT TAT GTA CTT TAC AAT GGC ACA GCT CTT AAA TAT 1248
Tyr Cys Tyr Val Leu Tyr Asn Gly Thr Ala Leu Lys Tyr
    405                 410                 415

TTA GGA ACA TTA CCA CCC AGT GTA AAG GAA ATT GCT ATT 1287
Leu Gly Thr Leu Pro Pro Ser Val Lys Glu Ile Ala Ile
            420                 425

AGT AAG TGG GGC CAT TTT TAT ATT AAT GGT TAC AAT TTC 1326
Ser Lys Trp Gly His Phe Tyr Ile Asn Gly Tyr Asn Phe
430                 435                 440

TTT AGC ACA TTT CCT ATT GRT TGT ATA TCT TTT AAT TTA 1365
Phe Ser Thr Phe Pro Ile Xaa Cys Ile Ser Phe Asn Leu
        445                 450                 455

ACC ACT GGT GTT AGT GGA GCT TTT TGG ACA ATT GCT TAC 1404
Thr Thr Gly Val Ser Gly Ala Phe Trp Thr Ile Ala Tyr
                460                 465

ACA TCG TAT ACT GAA GCA TTA GTA CAA GTT GAA AAC ACA 1443
Thr Ser Tyr Thr Glu Ala Leu Val Gln Val Glu Asn Thr
    470                 475                 480

GCT ATT AAA AAT GTG ACG TAT TGT AAC AGT CAC ATT AAT 1482
Ala Ile Lys Asn Val Thr Tyr Cys Asn Ser His Ile Asn
            485                 490
```

FIG. 9-6

```
AAC ATT AAA TGT TCT CAA CTT ACT GCT AAT TTG AAT AAT 1521
Asn Ile Lys Cys Ser Gln Leu Thr Ala Asn Leu Asn Asn
495                 500                 505

GGA TTT TAT CCT GTT GCT TCA AGT GAA GTA GGT TTC GTT 1560
Gly Phe Tyr Pro Val Ala Ser Ser Glu Val Gly Phe Val
        510                 515                 520

AAT AAG AGT GTT GTG TTA TTA CCT AGC TTT TTC ACA TAC 1599
Asn Lys Ser Val Val Leu Leu Pro Ser Phe Phe Thr Tyr
                525                 530

ACC GCT GTC AAT ATA ACC ATT GAT CTT GGT ATG AAG CTT 1638
Thr Ala Val Asn Ile Thr Ile Asp Leu Gly Met Lys Leu
    535                     540                 545

AGT GGT TAT GGT CAA CCC ATA GCC TCG ACA CTA AGT AAC 1677
Ser Gly Tyr Gly Gln Pro Ile Ala Ser Thr Leu Ser Asn
            550                 555

ATC ACA CTA CCA ATG CAG GAT AAC AAT ACT GAT GTG TAC 1716
Ile Thr Leu Pro Met Gln Asp Asn Asn Thr Asp Val Tyr
560                 565                 570

TGT ATT CGT TCT AAC CAA TTC TCA GTT TAT GTT CAT TCC 1755
Cys Ile Arg Ser Asn Gln Phe Ser Val Tyr Val His Ser
        575                 580                 585

ACT TGC AAA AGT TCT TTA TGG GAC AAT ATT TTT AAT CAA 1794
Thr Cys Lys Ser Ser Leu Trp Asp Asn Ile Phe Asn Gln
                590                 595
```

FIG. 9-7

```
GAC TGC ACG GAT GTT TTA GAG GCT ACA GCT GTT ATA AAA 1833
Asp Cys Thr Asp Val Leu Glu Ala Thr Ala Val Ile Lys
    600                 605                 610

ACT GGT ACT TGT CCT TTC TCA TTT GAT AAA TTG AAC AAT 1872
Thr Gly Thr Cys Pro Phe Ser Phe Asp Lys Leu Asn Asn
            615                 620

TAC TTG ACT TTT AAC AAG TTC TGT TTG TCG TTG AGT CCT 1911
Tyr Leu Thr Phe Asn Lys Phe Cys Leu Ser Leu Ser Pro
625                 630                 635

GTT GGT GCT AAT TGC AAG TTT GAT GTT GCT GCA CGT ACA 1950
Val Gly Ala Asn Cys Lys Phe Asp Val Ala Ala Arg Thr
        640                 645                 650

AGA ACC AAT GAG CAG GTT GTT AGA AGT CTA TAT GTA ATA 1989
Arg Thr Asn Glu Gln Val Val Arg Ser Leu Tyr Val Ile
                655                 660

TAT GAA GAA GGA GAC AAC ATA GTG GGT GTA CCG TCT GAT 2028
Tyr Glu Glu Gly Asp Asn Ile Val Gly Val Pro Ser Asp
    665                 670                 675

RAT AGC GGT CTG CAC GAT TTG TCT GTG CTA CAC CTA GAC 2067
Xaa Ser Gly Leu His Asp Leu Ser Val Leu His Leu Asp
            680                 685

TCC TGT ACA GAT TAC AAT ATA TAT GGT AGA ACT GGT GTT 2106
Ser Cys Thr Asp Tyr Asn Ile Tyr Gly Arg Thr Gly Val
690                 695                 700
```

FIG. 9-8

```
GGT ATT ATT AGA CGA ACT AAC AGT ACG CTA CTT AGT GGC 2145
Gly Ile Ile Arg Arg Thr Asn Ser Thr Leu Leu Ser Gly
        705                 710                 715

TTA TAT TAC ACA TCA CTA TCA GGT GAT TTG TTA GGC TTT 2184
Leu Tyr Tyr Thr Ser Leu Ser Gly Asp Leu Leu Gly Phe
                720                 725

AAA AAT GTT AGT GAT GGT GTC ATT TAT TCT GTG ACG CCA 2223
Lys Asn Val Ser Asp Gly Val Ile Tyr Ser Val Thr Pro
    730                 735                 740

TGT GAT GTA AGC GCA CAA GCG GC                      2246
Cys Asp Val Ser Ala Gln Ala
            745
```

RECOMBINANT FELINE CORONAVIRUS S PROTEINS

This is a continuation of U.S. application Ser. No. 07/847,018, filed Apr. 8, 1992, now abandoned, which is the U.S. national stage of PCT/US91/08525, filed Nov. 14, 1991, which is a continuation-in-part of application Ser. No. 07/698,927, filed May 13, 1991, now abandoned, which is a continuation-in-part of application Ser. No. 07/613,066, filed Nov. 14, 1990, now abandoned.

FIELD OF THE INVENTION

This invention relates generally to polypeptides useful for diagnosis and both preventive and prophylactic treatment of feline infectious peritonitis virus disease. More specifically, the invention relates to new recombinant feline coronavirus S proteins and fusion proteins.

BACKGROUND OF THE INVENTION

Feline Infectious Peritonitis (FIP) is a highly lethal disease in both wild and domestic cats, occurring predominantly in young animals although cats of all ages are susceptible. Symptoms of FIP may include anemia, neutrophilia, increased concentrations of immunoglobulin and/or fibrinogen, renal damage as indicated by high levels of urea and creatinine, and disseminated intravascular coagulation.

Previous attempts to develop an effective FIPV vaccine have been largely unsuccessful. Administration of traditional inactivated whole virus vaccines have actually predisposed cats to the development of FIP and produced a more rapid and fulminating disease after challenge. Cats vaccinated with an avirulent strain of FIPV were more readily infected than non-immunized cats and animals immunized with a sublethal dose of virulent FIPV showed inconsistent protection from challenge [Pedersen and Black, *Am. J. Vet. Res.,* 44:229–234 (1983)].

Immunization of cats with other antigenically related coronaviruses has also not been successful. In most experiments, the administration of TGEV, CCV and human coronavirus 229E has neither sensitized nor protected cats [Woods and Pedersen, *Vet. Microbiol.,* 4:11–16 (1979); Toma et al, *Rec. Med. Vet.,* 155:788–803 (1979); Barlough et al, *Can. J. Comp. Med.,* 49:303–307 (1985); Barlough et al, *Lab. Anim. Sci.,* 34:592–597 (1984); Stoddart et al, *Res. Vet. Sci.,* 45:383–388 (1988)].

Recently, a temperature-sensitive FIPV (TS-FIPV) vaccine has been developed which, when administered intranasally, is efficacious and safe upon FIPV challenge [Christianson et al, *Arch. Virol.,* 109:185–196 (1989)]. This vaccine has limited efficacy when administered subcutaneously, but appears to be effective against homologous and heterologous strains. Generally, intranasal administration is not preferred because the dosage amount is less quantifiable than other routes.

There remains a need for effective diagnostic, therapeutic and protective compositions for use in diagnosing, treating, and vaccinating animals against FIPV and serologically related infections.

SUMMARY OF THE INVENTION

In one aspect, the invention provides protein and peptide fragments of a feline coronavirus S gene. These peptides may be expressed recombinantly or synthetically and are useful as diagnostic, therapeutic or vaccinal components. In one embodiment, the feline coronavirus S-derived peptides fall within the range of amino acid numbers 1 to about 1454 of the S genomes of a variety of FIPV strains and 1 to about 1454 of the feline entiric coronavirus (FECV) S genome, or smaller peptide fragments therein. In a preferred embodiment, the feline coronavirus S-derived peptides fall within the range of amino acid numbers 1 to about 748 of the S genes of the FIPV strains or 1 to about 748 of the FECV S genome [SEQ ID NO: 32]. More particularly, peptides falling within the range of about amino acid #94 to about amino acid #223 of the FIPV or FECV S genomes are desirable. In a particularly preferred embodiment, the feline coronavirus S-derived peptides are found to be within the range of amino acid #97–222 of the FIPV or FECV S genomes. In still another embodiment, peptides falling within the range of about amino acids #121 to about amino acid #180 of the FIPV or FECV genome are disclosed.

Peptide fragments of the invention are capable of distinguishing between FIPV and FECV, or different strains of FIPV when used in diagnostic assays, such as enzyme linked immunosorbant assays (ELISA) or Western Blots. These peptides may also be used as antigens to screen cat sera for the presence of antibody or to generate antibodies capable of distinguishing between FIPV and FECV, or different strains of FIPV.

In another aspect, the present invention provides nucleotide sequences from FIPV and FECV within the regions of nucleotide #1 to about #4365 and #1 to about #2246, which encode the above-described peptides, or which flank the above-described peptide-encoding sequences. These nucleotide sequences are capable of distinguishing between the FIPV and FECV S genomes, when they are used in diagnostic assays as PCR primers or hybridization probes.

Another aspect of the invention provides novel recombinant FIPV or FECV S fusion proteins. The feline coronavirus S-derived peptides of the present invention may be fused with a selected protein which confers a desired advantage upon recombinant expression of the S peptide. For example, the fusion partner may be a protein which is highly expressed in the desired host cell system or which is characterized by a high degree of secretion. The fusion partner may also be a signal sequence or a sequence which enhances the stability of the S-derived peptide in a selected host cell system. In one embodiment of this aspect, peptides derived from the S gene of feline coronavirus are fused with the N-terminal 52 amino acids of galactokinase (GalK).

In another aspect the present invention provides a diagnostic reagent composition which comprises an FIPV S-derived peptide or fusion protein of the present invention, optionally associated with a detectable label. Such diagnostic reagents may be used to assay for the presence of FIPV or FECV in cats using standard assay formats.

In a similar aspect the present invention provides a diagnostic reagent composition which comprises a nucleotide sequence encoding or flanking an FIPV S-derived peptide or fusion protein of the present invention, the DNA sequence being optionally associated with a detectable label. Such diagnostic reagents may be used to assay for the presence of FIPV or FECV in cats in hybridization assays or in the PCR technique.

In still another aspect of the present invention, the S-derived peptides and/or the S-derived fusion proteins may be utilized as the active component in vaccines to protect animals against infection with FIPV or FECV. A vaccine composition includes an effective amount of an FIPV or FECV S-derived peptide or fusion protein of the present invention capable of stimulating immunity against one or more virulent feline coronaviruses and a carrier suitable for internal administration. Additionally, characterization of the immune response to these peptides and proteins may also suggest other region(s) of the FIPV or FECV sequences which should be included in vaccines.

In yet a further aspect, the present invention provides a pharmaceutical composition for the treatment of FIPV or FECV infection comprising a therapeutically effective amount of a FIPV or FECV S-derived peptide or fusion protein of the invention and a pharmaceutically effective carrier.

In still another aspect, the invention provides a diagnostic kit which may be used by veterinarians to identify cats which are uninfected or which have been exposed to FECV or native FIPV. The kit will also allow the identification of cats which have been vaccinated against these diseases. Such a kit may also allow one to distinguish between different strains of FIPV, or to identify cats at advanced stages of FIPV infection. The kit may be comprised of PCR primers of this invention selected from the S gene nucleotide sequences; a selected FIPV S-derived peptide or fusion protein; primers, peptides and fusion proteins of related or similar viruses, and primers, peptides and fusion protein-encoding regions from a "consensus" sequence as described below.

In a further aspect, the invention provides a method of using the PCR S-derived primers and/or the S-derived peptides and fusion proteins of this invention to identify previously exposed and naive cats, as well as to differentiate exposure to FIPV from exposure to other related coronaviruses. Another diagnostic method of this invention permits the use of an S-gene derived peptide in an ELISA to detect an antibody to the virus in cat sera.

Another aspect of this invention involves a method of vaccinating an animal against infection with FIPV by administering an effective vaccinal amount of an S-derived peptide or an S-derived fusion protein of this invention.

In still a further aspect, the invention provides a method for treating FIPV infection by administering to an animal a pharmaceutical composition of the present invention.

Still another aspect of this invention is an antibody directed to FIPV or FECV or related coronavirus epitopes, which antibody is capable of distinguishing between these viruses. These antibodies are generated by employing a peptide or fusion protein of the present invention as an antigen. Such antibodies may also be employed as diagnostic or therapeutic reagents, and may be optionally attached to a detectable label or toxin or other therapeutic compound.

Other aspects and advantages of the present invention are described further in the following detailed description of embodiments of the present invention.

BRIEF DESCRIPTION OF THE DRAWINGS

FIG. 3 (3-1 to 3-2) illustrates the nucleotide [SEQ ID NO: 19] and amino acid sequence (SEQ ID NO: 20) of the PCR expression clone AR58-3.

FIG. 4 (4-1 to 4-12) illustrates the S gene nucleotide and amino acid sequences of DF2 FIPV [SEQ ID NO: 21 and 22]. Also illustrated is a fragment of the sequences of DF2-HP [SEQ ID NO: 23 and 24] which are identical to the sequences of DF2 FIPV (to the extent DF2 FIPV has been sequenced) with the exception of the nucleotide changes above and amino acid differences below the DF2-HP sequences.

FIG. 5 (5-1to 5-12) illustrates a fragment of the S gene TS-BP nucleotide sequence (SEQ ID NO: 27] and amino acid sequence [SEQ ID NO: 28] by indicating the positions where the sequences differ from the sequences of TS FIPV [SEQ ID NO: 25 and 26]. The entire TS FIPV S gene sequence is provided.

FIG. 6 illustrates a fragment of the S gene nucleotide and amino acid sequences [SEQ ID NO: 29 and 30] of TN406.

FIG. 7 (7-1 to 7-12) illustrates the complete nucleotide and amino acid sequences [SEQ ID NO: 31 and 32] of FECV S gene.

FIG. 8 illustrates fragments of the nucleotide and amino acid sequences of the UCD-2 S gene.

FIG. 9 (9-1 to 9-8) illustrates the nucleotide and amino acid sequences (SEQ ID NO: 33 and 34) of a consensus partial S gene sequence.

DETAILED DESCRIPTION OF THE INVENTION

Figure 1:
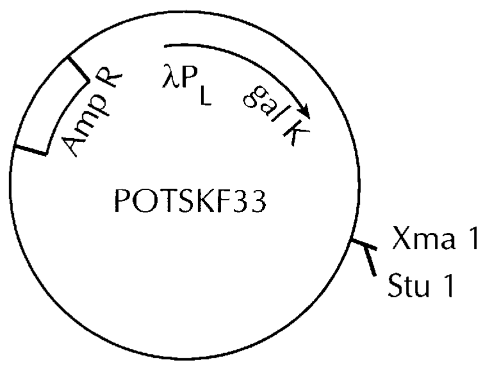
FIG. 1 is a schematic diagram of the pOTSKF33 bacterial expression vector.

The present invention provides novel compositions useful for FIPV and FECV diagnostic, vaccinal and therapeutic compositions as well as methods for using these compositions in the diagnosis, prophylaxis and treatment of FIP.

It is presently preferred to use the FIPV or FECV S gene or a portion thereof to construct the peptides useful in this invention. However, the S gene from other coronaviruses may be useful in a similar manner as that disclosed in this invention.

The S gene sequence from the published FIPV WT WSU 1146 strain was analyzed by computer analysis, as described in detail in Example 1, resulting in the prediction of antigenic regions which may differentiate virus strains. The inventors predicted that differences between various strains of FIPV and its sister virus, FECV, would be localized within the amino terminal half of the peplomer sequence. Using discrete portions of the S protein that differ in amino acid sequence, polypeptides could be used to generate reagents that discriminate between the serologically similar viruses.

The examples below specifically refer to the published FIPV strain WT WSU 1146 [DeGroot et al, *J. Gen. Virol.,* 68:2639–2646 (1987)], and to newly identified sequences from strains WT DF2, TS-FIPV, WT TN406, WT UCD-1, and WT UCD-2 and to vaccine strains WT FIPV DF2 high passage (DF2-HP) and TS FIPV DF2 back passage (DF2-BP). WT FIPV DF2-HP was derived from WT DF2 by 99 serial passes in tissue culture. The DF2-HP was then mutagenized by exposure to ultraviolet light to generate the TS FIPV virus. To determine the stability of the TS FIPV virus, it was then passaged 5 times in cats and tissue culture to generate the TS-BP FIPV strain. Particularly disclosed are the complete nucleotide and amino acid sequences of the FECV S gene. DNA and amino acid sequences of a putative consensus sequence are also useful in providing nucleotide and peptide sequences of this invention. The present invention is not limited to the particular FIPV strains employed in the examples. According to the teachings of this invention, the same analysis may be made from other virulent or avirulent feline or other coronavirus strains with similar results.

The amino acid and nucleotide numbers of the S-derived peptides and DNA sequences described herein from unpublished or newly identified FIPV or FIPV-related virus strains correspond to the numbering system of the published WT WSU 1146 S gene. However, as indicated in the viral sequences appearing in FIGS. 3–8 and by the formation of the consensus sequence of FIG. 9 and as described in detail in Example 12, the sequences in the other viruses are somewhat longer or shorter than the identified homologous WT WSU 1146 peptides, and the actual amino acid numbering of homologous WT WSU 1146 sequence regions in these previously unknown virus sequences differ. The consensus sequence of FIG. 9 is an artificial sequence which includes the most commonly employed amino acid in each position among the FIPV sequences WT WSU 1146, WT DF2, DF2-HP, TS, TS-BP, WT TN-406, and FECV.

The DNA and protein sequences from which regions suitable as candidates for differentiating between FIPV strains and FECV have been identified and are present in the variable N-terminal half of the S gene of both the FIPV strains, the consensus sequence, and FECV. DNA and protein sequences from the carboxy half of the S gene are also identified as possible vaccinal components. All of these regions may be cloned and expressed by conventional means. The location of polymerase chain reaction (PCR) primers can be shifted to amplify sequences spanning the entire S gene, and/or discrete portions of the gene.

In the practice of this invention, oligonucleotide sequences were designed to prime cDNA synthesis at specific sites within the FIPV S gene. Oligonucleotide primers specific for the DNA sequence of the FIPV S gene were designed as described in detail in Example 2. Table II below specifically identifies the 5' and 3' FIPV S oligonucleotide primers [SEQ ID NOS: 1–9 and 10–18, respectively] by nucleotide sequence and portion of S gene amino acid sequence covered. In addition to providing nucleotide sequences spanning the amino acid sequence regions of the S gene, the primers specifically identified in Table II [SEQ ID NOS: 1–18] also contain sequences for introducing a feline coronavirus S gene fragment in a specific orientation into a selected expression vector to produce fusion proteins of the invention.

These same primers, as well as the below-described optimized conditions for the PCR amplification of fragments from feline coronavirus RNA, e.g., the primers of Table II below [SEQ ID NOS: 1–18], may also be utilized as reagents in a diagnostic method employing the PCR technique to identify the presence of an FIPV or FIPV-like virus.

These primers were synthesized by the phosphoramidite method and gel purified prior to use. The primers were then used in the technique of polymerase chain reaction (PCR) analysis [see, e.g., Arnheim et al, *Chem. & Eng. News,* pages 36–47 (Oct. 1, 1990)], which reference is incorporated herein by reference. The PCR technique is known to those of skill in the art of genetic engineering and is described in detail in Example 3. The PCR technique may be used to generate additional fragments representing discrete regions of the FIPV and FECV peplomer gene. Thus this technique permits the isolation, identification and amplification of FIPV and FECV sequences which represent areas of homology or heterogeneity among significant strains of feline coronaviruses. Such DNA sequences or fragments thereof are useful in both diagnosis and therapy of infected animals.

The identification of heterogenous gene sequences provides reagents useful in diagnostic assays to detect and distinguish the presence of specific viruses from each other, e.g., to distinguish one feline coronavirus from another or one species of coronavirus from another by means of conventional assay formats.

PCR analysis of related feline coronaviruses also generates information on regions of homology or non-homology among virus strains with different disease-causing characteristics. Information obtained by the PCR mapping of the feline coronavirus and other related viruses, such as porcine transmissible gastroenteritis virus (TGEV) [Jacobs et al, *Virus Res.,* 8:363–371 (1987)] canine CCV and human 229E, is useful in formulating vaccines effective against other closely related coronaviruses or to more than one FIPV strain. For example, exemplary vaccines may contain effective amounts of the above-described homologous amplified sequences, possibly effective against more than one species of coronavirus.

Briefly described, PCR employs two oligon cleotide primers which are complementary to the opposite strands of a double stranded nucleic acid of interest which strands are oriented such that when they are extended by DNA polymerase, synthesis occurs across the region which separates the oligonucleotides. By repeated cycles of heat denaturation, annealing of the primers to their complementary sequences and extension of the annealed primers with a temperature stable DNA polymerase, millions of copies of the target gene sequence are generated.

The template for the reaction is total RNA, which is isolated from FIPV infected cells. DNA fragments generated by PCR were amplified from cDNA which had been synthesized from this RNA. In initial experiments, the RNA was purified and prepared from the follow strains of FIPV or FIPV-related viruses: WT FIPV DF2, WT FIPV WSU 1146, TS FIPV DF2, WT FIPV UCD-2, WT FIPV TN406, FECV and WT FIPV UCD-1. The RNA and cDNA preparation is described in detail in Example 3 below. Other strains of FIPV or FIPV-related sequences may also provide PCR templates in a similar manner.

The specific regions of the S gene which are amplified by PCR permit differentiation of the feline coronavirus and other related viruses. Mixing and matching the oligonucleotide primers permitted the synthesis of regions representing as little as 105 amino acids of S or as large as 1454 amino acids (complete S). Such primers are identified in Table II below. As described in Example 4 below, PCR primers designed to span amino acid #94–223, produced the following amplified fragments of the FIPV S gene among which are shorter peptides than the spanned region. Presently preferred peptides are those spanning from about amino acid number 94 to about amino acid number 223 of the FIPV S genome the consensus sequence and the FECV genome, and more particularly, from about amino acid number 97 to about amino acid number 222 of the FIPV S genome, the consensus sequence and the FECV genome.

Specific amplified sequences of the FIPV strains, of the invention and FECV include the regions recited below:

From WT DF2, the amplified regions spanned amino acids #1–105, 1–223, 1–362, 1–555, 1–748, 1–1040, 1–1203, 1–1452, 94–223, 94–362, 94–555, 94–748, 94–1040, 94–1203, 94–1452, 213–362, 213–555, 213–748, 213–1040, 213–1203, 213–1452, 352–555, 352–748, 544–748, 544–905, 544–1040, 554–1203, 554–1452, 737–905, 737–1040, 737–1203, 737–1452, 894–1040, 894–1203, 894–1452, 1029–1203, 1029–1452, and 1192–1452.

From TS DF2, the amplified regions spanned amino acids #1–105, 1–223, 1–362, 1–555, 1–748, 1–1040, 1–1203, 94–223, 94–362, 94–555, 94–748, 94–1040, 94–1203, 94–1452, 213–362, 213–555, 213–748, 213–1040, 213–1203, 213–1452, 352–748, 544–748, 544–905, 544–1040, 544–1203, 544–1452, 737–905, 737–1040, 737–1203, 737–1452, 894–1040, 894–1203, 894–1452, 1029–1203, 1029–1452, and 1192–1452.

From FECV, the amplified regions spanned amino acids #1–105, 1–223, 1–362, 94–223, 94–362, 94–555, 94–748, 94–1040, 213–362, 213–748, 352–555, 352–748, 544–748, 544–905, 544–1040, 544–1203, 544–1452, 737–905, 737–1040, 737–1203, 737–1452, 894–1040, 894–1203, 894–1452, 1029–1203, 1029–1452, and 1192–1452.

From WT WSU 1146, the amplified regions spanned amino acids #1–105, 1–223, 1–362, 1–555, 94–223, 94–362, 94–555, 94–748, 213–362, 213–748, 352–555, 352–748, 544–748, 544–905, 544–1040, 544–1203, 737–905, 737–1040, 737–1203, 894–1040, 894–1203, 894–1452, 1029–1203, 1029–1452, and 1192–1452.

From WT UCD-1, the amplified regions spanned amino acids #94–223, 94–362, 352–555, 352–748, 544–748, 737–905, 737–1040, 737–1203, 894–1040, 894–1203, 1029–1203, 1029–1452, and 1192–1452.

From WT TN406, the amplified region spanned amino acids #94–223. From WT UCD-4, the amplified region spanned amino acids #94–223.

Many of these fragments have been cloned and expressed as galk fusion proteins. They are listed in Table IV of Example 5 below.

Similarly, PCR DNA fragments were isolated which show areas of homology or heterogeneity among different strains. For example, the DNA primers flanking amino acid #737–1452 of the FIPV or FECV S genomes provide fragments of predicted size (2168 bp) and DNA primers flanking amino acid #1029–1452 of the FIPV and FECV sequences provide fragments of predicted size (1290 bp). These fragments were amplified from each of the DF2, TS and FECV viral templates. DNA fragments spanning amino acids #1–748 were amplified from DF2, DF2-HP, TS-BP, TS and FECV. A DNA fragment was also amplified for amino acids #94–223 for WT TN406.

Specific fragments which were not amplified, despite appropriate priming events, included the fragments extending from amino acid #1–555 and 3.52–555 for FECV, indicating regions of suspected heterogeneity with the WSU 1146 based primers. These polypeptides or shorter fragments thereof are useful in distinguishing FECV from the FIPV strains.

After identifying roughly homologous regions of the S gene sequence and of the amino acid sequences encoded thereby, the sequences were compared to determine their percent homologies. In general, nucleic acid and amino acid homologies of less than 95% may indicate that certain regions of the virus may be useful as a diagnostic capable of distinguishing between the apathogenic FECV and the virulent FIPV. The following Table I illustrates the homologies between the S gene regions of the FIPV strains indicated and FECV, indicating the FECV and the FIP viruses were sufficiently different to supply useful differentiating sequences for diagnostic and therapeutic use.

Homologies reported in the Table I are in percent and numbers of mismatching/nonmatching base pairs or amino acids are in parentheses. AA (I) represents perfect match amino acid homology. AA (S) represents similarity match amino acid homology based on the rules of M. O.Dayhoff, "Sequence and Atlas of Protein Structure", National Biomedical Research Foundation, Silver Spring, Md. (1968).

TABLE I

| Strain 1 | Strain 2 | Nucleic Acid | AA (I) | AA (S) |
|---|---|---|---|---|
| WSU | FECV | 92.9 (159) | 93.0 (52) | 93.0 (52) |
| DF2 | FECV | 93.1 (154) | 93.3 (50) | 93.3 (50) |
| DF2-HP | FECV | 93.0 (158) | 93.3 (50) | 93.3 (50) |
| TS | FECV | 92.9 (160) | 92.9 (53) | 92.9 (53) |
| TS-BP | FECV | 93.1 (156) | 93.3 (50) | 93.3 (50) |
| TN406 | FECV | 90.0 (37) | 86.1 (17) | 86.1 (17) |

Comparison of the nucleotide and amino acid sequences of the six FIP coronaviruses WT DF2, WT WSU 1146, DF2-HP, TS, TS-BP, and WT TN406 to FECV and to the Consensus Sequence (FIG. 9) revealed that overall, FECV shares only ~93.0% homology with the FIPV strains. Greater than 50 amino acids differ between FECV and the illustrated FIPV strains in the first 748 amino acids of the S gene. Some of these changes occur in clusters in regions of the FECV sequence which differ from homologous regions of the FIPV sequences. Such clustered regions represent sites for differentiation of the virus and are desirable as diagnostic reagents capable of distinguishing between FIPV and FECV or as therapeutic or vaccinal agents. Corresponding regions of the FIPV strains or consensus sequence, i.e., regions demonstrating clustered amino acid differences from FECV or other strains of FIPV, may be employed in the same way.

The nucleotide sequence of the S gene of FECV provides desirable sequences for hybridization probes and PCR primers, e.g., the sequence between base pairs 1–1080. Corresponding amino acid sequences provide peptides useful in ELISA or Western assay or as antigens for the screening of sera or development of antibodies, e.g., the sequence between amino acids 1–360. Such probes, primers, antigens and antibodies would react positively with tissue or serum samples of cats infected with FECV, but negatively with cats infected with a FIPV strain.

In particular, the following regions of FECV appear particularly suitable for the generation of peptide fragments and DNA sequences for such purposes. Corresponding regions of the FIPV strains and consensus sequence may also be useful for the same purposes.

These FECV regions are: amino acid residues 18–26 [SEQ ID NO: 36], 46–53 [SEQ ID NO: 38], 73–78 [SEQ ID NO: 40], 124–174 [SEQ ID NO: 42], 145–150 [SEQ ID NO: 44], 138–159 [SEQ ID NO: 46], 143–150 [SEQ ID NO: 48], 200–205 [SEQ ID NO: 50], and 529–536 [SEQ ID NO: 52] and corresponding nucleotide fragments 52–78 [SEQ ID NO: 35], 136–159 [SEQ ID NO: 37], 214–231 [SEQ ID NO: 39], 370–519 [SEQ ID NO: 41], 433–450 [SEQ ID NO: 43], 412–477 [SEQ ID NO: 45], 427–450 [SEQ ID NO: 47], 598–615 [SEQ ID NO: 49], and 1585–1608 [SEQ ID NO: 51].

Smaller peptide fragments in these regions or larger fragments containing these regions may be employed in biological and serological assays, e.g. at least 10 amino acids in length. Preferably, a sequence of at least 7 or 8 different amino acids in a peptide of 15 amino acids is needed for most conventional veterinarian performed assays (see, Posthumus et al, *J. Virol.,* 68:2639–2646 (1987)]. Of course, genetic techniques are capable of detecting a single amino acid change in a small peptide.

Smaller or larger DNA fragments in these regions may also be employed as PCR primers or hybridization probes. Desirably PCR primer sequences are between 15 to 30 bases in length, with an intervening sequence of at least 100 bases to as large as 1500 bases there between, according to conventional PCR technology. However, it is possible that larger or smaller sequence lengths may be useful based upon modifications to the PCR technology.

In general, in order to achieve satisfactory discrimination, a probe made up of one or more of these sequences would consist of between 15 and 50 bases in length based on current technology. However, shorter regions may be used if they are bound to a carrier. Suitable carriers include ovalbumin, keyhole limpet hemocyanin, bovine serum albumin, sepharose beads and polydextran beads.

The PCR amplification technique itself may be used as a diagnostic tool. Using protocols similar to those used for forensic purposes, tissue or blood samples from a cat suspected to be infected with FIPV would be subjected to PCR amplification with a selected FIPV-specific set of primers, such as those DNA sequences disclosed above and in Table II. Amplification of DNA would correlate to the presence of FIPV. Absence of FIPV in the sample would result in no amplification. Similarly, the selection of specific sets of S primers would allow the identification of a particular strain of FIPV as well. Similar results may be obtained to diagnose FECV using FECV primers to other regions of heterogeneity vs. FIPV strains, as indicated above.

When used as diagnostic reagents, the primers, probes and peptides of this invention may be optionally associated with detectable labels or label systems known to those skilled in the art. The diagnostic assays may be any conventionally employed assay, e.g., a sandwich ELISA assay, a Western blot, a Southern blot and the like.

It is anticipated that PCR primers, hybridization probes and, alternatively peptide diagnostic reagents, could be similarly designed to distinguish CCV and TGEV from FIPV. For example, the PCR amplification-of nucleic acid from a sample tissue or biological fluid from an animal suspected of infection using primers specific for regions of viral gene sequences may identify or rule out the presence of a specific virus. Thus, appropriate treatments may be selected for the infected animal.

The nucleotide and peptide fragments of the S genes of feline coronaviruses according to this invention may be readily synthesized by conventional means, e.g., Merrifield synthesis [Merrifield, *J.A.C.S,* 85:2149–2154 (1963)]. Alternatively, they may be produced by recombinant methods. Cloning procedures are conventional and as described by T. Maniatis et al, *Molecular Cloning (A Laboratory Manuall,* Cold Spring Harbor Laboratory (1982).

A selected PCR-derived fragment of this invention representing a portion of the S gene sequence, as determined by a fragment produced during PCR, is cloned into a selected expression vector. Vectors for use in the method of producing S gene proteins comprise a novel S gene fragment DNA sequence of the invention and selected regulatory sequences in operative association with the DNA coding sequence, capable of directing the replication and expression of the S-derived peptide in a selected host cell.

The above-identified S gene nucleotide sequences, proteins and peptide fragments are also desirably produced in the form of fusion proteins. Such fusion proteins may be produced synthetically as described above for the peptide fragments themselves. However, to facilitate the production of fusion proteins of this invention, recombinant methods are preferred. The selected primer sets used in the PCR reaction may be designed to produce PCR amplified fragments containing restriction endonuclease cleavage site sequences for introduction of a feline coronavirus S gene fragment in a specific orientation into a selected expression vector to produce fusion proteins of the invention. The vector may contain a desired protein or fragment thereof to which the S gene fragment is fused in frame to produce a fusion protein.

Proteins or peptides may be selected to form fusion proteins with the selected S gene sequence based on a number of considerations. For example, a fusion partner for the S-derived fragment may be selected because it is highly expressed in the selected host cell system and may confer high expression levels on the S-derived sequence fused to it. As described in detail in Example 5 below, a selected fusion protein of this invention is produced by fusing the selected S gene sequence in frame to 52 amino acids of the bacterial enzyme, galactokinase (galK), which catalyzes the first step of galactose metabolism in bacteria. The sequence of this enzyme has been manipulated to permit insertion of foreign genes and the construction of fusion proteins. GalK is highly expressed in *E. coli* expression systems.

Similarly, the fusion partner may be a preferred signal sequence, a sequence which is characterized by enhanced secretion in a selected host cell system, or a sequence which enhances the stability of the S-derived peptide. Some other exemplary fusion partners which may be selected in place of galactokinase include, without limitation, ubiquitin and a mating factor for yeast expression systems, and beta-galactosidase and influenza NS-1 protein for bacterial systems. One of skill in the art can readily select an appropriate fusion partner for a selected expression system. The present invention is not limited to the use of any particular fusion partner.

Figure 2:
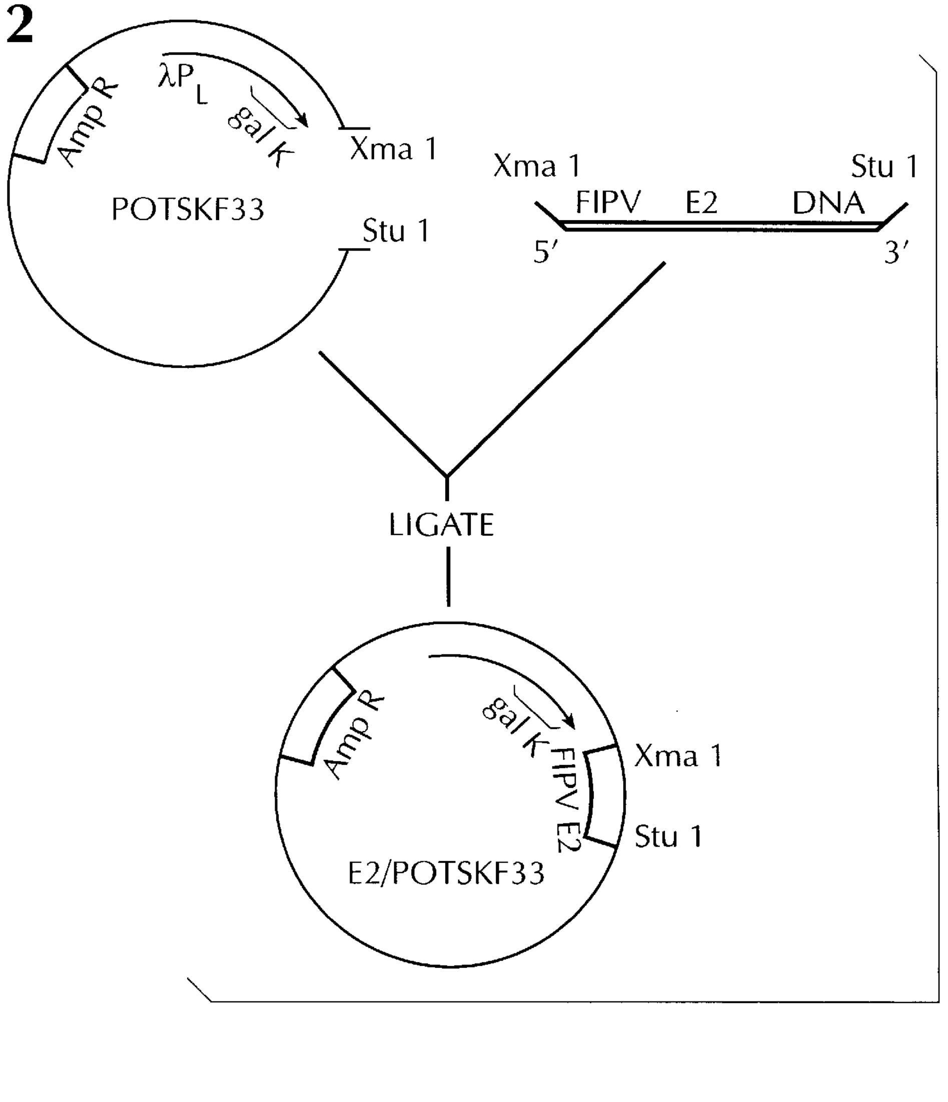
FIG. 2 illustrates a plasmid containing a PCR-amplified fragment cloned into the XmaI-StuI sites of pOTSKF33.

Vectors of the invention may be designed for expression of S gene peptides or fusion proteins in bacterial, mammalian, fungal or insect cells or in selected viruses. Suitable vectors are known to one skilled in the art by resort to known publications or suppliers. The vector employed in the construction of the fusion proteins of the examples below is a bacterial pBR322-derived expression vector, pOTSKF33 (see FIG. 1 and Example 5). Plasmid pOTSKF33 is a derivative of pBR322 [Bethesda Research Laboratories] and carries regulatory signals from bacteriophage lambda. Phage regulatory information was chosen because of its high efficiency and its ability to be regulated. The system provides a promoter which can be controlled ($\lambda P_L$), antitermination mechanisms to ensure efficient transcription across any gene insert, high vector stability, antibiotic selection, and flexible sites for insertion of any gene downstream of the regulatory sequences. The S gene sequence PCR fragments were engineered so that cloning into the unique restriction sites of pOTSKF33 (using XmaI and StuI) results in the construction of galactokinase/FIPV S peplomer fusion genes. One such fusion gene is illustrated in FIG. 2.

The resulting DNA molecules or vectors containing the sequences encoding the feline coronavirus S-derived peptides or fusion genes are then introduced into host cells and expression of the heterologous protein induced. Suitable cells or cell lines for use in expressing the S-derived peptides or fusion proteins of this invention are presently preferred to be bacterial cells. For example, the various strains of *E. coli* (e.g., HB101, MC1061) are well-known as host cells in the field of biotechnology. Various strains of *B. subtilis,* Pseudomonas, other bacilli and the like may also be employed in this method.

It is also anticipated that mammalian cells, such as Chinese hamster ovary cells (CHO) or COS-1 cells, may be used in the expression of the proteins, peptides and fusion proteins of this invention. The selection of other suitable mammalian host cells and methods for transformation, culture, amplification, screening and product production and purification are known in the art. See, e.g., Gething and Sambrook, *Nature,* 293:620–625 (1981), or alternatively, Kaufman et al, *Mol. Cell. Biol.,* 5(7):1750–1759 (1985) or Howley et al, U.S. Pat. No. 4,419,446.

Similarly many strains of yeast, or other fungal cells known to those skilled in the art are also available as host cells for expression of the proteins, peptides and fusion proteins of the present invention. Yeast expression vectors are constructed employing yeast regulatory sequences to express the DNA encoding a protein, peptide or fusion protein in yeast cells so that they yield secreted extracellular active inhibitor. [See, e.g., procedures described in published PCT application WO 86/00639 and European patent application EP 123,289. Insect cells are also known host cells used in the expression of recombinant proteins and may be employed as host cells herein. Additional expression systems may include the known viral expression systems, e.g., vaccinia, fowlpox, swine pox. It is understood additionally, that the design of the expression vector will depend on the choice of host cell. A variety of suitable expression systems are known to those skilled in the art.

After the transformed host cells are cultured for suitable times and under suitable culture conditions known to those skilled in the art, the cells may be lysed. It may also be possible depending on the construct employed, that the recombinant proteins are secreted extracellularly and obtained from the culture medium. Cell lysates or culture medium are then screened for the presence of S-derived peptides or fusion proteins which are recognized by antibodies, preferably MAbs, to a peptide antigenic site from FIPV, FECV or consensus sequence, and in the case of a fusion protein, to the fusion partner, e.g., *E. coli* galactokinase.

The crude cell lysates containing the S-derived peptides or fusion polypeptides can be used directly as vaccinal components, therapeutic compositions or diagnostic reagents. Alternatively, the S-derived peptides or fusion proteins can be purified from the crude lysate or medium by conventional means. For example, galactokinase/FIPV S fusion polypeptides can be purified from bacterial lysates by affinity chromatography. Briefly, columns are prepared with monoclonal antibodies to galactokinase. The selected MAbs recognize epitopes within the first 52 amino acids of the enzyme. Bacterial lysates containing the fusion proteins are adsorbed onto the affinity matrix forming antigen-antibody complexes as the material moves through the column. After washing the column, the bound galK/S peplomer (FIPV, FECV or consensus) fusion protein is eluted by treatment with acid, base or chaotropic agents. The purified S-derived peptide or fusion protein is then more desirable for use as a vaccine component or a diagnostic reagent.

Thus the expression of the PCR amplified S gene sequence or S gene/fusion partner DNA sequences in the host cells, e.g., the galK/FIPV or FECV S fragments produced in bacterial cells, produces recombinant proteins which may be employed in diagnostic assays or as components of therapeutic and vaccinal compositions. As one example, the purified recombinant fusion protein, 58-3 (SEQ ID NOS: 19 and 20, nucleic acid and amino acid sequences, respectively), prepared according to the present invention contains a feline coronavirus S gene portion corresponding to amino acids 97 to 223 of TS FIPV. In the same manner fusion proteins may be formed with FECV amino acid sequences or amino acid sequences of the other FIP strains disclosed herein.

The recombinant proteins of this invention may thus be incorporated in a vaccine composition. Such a vaccine composition may contain an immunogenic amount of one or more selected S-derived peptides, proteins, e.g., encoded by the complete S gene sequence of FECV, or fusion proteins prepared according to the method of the present invention, together with a carrier suitable for parenteral administration as a vaccine composition for prophylactic treatment of FIPV infections. It is preferable that the recombinant protein employed in the vaccine composition contains an S gene sequence which induces protective immune responses against more than one strain of FIPV.

It is additionally desirable that the S-derived peptides, proteins or fusion proteins of this invention be employed in a vaccine composition which includes additional antigens, e.g. other coronaviruses or other pathogens in general. For example, an S-derived peptide, protein or fusion protein of the present invention may be employed as an additional antigen in the temperature sensitive FIPV vaccine described in detail in co-owned, co-pending U.S. patent application Ser. No. 07/428,796 filed Oct. 30, 1989 [SKB 14393] now abandoned, incorporated by reference herein. Alternatively, the peptides, proteins and fusion proteins of this invention may also be included in other feline vaccine compositions, e.g., a vaccine for feline leukemia.

The preparation of a pharmaceutically acceptable vaccine composition, having appropriate pH isotonicity, stability and other conventional characteristics is within the skill of the art. Thus such vaccines may optimally contain other conventional components, such as adjuvants and/or carriers, e.g. aqueous suspensions of aluminum and magnesium hydroxides, liposomes and the like.

The vaccine composition may be employed to vaccinate naive animals against the clinical symptoms associated with FIP. The vaccines according to the present invention can be administered by an appropriate route, e.g., by the oral, intranasal, subcutaneous, intraperitoneal or intramuscular routes. The presently preferred methods of administration are the subcutaneous and intranasal routes.

The amount of the S-derived peptide, protein or fusion protein of the invention present in each vaccine dose is selected with regard to consideration of the animal's age, weight, sex, general physical condition and the like. The amount required to induce an immunoprotective response in the animal without significant adverse side effects may vary depending upon the recombinant protein employed as immunogen and the optional presence of an adjuvant. Generally, it is expected that each dose will comprise 0.1–1000 micrograms of protein per mL, and preferably 0.1–100 micrograms per mL of a sterile solution of an immunogenic amount of a recombinant protein or peptide of this invention. Initial doses may be optionally followed by repeated boosts, where desirable. The presently preferred vaccine composition comprises at least 1–10 fusion proteins per mL. Another vaccine agent of the present invention is an anti-sense RNA sequence generated to a sequence of FIGS. 4–8. This sequence may easily be generated synthetically by one of skill in the art either synthetically or recombinantly. Under appropriate delivery, such an anti-sense RNA sequence upon administration to an infected animal should be capable of binding to the RNA of the virus, thereby preventing viral replication in the cell.

The invention also provides a pharmaceutical composition comprising S-derived peptides, proteins or fusion proteins prepared according to the present invention and a pharmaceutically effective carrier. Suitable pharmaceutically effective carriers for internal administration are known to those skilled in the art. One selected carrier is sterile saline. The pharmaceutical composition can be adapted for administration by any appropriate route, but is designed preferentially for administration by injection or intranasal administration.

The S-derived proteins, fusion proteins, or peptide fragments, as well as the PCR primers produced as described above, may also be employed in diagnostic assays which rely on recombinant derived protein immunogens as targets for sera recognition. For example, the invention provides a method of using peptides derived from the S gene of feline coronavirus, optionally fused with, e.g., the N-terminal 52 amino acids of galactokinase, as diagnostic agents useful for identifying previously exposed and naive cats, as well as for differentiating exposure to FIPV from other related coronaviruses. Other galK/FIPV S peptides or fusion proteins which show differential reactivity to FECV and FIPV sera may also be useful as FIPV-specific reagents in ELISA-based screening assays to detect FIPV exposure in cats. Similarly, an S-derived peptide or fusion protein which contained epitopes recognized only by sera from FECV infected cats or by sera from FIPV positive cats could be employed to distinguish or differentiate among coronavirus infections.

As one assay format, the reactivity of affinity purified FIPV or FECV S proteins, peptides or fusion polypeptides, e.g., galK/S fragments, to feline biological fluids or cells can be assayed by Western blot. The assay is preferably employed on sera, but may also be adapted to be performed on other appropriate fluids or cells, for example, macrophages or white blood cells. In the Western blot technique, the purified. protein, separated by a preparative gel, is transferred to nitrocellulose and cut into multiple strips. The strips are then probed with cat sera from uninfected or infected cats. Binding of the cat sera to the protein is detected by incubation with alkaline phosphatase tagged goat anti-cat IgG followed by the enzyme substrate BCIP/NBT. Color development is stopped by washing the strip in water.

Western blot screening of cat sera samples has been performed with the purified recombinant fusion protein, 58-3 (SEQ ID NO:20), prepared according to the present invention and as described in detail in Examples 5 through 7. The feline coronavirus S gene portion of this recombinant protein is obtained from TS FIPV and corresponds to amino acids 97 to 223 of the published WSU 1146 strain. When screened with a battery of cat sera, only sera of those cats which were sick and/or dying with DF2 or WSU 1146 FIPV reacted with the 58-3 polypeptide (SEQ ID NO: 20). Healthy cats did not react to this peptide nor did cats which were challenged with the nonvirulent FECV coronavirus strain. Other peptides of this invention may be employed similarly to distinguish between FIPV strains and FECV, or among different strains of FIPV.

Fusion protein 58-3 (SEQ ID NO: 20) may also be used in an ELISA based assay for detecting FIPV disease. Other S derived peptides or fusion proteins which show differential reactivity to FECV and FIPV sera may also be useful as FIPV-specific reagents in ELISA-based screening assays to detect FIPV exposure in cats.

A typical ELISA protocol would involve the adherence of antigen (e.g., a recombinant galK/S fusion protein) to the well of a 96-well tray. The serum to be tested is then added. If the serum contains antibody to the antigen, it will bind. Specificity of the reaction is determined by the antigen absorbed to the plate. With the 58-3 galK/FIPV S fusion protein (SEQ ID NO: 20), only sera from those cats sick or dying from FIPV would bind to the plate; sera from naive or healthy virus-exposed cats would not bind.

Similarly, an S-derived protein, peptide or fusion protein which contained epitopes recognized only by sera from FECV infected cats or by sera from FIPV positive cats could be employed to distinguish coronavirus infections. After the primary antibody is bound, an enzyme-labelled antibody directed against the globulin of the animal whose serum is tested is added. Substrate is then added. The enzyme linked to antibody bound to the well will convert the substrate to a visible form. The amount of color measured is proportional to the amount of antibody in the test material. In this manner, cats previously infected with FIPV can be identified and treated, or cats naive to the virus can be protected by vaccination.

The present invention also encompasses the development of an antibody to one of the above identified amino acid residue regions of FECV or to fusion proteins carrying such a region, which region does not react with other coronavirus, e.g. FIPV. In one embodiment, the antibody is capable of identifying or binding to an FECV antigenic site encoded by all or a portion of the DNA sequences identified below in FIGS. 3–8. Such an antibody may be used in a diagnostic screening test or as therapeutic agents.

Antibodies to peptides of the regions identified above or to other regions capable of distinguishing between FIPV and FECV for use in the assays of this invention may be polyclonal. However, it is desirable for purposes of increased target specificity to utilize monoclonal antibodies (MAbs), both in the assays of this invention and as potential therapeutic and prophylactic agents. Additionally, synthetically designed monoclonal antibodies may be made by known genetic engineering techniques [W. D. Huse et al, *Science,* 246:1275–1281 (1989)] and employed in the methods described herein. For purposes of simplicity the term MAb(s) will be used throughout this specification; however, it should be understood that certain polyclonal antibodies, particularly high titer polyclonal antibodies and recombinant antibodies, may also be employed.

A MAb may be generated by the well-known Kohler and Milstein techniques and modifications thereof and directed to one or more of the amino acid residue regions identified above, or to other FECV-encoded peptides or epitopes containing differences between itself and FIPV, such as those identified in Example 12 below. For example, such a portion of the FECV sequence encoding an antigenic site, which differs from that of FIPV, may be presented as an antigen in conventional techniques for developing MAbs. A cell line secreting an antibody which recognizes an epitope of FECV only, not on FIPV or any other coronavirus, may then be identified for this use. One of skill in the art may generate any number of MAbs by using fragments of the amino acid residue regions identified herein as an immunogen and employing these teachings.

For diagnostic purposes, the antibodies (as well as the diagnostic probes) may be associated with individual labels, and where more than one antibody is employed in a diagnostic method, the labels are desirably interactive to produce a detectable signal. Most desirably, the label is detectable visually, e.g. calorimetrically. Detectable labels for attachment to antibodies useful in the diagnostic assays of this invention may also be easily selected by one skilled in the art of diagnostic assays. Labels detectable visually are preferred for use in clinical applications due to the rapidity of the signal and its easy readability. For calorimetric detection, a variety of enzyme systems have been described in the art which will operate appropriately. Colorimetric enzyme systems include, e.g., horseradish peroxidase (HRP) or alkaline phosphatase (AP). Other proximal enzyme systems are known to those of skill in the art, including hexokinase in conjunction with glucose-6-phosphate dehydrogenase. Also, bioluminescence or chemiluminescence can be detected using, respectively, NAD oxidoreductase with luciferase and substrates NADH and FMN or peroxidase with luminol and substrate peroxide. Other conventional label systems that may be employed include fluorescent compounds, radioactive compounds or elements, or immunoelectrodes. These and other appropriate label systems and methods for coupling them to antibodies or peptides are known to those of skill in the art.

Antibodies specific for epitopes on FIPV, which are not capable of binding FECV, or alternatively which are specific to epitopes on virulent strains of FIPV but not avirulent strains, may also be used therapeutically as targeting agents to deliver virus-toxic or infected cell-toxic agents to infected cells. Rather than being associated with labels for diagnostic uses, a therapeutic agent employs the antibody linked to an agent or ligand capable of disabling the replicating mechanism of the virus or of destroying the virally-infected cell. The identity of the toxic ligand does not limit the present invention. It is expected that preferred antibodies to peptides encoded by the sequences identified herein may be screened for the ability to internalize into the infected cell and deliver the ligand into the cell.

The assay methods, PCR primers, S-derived proteins, peptides and fusion proteins and antibodies described herein may be efficiently utilized in the assembly of a diagnostic kit, which may be used by veterinarians. The kit would be useful in distinguishing between native FIPV exposed animals and vaccinated animals, as well as non-exposed cats, and between FIPV-infected animals and animals infected with serologically related viruses, such as FECV. Such a diagnostic kit contains the components necessary to practice the assays described above.

Thus, the kit may contain a sufficient amount of at least one fusion protein or at least one S gene protein or peptide or PCR primer pair of this invention, a MAb directed to a first epitope on the FIPV S fragment, (which Mab may be labeled), optional additional components of a detectable labelling system, vials for containing the serum samples, protein samples and the like, and a second mAb conjugated to the second enzyme, which in proximity to the first enzyme, produces a visible product. Other conventional components of such diagnostic kits may also be included.

Alternatively, a kit may contain a selected FIPV S peptide or fusion protein, a Mab directed against a selected FIPV S peptide fragment bound to a solid surface and associated with a first enzyme, a different MAb associated with a second enzyme, and a sufficient amount of the substrate for the first enzyme, which, when added to the serum and MAbs, provides the reactant for the second enzyme, resulting in the color change.

Other known assay formats will indicate the inclusion of additional components for a diagnostic kit according to this invention.

The examples which follow are intended as illustrative only and do not limit the scope of the present invention.

Example 1—Prediction of Potential Antigenic Sites

The computer program developed by Jameson and Wolf, *Cabios,* 4:181–186 (1983) was used to predict potential antigenic sites on the amino acid sequence of the published FIPV WSU 1146 strain (available upon request from the Washington State University). This program was designed to integrate the influence of five major factors that historically have been important in accurate prediction of antigenic sites. Hydrophilicity values are determined according to Hopp and Woods, *Proc. Natl. Acad. Sci. USA,* 78:3824–3828 (1981). Potential surface probabilities are primarily determined by the method of Janin et al, *J. Mol. Biol.,* 125:357–386 (1978), but more recently modified according to Emini et al, *J. Virol.,* 55:836–839 (1985).

Backbone flexibility of the protein was determined as described by Karplus and Shultz, *Naturwissenschaften,* 72:212–213 (1985), while prediction of protein secondary structure was computed by two methods. The algorithm of Chou and Fasman, *Adv. Enzymol.,* 47:145–147 (1978) as modified by Nishikawa *Biochim. Biophys Acta,* 748:285–299 (1983) to include overall probability, was the first method used for secondary structure prediction. In addition, a program developed by Garnier et al, *J. Mol. Biol.,* 120:97–120 (1978) was used in support of Chou-Fasman. The greatest accuracy of secondary structure prediction occurs at points where the two different subroutines are in agreement [Jameson and Wolf, supra].

Each of these factors are computed in concert to produce a summary value, the antigenic index. Output of the program was plotted in linear fashion along the amino acid sequence of the S gene. Analysis of the FIPV S protein was performed on a host computer consisting of a Vax 8800 series (Digital Equipment Corporation) cluster running under the VMS operating system. These programs are available as part of the University of Wisconsin Computer Group (GCG) package environment [Devereux, *Nucleic Acids Research,* 12:387–395 (1984)].

This analysis of the protein sequence using the WT WSU 1146 and TGE coronavirus sequences showed that the FIPV S protein is conserved in the C terminus (⅔ of gene) while variation was concentrated in the N-terminus (⅓ of gene). As predicted by computer analysis, there is little differentiation of the carboxy terminus of the S gene.

Example 2—Oligonucleotide Design

Oligonucleotides were designed to divide the WSU 1146 S gene of 4500 base pairs (1452 amino acids) into approximately 300–500 base pair fragments. Each of these fragments was chosen to encompass one or more major antigenic peaks as determined from the computer analysis described above. Primers were typically 30–40 base pairs in length and included an XmaI restriction site in the upstream (5') primer and a StuI restriction site in the downstream (3') primer. [See Table I below, SEQ ID NOS: 1–18]. These sites were incorporated into the primers to allow for directional, in-frame cloning into the expression vector.

In addition, five additional FIPV matching base pairs were added upstream of each restriction site in order to stabilize the DNA-RNA hybrid and allow amplification to occur efficiently. The oligonucleotides were designed to have a relatively high G-C content (approximately 50% or greater) which provided additional stability to the hybrid.

Primer sequences were compared by computer against the published WSU 1146 sequence to insure that they only primed a specific area, did not form "primer diner" structures with other primers and had no internal secondary structure that could inhibit proper hybridization with the coronavirus RNA/DNA during amplification.

Table II illustrates the FIPV S oligonucleotide primers amplified by PCR technique, 5' through 3' (SEQ ID NOS:

1–18). These primers, designed as described above, were synthesized on an Applied Biosystem Model 380B DNA Synthesizer by the phosphoramidite method, and were gel purified prior to use. At nucleotide #6–11, primer SEQ ID NOS: 1–9 contain an Xma site (CCCGGG) and primer SEQ ID NOS: 10–18 contain an Stu I site.

These primers used for the PCR amplification and resulting fusion proteins of this invention may contain stop codons after fusion with GalK. However, effective binding of the oligonucleotide is important for effective PCR priming, which is not dependent on expression and is therefore unaffected by the presence of a stop codon in the primer.

Nucleotides may be changed at the primer level to eliminate the stop codon problem, and several such changes are indicated in Table II below by asterisks. For example, the second, third, fifth, sixth and ninth 5' primers (SEQ ID NOS: 2, 3, 5 and 9, respectively) may be changed by deleting the nucleotide below the asterisk in each sequence. The fourth and eighth 5' primers (SEQ ID NOS: 4 and 8, respectively) may be changed by adding a T or A, respectively, in front of the nucleotide marked with an asterisk. Additionally, DNA sequence can be added, deleted, or altered as a result of PCR and/or gene expression in bacteria. Therefore, the sequence of all clones must be verified to detect errors in sequence. Any sequence errors can be corrected at the nucleotide level in the expression clones by one of skill in the art with resort to conventional techniques.

The PCR data so far has been obtained using the Table II primers (SEQ ID NOS: 1–18). These same primers were also used in making the expression fusion proteins described in detail below. However, some of the resulting clones were corrected to obtain effective expression data.

TABLE II

| Position (BP) | Position (AA) | Sequence |
|---|---|---|
| 5' (sequence same polarity as published WSU 1146, contains Xma site)<br>5' Xma/3' Xma | | |
| 65–69/70–96(Start)<br>SEQ ID NO:1 | 1–9 | Xma<br>GTGCCCCCGGGTATGATTGTGCTCGTAACTTGCCTCTTG<br>start codon |
| 351–355/356–380<br>SEQ ID NO:2 | 95–104 | *<br>AATACCCGGGGCACTGGTAATGCACGTGGTAAACC |
| 705–709/710–733<br>SEQ ID NO:3 | 213–219 | *<br>GTATTCCCGGGCACGCTCAAGCACTGCTACCTGGG |
| 1121–112/1126–1150<br>SEQ ID NO:4 | 352–360 | *<br>CAGATCCCGGGGTACAATCTGGTATGGGTGCTACAG |
| 1698–1702/1703–1730<br>SEQ ID NO:5 | 544–554 | *<br>GCTTACCCGGGGTGGTTATGGTCAACCCATAGCCTCGAC |
| 2277–2281/2282–2309<br>SEQ ID NO:6 | 737–746 | *<br>TGTGACCCGGGCGCCATGTGATGTAAGCGCACAAGCGGC |
| 2749–2753/2754–2779<br>SEQ ID NO:7 | 894–903 | GCAATCCCGGGGGGTGCCAGACTTGAAAACATGGAGG |
| 3155–3159/3160–3185<br>SEQ ID NO:8 | 1030–1038 | *<br>CATTACCCGGGGGTGCACTTGGTGGTGGCGCCGTGGC |
| 3642–3646/3647–3674<br>SEQ ID NO:9 | 1192–1201 | *<br>TAGGTCCCGGGCTCAGTCTCAGAGATTCGGATTCTGTGG |
| 3' (sequence reverse complement of published WSU 1146, contains Stu I site)<br>5' StuI/3' Stu I | | |
| 385–381/380–356<br>SEQ ID NO:10 | 97–105 | Stu I<br>ATAATAGGCCTGGTTTACCACGTGCATTACCAGTGC |
| 738–734/733–710<br>SEQ ID NO:11 | 213–223 | GTATTAGGCCTCCCAGGTAGCAGTGCTTGAGCGTG |
| 1155–1151/1150–1126<br>SEQ ID NO:12 | 353–362 | AAATAAGGCCTCTGTAGCACCCATACCAGATTGTAC |
| 1735–1731/1730–1703<br>SEQ ID NO:13 | 546–555 | TTAGTAGGCCTGTCGAGGCTATGGGTTGACCATAACCAC |
| 2314–2310/2309–2282<br>SEQ ID NO:14 | 739–748 | TAACAAGGCCTGCCGCTTGTGCGCTTACATCACATGGCG |

TABLE II-continued

| Position (BP) | Position (AA) | Sequence |
|---|---|---|
| 2784–2780/2779–2754 SEQ ID NO:15 | 896–905 | ATCAAAGGCCTCCTCCATGTTTTCAAGTCTGGCACCC |
| 3190–3186/3185–3160 SEQ ID NO:16 | 1031–1040 | GTATAAGGCCTGCCACGGCGCCACCACCAAGTGCACC |
| 3679–3675/3674–3647 SEQ ID NO:17 | 1194–1203 | CATTAAGGCCTCCACAGAATCCGAATCTCTGAGACTGAG |
| 4433–4429/4428–4405(Stop) SEQ ID NO:18 | 1444–1452 | TAAATAGGCCTTTAGTGGACATGCACTTTTTCAATTGG * stop codon |

Example 3—Preparation of RNA and cDNA for PCR

The RNA which was used as a template for generation of the PCR amplified fragments useful in this invention was obtained from the following coronavirus strains: WT WSU 1146 and FECV (WSU 1683) from Washington State University, WT UCD-1, WT UCD-2, and WT UCD-4 from N. Pedersen at the University of California-Davis, WT TN406 from Dr. J. Black, Tennessee, and WT DF2 and TS DF2 from SmithKline Beecham Animal Health, Lincoln. WT UCD-1, WT WSU 1146, and WSU 1683 are available from the American Type Culture Collection, Rockville, Md. The other strains are available upon request from their respective suppliers.

Viruses were cultivated as follows. Roller bottles of confluent Norden Laboratories feline kidney (NLFK) cells were infected with either WT DF2, WT WSU 1146 or FECV 1683 virus using the following protocol. The WT DF-2 FIP virus was originally isolated from a cat liver explant. After several passages of tissue homogenates in specific pathogen free (SPF) cats, the virus was adapted to Norden Laboratory Feline Kidney (NKLF) cells by cocultivation with infected primary spleens.

The TS DF-2 virus mutant was derived from WT DF2 FIP virus which had been passaged 60 times on NKLF cells at 39° C. followed by 39 passages at 31° C. The virus collected at pass 99 was ultraviolet irradiated for 5 minutes and then plaque purified prior to use as described in Christianson et al, Arch. Virol., 109:185–196 (1989).

The growth medium was removed and virus (MOI=0.1) was absorbed in 50 ml of BME supplemented with 2% FBS. Only WT DF2 FIPV infections were performed in serum-free medium. The virus was absorbed for 2 hours and then 250 ml of growth medium added. The cultures were monitored for cytopathic effect (CPE) and typically harvested at 24–36 hours post-infection.

A similar protocol was followed for infections with the TS FIPV strain except all incubations were performed at 31° C.

WT TN406, WT UCD-1 and WT UCD-2 were grown in T150 flasks of *Felis catus* whole fetus (FCWF) cells. Cells were split 1:2 and inoculated with approximately 105 $TCID_{50}$ of virus in 50 ml of BME+2% FBS. The cultures were again monitored for CPE and typically harvested at 48–72 hours post-infection.

Total cytoplasmic RNA was prepared from the infected monolayers by guanidine isothiocyanate extraction according to Chirgwin, *Biochemistry,* 18:5294 (1979). Where indicated, poly A+mMNA was isolated from total RNA by absorption to and subsequent batch elution from oligo dT cellulose. The cDNA was synthesized from this total RNA by standard techniques.

Example 4: PCR Amplification

PCR amplification was performed on the cDNA of the FIPV of Example 3 under the following conditions:

In a final reaction volume of 20 μl of 1×PCR buffer (10×PCR buffer: 100 mM Tris-HCl, 500 mM KCl, 15 mM $MgCl_2$, 0.01% (w/v) gelatin) the following components were assembled in RNAse free siliconized 500 μl microcentrifuge tubes: 1.0 mM of dATP, dCTP, dGTP and dTTP (dNTPs), 20 units of RNAsin (Promega Corp), 100 picomoles of random hexamer oligonucleotides (Pharmacia, 100 picomoles/μl solution in TE buffer (10 mM Tris-HCl, 1 mM EDTA, pH 7.5)), 200 units of reverse transcriptase (Moloney MULV, Bethesda Research Labs) and 1.0 μg of respective RNA isolated as described above.

To avoid pipetting errors and contamination, all solutions were aliquoted from master mixes made with diethyl pyrocarbonate (DEPC) treated water and consisted of all of the reaction components except the RNA which was added last. The mixture was incubated in a programmable thermal cycler (Perkin-Elmer Cetus) at 21° C. for ten minutes followed by 42° C. for one hour, then 95° C. for five minutes and finally held at 4° C. until PCR amplification.

Amplification of the cDNA was performed essentially according to the method of Saiki et al, *Science,* 230:1350–1354 (1985) using the Taq polymerase. Briefly, to the 20 μL cDNA reaction mixture from above was added 8.0 μL 10×PCR buffer, 1.0 μL of each upstream and downstream primer previously diluted in water to 30 picomoles per microliter and 5.0 units of Tag polymerase (Perkin-Elmer Cetus). Final volume was made up to 100 μL using DEPC (diethyl pyrocarbonate) treated water and overlaid with 100 μL of mineral oil. As above master mixes were prepared to avoid contamination.

The reaction was performed in the Perkin-Elmer Cetus thermal cycler for one cycle by denaturing at 95° C. for 1 minute, annealing at 37° C. for 2 minutes followed by extension at 72° C. for 40 minutes. This initial cycle increased the likelihood of first strand DNA synthesis. A standard PCR profile was then performed by a 95° C.-1 minute denaturation, 37° C.-2 minute annealing, 72° C.-3 minute extension for 40 cycles. A final extension profile was done by 95° C.-1 minute denaturation, 37° C.-2 minute annealing, 72° C.-15 minute extension and held at 4° C. until analyzed.

A small aliquot (5 μl) of the completed PCR reactions were analyzed by agarose gel electrophoresis to confirm amplification of the predicted DNA fragment.

For the galK/FIPV S clone 58-3 only (SEQ ID NO: 19 and 20) [See FIG. 3], double stranded cDNA was first synthesized using 2 mg poly A+ RNA isolated from TS FIPV infected NLFK cells. Boehringer Mannheim's cDNA synthesis kit was used according to the manufacturer's specifications. The cDNAs were extracted with phenol/chloroform (1:1), ethanol precipitated and sized on 1.4% alkaline agarose gels. The yield of cDNA was determined as specified by Boehringer.

In the PCR reaction then, 100 ng of cDNA and 100 ng of each primer were added to all 4 dNTPs, $MgCl_2$ and 5 units Taq polymerase in a 100 $\mu$L standard reaction mixture at concentrations as described above [see Table II]. The mixture was overlaid with 100 $\mu$L mineral oil and incubated in a Perkin Elmer Cetus thermocycler for 30 cycles. Each complete cycle incubated the samples at 94° C. for 1 minute, followed by 37° C. for 2 minutes, and ending at 72° C. for 3 minutes.

PCR amplified products were analyzed by electrophoresing 5.0 $\mu$l of the mix on a 1.2% agarose gel run overnight. Bands were visualized by ethidium bromide staining the gel and UV fluorescence. Photography using Polaroid type 55 film provided a negative that could be digitized for sample distance migration and comparison against markers run on each gel. The actual sizes of the bands were then calculated using the Microgenie (Beckman) software running on an IBM AT. Reactions distinguishing WT WSU 1146 or WT DF2 from WT UCD-1 and FECV are described below in Table III.

TABLE III

| | S Regions (aa) Differentiated by PCR | | |
|---|---|---|---|
| Virus | 1–555 | 352–555 | 894–1452 |
| WT WSU 1146 or DF2 | + | + | + |
| WT UCD-1 | 0 | + | 0 |
| FECV | 0 | + | + |

The results presented in Table III indicate that the 5' primer starting at position 1 is not able to efficiently initiate DNA synthesis from any template except WT WSU 1146 and WT DF2. However, the 5' primer starting at position 352 works on all strain templates. The 3' primers starting at position 555 prime efficiently on all strains shown. The 5' and 3' primers at position 894 and 1452, respectively, prime DNA synthesis from WT WSU 1146, WT DF2 and FECV template, but not WT UCD-1. in this manner different strains of feline coronavirus can be distinguished.

The results of PCR amplification showed the amplification of amino acid range 737–1452 for the WT DF2, TS and FECV strains, respectively. A fragment of predicted size (2168 bp) was obtained from each virus.

Amplification of a second and smaller region (amino acid range 1029–1452) provided additional evidence of similarity among the strains. A fragment of predicted size (1290 bp) was again obtained from WT DF2, TS and FECV viral templates.

The differences among the strains can be demonstrated by amplification of sites within the amino terminus. Results showed amplification of amino acid range 1–748 for WT DF2 and TS. A fragment of predicted size (2261 bp) was obtained. Repeated attempts to amplify the same region from the FECV virus yielded no fragment. In addition, PCR of the amino acid range 1–223 demonstrated that the correct fragment was obtained (685 bp) for the WT DF2 and TS strains, but extra fragments were obtained for the FECV virus. Other S gene sequences generated by PCR for each virus strain are listed in Table IV below.

Example 5—Cloning FIPV S Regions

The *E. coli*-derived vector, pOTSKF33, was chosen for the cloning of the FIPV peplomer fragments generated by PCR. Cloning procedures were as described by T. Maniatis et al, cited above. The bacterial expression vector, pOTSKF33, shown schematically in FIG. 1, is being maintained at SmithKline Beecham Laboratories and is available to the public through the company.

This plasmid is a derivative of pBR322 [Bethesda Research Laboratories] and carries regulatory signals from bacteriophage lambda. The system provides a promoter which can be controlled ($\lambda P_L$), and an antitermination mechanism to ensure efficient transcription across any gene insert, high vector stability, antibiotic selection, and flexible sites for insertion of any gene downstream of the regulatory sequences. The pOTSKF33 vector also contains the coding sequence for 52 amino acids of the enzyme galactokinase, immediately adjacent to the $\lambda P_L$ promoter. The sequence of this enzyme has been manipulated to permit insertion of foreign genes and the construction of fusion proteins.

Linkers containing restriction sites for fusion in any of the three reading frames, stop codons for each phase and some additional cloning sites for fusion in any of the three reading frames, have been introduced after the first 52 amino acids of galactokinase.

Transcription from the $P_L$ promoter is tightly controlled by maintaining the plasmid in bacteria expressing the cI+repressor protein. Induction of foreign protein expression is obtained by removing the repressor. In the bacterial strains used in this study, the repressor protein is temperature-sensitive. At the permissive temperature, 32° C., the repressor functions normally to inhibit transcription from the $P_L$ regulatory sequences. An increase in growth temperature (to 42° C.) results in degradation of the repressor and expression of the fusion polypeptide is induced.

In some cases, fusion proteins can represent up to 20% of total bacterial protein. These fusion proteins can be detected with monoclonal antibodies to galK.

The method for cloning of an illustrative galK/FIPV S fusion protein 58-3 (SEQ ID NO: 20) is described as follows: The mineral oil overlay was removed from the PCR reaction mixture and a 100 $\mu$l DNA fraction was digested with XmaI and StuI in a 300 $\mu$l final volume for 18 hours at 37° C. The digested DNA was first extracted with phenol followed by phenol/chloroform (1:1) and then ethanol precipitated at −20° C. XmaI/StuI digested DNAs were incubated at 15° C. for 24 hours in a ligation mixture containing pOTSKF33 vector DNA which was digested with XmaI/StuI and phosphatased.

*E. coli* HB101 cells were transformed and insert-bearing clones identified by restriction digest of mini prep DNA. Mini prep DNA from confirmed clones was then used to transform the heat-inducible AR58 strain of *E. coli* [SmithKline Beecham Laboratories]. Stocks of confirmed clones in AR58 were used to prepare induced cultures for expression analysis. As known to those skilled in the art, HB101 cells are not universally lambda $cI857^+$. As a result, the $P_L$ promoter will not be correctly regulated during culture growth in this strain. Additional transformations are performed in *E. coli* strain AR120, as AR120 has been characterized as being exclusively lambda $cI^+$.

A plasmid containing a PCR-amplified fragment cloned into the XmaI-StuI sites of pOTSKF33 is illustrated in FIG. 2.

The remainder of the clones containing galK/FIPV S fusion proteins (SEQ ID NO: 20) were isolated using the following procedures. 2 μl of the designated PCR amplified reaction mix (approximately 500–1000 ng DNA) were digested with XmaI and StuI in a 30 μl volume of 50 mM Tris, pH 7.5, 10 mM $MgCl_2$, 10 mM BME, and 10 μg/ml BSA overnight at 37° C. One half of the digest reaction was loaded on 1% low-melting temperature agarose (Seakem) gels prepared and run in TBE. DNA fragments were isolated and eluted as described by T. Maniatis et al, cited above.

Briefly, DNA fragments were visualized after staining with ethidium bromide, excised from the gel with a scalpel and transferred to Eppendorf tubes. Gel slices were incubated 5 min at 65° C., vortexed, and 5 volumes of 20 mM Tris, pH 8.0, 1 mM EDTA were added. Samples were incubated an additional 2 minutes at 65° C. and were then extracted once with phenol and once with phenol:chloroform. The DNA was precipitated with 1/10 volume 3 M NaOAc and 2.5 volumes of cold 95% EtOH overnight at −20° C. Pelleted DNAs were resuspended and ligated overnight at 15° C. to pOTSKF33 plasmid DNA that was also digested with XmaI and StuI and phosphatased.

*E. coli* strain AR120 [SmithKline Beecham Laboratories] cells were transformed with ligation mixes and ampicillin-resistant transformants selected. Clones were screened for presence of insert by BamHI and PstI digestion of mini prep DNA. Mini prep DNA from insert-bearing clones was then used to transform AR58 cells. Confirmed clones in AR58 were used to prepare induced lysates for Western blot analysis.

FIG. 3 illustrates the PCR expression clone, AR58-3 (SEQ ID NO: 19 and 20, nucleotide and amino acid sequences, respectively). Sequencing was performed using a double stranded plasmid as a template. The construction consists of the following sequences: Nucleotides 1–168 originate from the pOTSKF33 at nucleotides 1880–2047, and encode 52 amino acids of galK. Nucleotides 169–181 of the AR58-3 encode an extraneous five amino acids. Nucleotides 182–573 of the clone originated from FIPV TS at nucleotides 356–734 and encode a 128 amino acid S gene region corresponding to published WSU 1146 strain amino acid #97–222. The total protein is 188 amino acids or about 22,500 kD using 120 as an average amino acid weight.

The predicted protein size agrees well with the band seen on both Coomassie gels and Western blots and contains functional XmaI and StuI sites. One additional amino acid results at the end of the FIPV protein due to the relegation of the StuI into pOTSKF33.

When compared to the WSU 1146 published strain, three base pair differences are apparent. The first difference lies at base number 312 in FIG. 3 (#480 of published sequence). WSU 1146 shows a "C", while AR58-3 shows a "T". No amino acid change results. The second difference lies at base number 349 of FIG. 3 (#517 of the published sequence). WSU 1146 shows an "A" and AR58-3 contains a "G". An amino acid change from Threonine to Alanine results. The third difference lies at base number 399 of FIG. 3 (#567 of the published sequence). The published strain shows a "T" and AR58-3 contains a "C". No amino acid change results. Additionally, a two amino acid insert (Tyr Ile) occurs in AR58-3 at amino acid numbers 84 and 85 in FIG. 3. These amino acids do not appear at a homologous position in the published WT WSU 1146 sequence.

Example 6—Western Blot of Induced Lysates

The bacterial clones containing the galK/FIPV S fusion genes are screened for expression by Western analysis.

Expression lysates of the fusion proteins in AR58 clones containing S sequences in pOTSKF33 were prepared as follows. 3 ml of LB+50 μg/ml ampicillin (amp) were inoculated with a bacterial colony using a sterile toothpick from a master plate and grown for 18 hours at 32° C. One ml of the overnight culture was then used to inoculate 50 ml of fresh LB+amp in 250 ml Erlenmeyer flasks. Cultures were grown at 32° C. in an air shaker until $A_{650}$=0.5–0.6. At this time, 1 ml $T_0$ samples were taken and cultures were induced by adding one-third volume of LB preheated to 65° C. Flasks were immediately transferred to a shaking water bath and incubated at 42° C. for 4 hours. $A_{650}$ values were again determined and 1.3 ml $T_4$ samples were taken.

Cells were pelleted and resuspended in sample buffer (0.1 M DTT, 2% SDS, 80 mM Tris, pH 6.8, 10% glycerol, 0.02% bromophenol blue) and stored at 20° C. Prior to electrophoresis, samples were denatured by boiling for 5 minutes at 100° C. Samples were vortexed and 15–20 μl loaded on 15% SDS-polyacrylamide gels as described by Laemnli, *Nature,* 227:680–685 (1970). Proteins were transferred to 0.2 um Schleicher+Schuell BAS/NC nitrocellulose for 30–45 minutes at 250 mA using a Milliblot apparatus or for 2 hours at 250 mA at 40° C. in Tris/glycine buffer using a Transblot apparatus (Bio-Rad).

Filters were blocked in 2% dry milk, 1% gelatin, TBS (20 mM Tris, pH 7.5, 500 mM NaCl) for 1 hour at room temperature, rinsed with TTBS (TBS+0.05% Tween-20) and incubated with rabbit polyclonal galK antisera, or the galK monoclonal antibody HIV env 41 AS1 [Beckman Instruments] in mouse ascites fluid, at a 1:1000 dilution in TTBS and 1% gelatin for 1 hour at room temperature. Filters were washed 3×10 min in TTBS and labelled with $I^{125}$ Protein A (1 uCi/10 ml) (Amersham) in TTBS and 1% gelatin for 1 hour at room temperature. Filters were washed as before, air-dried, and exposed to XAR film for various time periods at −700° C.

Table IV summarizes expression results of several FIPV S/pOTSKF33 AR58 clones. Bacterial lysates were prepared, run on SDS polyacrylamide gels, transferred to nitrocellulose, and analyzed by Western blot using both polyclonal and monoclonal galK antiserum as described above. The virus from which RNA was extracted for PCR amplification, the S amino acid region cloned in pOTSKF33, and the predicted size of the galK/S fusion protein are also shown.

TABLE IV

| Clone | Virus | S Region* | Fusion Protein | Expression |
|---|---|---|---|---|
| 58–53 | TS DF2 | 1–105aa | 18.84 (kd) | ++ |
| 58–43 | TS DF2 | 1–223aa | 33 | ++ |
| 58–107 | FECV | 1–223aa | | ++ |
| 58–735 | WT DF2 | 1–223aa | | ++ |
| 58–3 | TS DF2 | 94–223aa | 21.86 | +++ |
| 58–399 | FECV | 94–223aa | | +++ |
| 58–465 | WT TN406 | 94–223aa | | +++ |
| 58–558 | WT DF2 | 94–223aa | | +++ |
| 58–565 | WT WSU 1146 | 94–223aa | | +++ |
| 58–494 | WT UCD-1 | 94–223aa | | +++ |
| 58–131 | WT DF2 | 94–223aa | | +++ |
| 58–885 | WT UCD-2 | 94–223aa | | +++ |
| 58–1542 | UCD-4 | 94–223aa | | +++ |
| 58–396 | FECV | 213–362aa | 24.24 | ++ |
| 58–437 | TS DF2 | 213–362aa | | ++ |
| 120–643–6 | WT DF2 | 213–362aa | | ++ |
| 58–462 | UCD-1 | 352–555aa | 30.72 | ++ |
| 58–470 | WSU | 352–555aa | | ++ |
| 58–515 | WT DF2 | 352–555aa | | ++ |

TABLE IV-continued

| Clone | Virus | S Region* | Fusion Protein | Expression |
|---|---|---|---|---|
| 58–385 | WT DF2 | 352–748aa | 54 | ++ |
| 58–389 | TS DF2 | 352–748aa | | ++ |
| 58–391 | FECV | 352–748aa | | ++ |
| 58–438 | WT DF2 | 894–1040aa | 23.88 | ++ |
| 58–441 | TS DF2 | 894–1040aa | | ++ |
| 58–476 | FECV | 894–1040aa | | ++ |
| 58–426 | WT WSU 1146 | 894–1040aa | | ++ |
| 58–569 | WT UCD-1 | 894–1040aa | | ++ |
| 58–1133 | TS DF2 | 737–1040aa | 42.7 | +++ |
| 58–1138 | TS DF2 | 1029–1452aa | 57.1 | +++ |
| 120–896 | FECV | 94–748aa | | ++ |

*Amino acid numbers indicate sequences which correspond to published amino acid sequence of WT WSU 1146.

The results in Table IV show that the induced lysates of S/pOTSKF33 AR58 clones express fusion proteins of the predicted size as detected by polyclonal and monoclonal galK antiserum. Bands representing fusion proteins were not detected in uninduced lysates or control lysates of pOTSKF33 alone. Levels of expression are quantitated in Table IV as "+++" or "++". The symbol "+++" indicates expression comparable to the level of expression produced by clone 58-3. Fusion proteins expressed to this high level are easily visualized on Coomassie stained polyacrylamide gels and may represent 5–10% of total cell protein.

The symbol "++" designates a level of expression less than that produced by 58-3 (SEQ ID NO: 20). In general, fusion proteins from these clones are not easily visualized in lysates stained with Coomassie Blues and may represent 1–2% of total cell protein.

Example 7—Induction of Large Cultures of Bacteria Expressing GalK/FIPV S Fusion Protein Overnight stationary cultures of AR58 strain *E. coli* containing the fusion plasmid were used as inoculum for 500 mls of L Broth+100 $\mu$g/ml ampicillin. The cultures were incubated at 32° C. until $OD_{650}$ reached 0.5–0.6. One third culture volume of L Broth preheated to 65° C. was added and the cultures shifted to 42° C. for an additional 4 hours of growth. The bacteria were collected by centrifugation (3500, 10° C., 15 min) and resuspended in 100 ml $H_2O$. Lysozyme and EDTA (1% and 200 mM, respectively, 100 ml of each) were added to the cell pellet and cultures incubated on ice for 1 hour. The cultures were then sonicated in 50 ml aliquots for six minutes on ice (Branson sonifier) to completely disrupt the bacteria. Following sonication, thimerosal was added to a final concentration of 0.01–0.2% for 4–18 hours at 4° C. to inactivate the lysate. Aliquots of the inactivated material were used to inoculate LB plates with and without ampicillin. None of the cultures showed visible growth after 24 hours incubation.

Example 8—Solubilization of GalK/FIPV S Fusion Protein from Bacteria

Following induction of expression, the following purification protocol for isolation of pure galK/FIPV S fusion protein from bacterial lysates was performed.

Ten mls of the inactivated extract was centrifuged at 27,000×g for 30 min (JA20). The supernatant was discarded and the pellet resuspended by vortexing for 10 minutes in 10 mls of Buffer A plus 0.2% sodium deoxycholic acid and 1% Triton X-100. Buffer A contains 50 mM Tris-HCl, pH 8.5, 5 mM EDTA, 1 mM DTT, and 5% glycerol. The extract was centrifuged at 27,000×g for 30 minutes and again the resulting supernatant was discarded. The pellet was resuspended by vortexing 10 minutes in 10 mls of Buffer A containing Triton X-100 (1%) and 0.5 M KCl.

Following centrifugation (27,000×g, 30 minutes), the pellet was resuspended by vortexing 10 minutes in 2 mls of Buffer A containing 8 M urea. The solution was again centrifuged at 27,000×g for 30 minutes and the pellet discarded. The pH of the supernatant was adjusted by stepwise addition of 10 mM Na phosphate buffer, pH 7.4, until the solution reached a volume of 20 mls (final urea concentration, 0.8M).

Example 9—Purification of Anti-Galactokinase Monoclonal Antibodies

Ascites fluid containing anti-galactokinase mAbs was produced in mice against the first 52 amino acids of galK, e.g., HIV env 41 AS1 [Beckman Instruments].

The BCA Protein Assay Kit [Pierce Chemical Co.] which consists of a bicinchoninic acid solution and a copper sulfate solution, was used according to manufacturer's instructions to determine the concentration of protein in the fluid. Copper 2+ ions in the assay are converted to copper 1+ in the presence of protein. Copper 1+ ions are then chelated to BCA molecules, resulting in a calorimetric change. The higher the protein concentration, the deeper the color. Protein concentrations are determined from absorbance measurements at 562 nm.

90 mg of total protein was added to sterile phosphate buffered saline (PBS), pH 7.4. The material was stirred on ice while ammonium sulfate was added to a final concentration of 45%. After 2 hours on ice, the precipitate was collected by centrifugation at 3000×g for 30 minutes at 40° C. The supernatant was discarded and the pellet resuspended in PBS with gentle vortexing. Again while slowly stirring on ice, saturated ammonium sulfate was added to 40%. After 1 hour, the precipitate was collected by centrifugation as previously described.

The supernatant was discarded and the pellet resuspended in PBS by vortexing. The mAb mixture was added to Spectrapor membrane tubing (M.W. cutoff 12–14000) [Fisher Scientific] and dialyzed against 4 changes of 4 liters of PBS, pH 7.4. The post-dialysate contained 19.5 mg of total protein.

Example 10—Affinity Purification of GalK/FIPV S Fusion Proteins

The anti-galactokinase mAbs were coupled to column matrix using the Immunopure™ Ag/Ab Immobilization Kit [Pierce Chemical Co]. Ten mg of anti-galactokinase Abs were immobilized on Aminolink™ (agarose) as described by the manufacturer. Columns were stored at 4° C.

Both the column and the pre-column solution containing fusion protein were brought to room temperature. The column was equilibrated with 16 mls of 10 mM Na phosphate buffer, pH 7.4. The pre-column solution was applied to the column in 4 aliquots of 5 ml each. The total pre-column eluate was re-added to column three times.

The column was then washed with 6 mls of 0.8 M urea followed by washing with 10 mM phosphate buffer, pH 7.4 (16 mls). The bound fusion protein was eluted by the addition of 5 mls of 0.1 M glycine, pH 2.8. Five 1 ml fractions were collected and neutralized with 50 $\mu$l of 1 M Tris-HCl, pH 9.5. The fractions were stored at 4° C. until needed. The column was re-equilibrated with 10 mM Na phosphate buffer, pH 7.4.

Galactokinase ELISA affinity column eluted fractions were diluted 1:100 in 10 mM borate buffer, pH 9.6, and 100 μl aliquots added to each well of 96 well plates (Nunc Immuno plates). The plates were incubated overnight at 4° C., then brought to room temperature and washed once with PBS (pH 7.4) containing 0.05% Tween-20 (PBS-Tween). Blocking agent (PBS+1% polyvinyl alcohol, PVA) was added in 200 μl aliquots to each well for 30 min at 37° C. The plate was washed once with PBS-Tween and then 100 μl of the mouse anti-galactokinase mAb (1:1000) in PBS+ 1% PVA added to each well.

After 1 hour at 37° C., the plates were washed once with PBS-Tween. Goat anti-mouse IgG peroxidase labelled conjugate (Kirkegaard and Perry) was diluted 1:1000 in PBS+ 1% PVA and aliquots of 100 μl added to each well. The plates were incubated for 1 hour at 37° C. and then washed one time with PBS-Tween. Aliquots of 100 μl of the ABTS peroxidase substrate system (Kirkegaard and Perry) were added to each well and after 10 minutes of incubation at room temperature, the intensity of chromogenic reaction was measured at 405 nm on a Molecular Devices Vmax plate reader.

Example 11—Western Analysis Using Cat Sera

Affinity column eluted fractions of fusion proteins were denatured with Laemmli sample buffer and electrophoresed on preparative 10% SDS-polyacrylamide gels. Following electrophoresis, the proteins were transferred to nitrocellulose according to the procedure of Towbin et al, *Proc. Natl. Acad. Sci. USA,* 76:4350–4354. The nitrocellulose was incubated overnight at room temperature in blocking solution containing 50 mM Tris, pH 7.4, 150 mM NaCl and 5% non-fat dried milk (Buffer A). Following blocking, the nitrocellulose was sliced into 5 mm strips and placed into individual incubation chambers.

Each strip was incubated for 1 hour at room temperature with unique cat sera diluted 1:30 in 3 ml of 50 mM Tris, pH 7.4, 150 mM NaCl, 0.2% Triton X-100 and 5% non-fat dried milk (Buffer B). The strips were then washed for 15 minutes with Buffer A followed by one Buffer B wash. Goat anti-cat IgG phosphatase labelled conjugate (Kirkegaard and Perry), diluted 1:1000 in Buffer A, was added to each chamber for 1 hour at room temperature. The nitrocellulose strips were then washed successively with Buffer B, Buffer A and then twice with Buffer C (20 mM Tris, pH 7.4, 500 mM NaCl, 5% non-fat dried milk). BCIP/NBT phosphatase substrate system [Kirkegaard and Perry] was added to each strip; the reaction was stopped by decanting the substrate and washing with $H_2O$ after 30 minutes at room temperature.

Western blots were performed to determine the binding affinity of purified fusion proteins to sera from cats challenged either with WT DF2 FIPV or WT WSU 1146. For cats challenged with WT DF2 FIPV, the following was performed: three weeks post second TS-FIPV vaccinated serum and four weeks post WT DF2 FIPV challenged serum, both from non-symptomatic cat #IR03; three weeks post second TS-FIPV vaccinated serum and four weeks post WT DF2 FIPV challenged serum, both from symptomatic cat #JI1; non-vaccinated pre-challenge serum and four weeks post WT DF2 FIPV challenged serum, both from non-symptomatic cat #G26; non-vaccinated pre-challenge serum and four weeks post WT DF2 FIPV challenged serum, both from symptomatic cat #IRV5; (mAb) anti-galactokinase monoclonal antibody; (J736) serum from rabbit which was immunized with S peptide conjugate ovalbumin-glutaraldehyde-137–151 amino acid fragment; and (J739) serum from rabbit which was immunized with S peptide conjugate ovalbumin-glutaraldehyde-150–180 amino acid fragment.

Only post FIPV challenged sera from symptomatic cats recognized the 22 kD FIPV galK/S fusion protein expressed by recombinant 58-3 (SEQ ID NOS: 19 and 20). The anti-galactokinase mAb and rabbit sera served as positive controls.

For cats challenged with WT WSU 1146, the following was performed: three weeks post second TS-FIPV vaccinated serum, and four weeks post WT WSU 1146 FIPV challenged serum, both from non-symptomatic cat #EU6; three weeks post second TS-FIPV vaccinated serum and four weeks post WT WSU 1146 FIPV challenged serum, both from symptomatic cat #FW3; non-vaccinated pre-challenge serum,and four weeks post WT WSU 1146 FIPV challenged serum, both from non-symptomatic cat #FV2; non-vaccinated pre-challenge serum and four weeks post WT WSU 1146 FIPV challenged serum, both from symptomatic cat #PB2; (mAb) anti-galactokinase monoclonal antibody; (J736) serum from rabbit which was immunized with S peptide conjugate ovalbumin-glutaraldehyde-137aa-151aa; (J739) serum from rabbit which was immunized with S peptide conjugate ovalbumin-glutaraldehyde-150aa-180aa; and a Control which received only second conjugated goat-anti-cat IgG-Phosphatase antibody. Only post FIPV challenged sera from symptomatic cats recognized the 22kd FIPV galK/S fusion protein expressed by recombinant 58-3 (SEQ ID NOS: 19 and 20). The anti-galactokinase mAb and rabbit sera served as positive controls.

Example 12—Partial Sequences of Other Strains

In the course of the present invention, the following DNA and amino acid sequences of the complete S gene WT DF2 FIPV (SEQ ID NOS: 21 and 22, respectively), a fragment of the S gene of DF2-HP (SEQ ID NOS: 23 and 24, respectively), the complete S gene TS (SEQ ID NOS: 25 and 26, respectively), a fragment of the S gene of TS-BP (SEQ ID NOS: 27 and 28, respectively), a fragment of the S gene of the WT TN406 (SEQ ID NOS: 29 and 30, respectively), a fragment of the S gene of UCD-2 (SEQ ID NOS: 53 and 54, respectively) and the complete S gene of the FECV (SEQ ID NOS: 31 and 32, respectively) have been obtained by procedures substantially similar to those described in Example 1 for WT WSU 1146.

FIG. 4 provides the sequences of the complete S gene of the WT FIPV DF2 virus (SEQ ID NOS: 21 and 22) and a fragment of the S gene of the FIPV DF2-HP virus (SEQ ID NOS: 23 and 24). The bold print indicates the places where the sequence of DF2-HP differs from WT DF2. Nucleotide changes in DF2-HP from WT DF2 are indicated above the WT DF2 sequence with an asterisk and amino acid differences are indicated below the WT DF2 sequence with an asterisk.

FIG. 5 provides the sequences of the complete S gene of the TS FIPV (SEQ ID NOS: 25 and 26) and a fragment of the S gene of the TS-BP (SEQ ID NOS: 27 and 28) from amino acids 1–748, which each include a sequence homologous to the AR58-3 S-derived peptide (SEQ ID NO: 20). Nucleotide differences in the TS-BP sequence from TS are indicated in bold type above the TS sequence with an asterisk and amino acid differences are similarly indicated below the TS sequence.

Certain areas of homology between AR58-3, as illustrated in FIG. 3 (SEQ ID NO: 20), and the sequences of TS FIPV (SEQ ID NOS: 25 and 26), WT DF2 FIPV (SEQ ID NOS: 21 and 22) are indicated by underlining in FIGS. 4 and 5 below.

FIG. 6 provides the sequences of the WT TN406 FIPV from amino acid 102–223 (SEQ ID NO: 29 and 30).

FIG. 7 provides the sequences of the S gene of the FECV virus from amino acid 1–1452 (SEQ ID NOS: 31 and 32).

FIG. 8 provides the sequences of the S gene of the UCD-2 virus from amino acid 1–125 (SEQ ID NO: 53 and 54).

Differences between the nucleotide and amino acid sequences of FIPV, strains WT WSU 1146, WT DF2, DF2-HP, TS, TS-BP, WT TN406, FECV, UCD-2 and the Consensus Sequence, which extends from nucleotides 1–2246 (encoding amino acid 1–748) of the S gene are as follows, with the Consensus Sequence illustrated in FIG. 9 (SEQ ID NOS: 33 and 34) serving as the reference. No consensus sequence has been obtained for that portion of the gene beyond amino acid 748 (base pair 2246). Therefore, for the strains for which the genes have been sequenced beyond this point, reference is made to the published WT WSU 1146 sequence.

WT WSU 1146 differs from the Consensus Sequence (SEQ ID NO:33) by the following nucleotide changes: C at 849; A at 2029; G at 1346 and deletions: 351–356. WT WSU 1146 contains the following amino acid changes: Gly at 449 and Asn at 677 and deletions: 119 and 120.

WT DF2 (SEQ ID NO:21) differs from the Consensus Sequence (SEQ ID NO:33) by the following nucleotide changes: A at 216; A at 218, C at 849, G at 1346, C at 1370, C at 1597, C at 1751, A at 2029. WT DF2 (SEQ ID NO:22) contains the following amino acid changes: Gin at 73; Gly at 449, μla at 459; His at 533; Pro at 584, and Asn at 677.

In addition, WT DF2 (SEQ ID NO:21) differs from the published WT WSU 1146 sequence by the following nucleotide changes (the corresponding WT WSU 1146 numbers follow in parentheses): C at 2541 (T at 2601); C at 4121 (A at 4185); C at 4210 (T at 4273); T at 4330 (A at 4394). WT DF2 (SEQ ID NO:22) differs from the published WT WSU 1146 sequence by the following amino acid differences: Thr at 1374 (Asn at 1372) and Tyr at 1444 (Asn at 1442).

DF2-HP (SEQ ID NO:23) differs from the Consensus Sequence (SEQ ID NO:33) by the following nucleotide changes: G at 400; C at 1083; T at 849; G at 1346; C at 1791 and G at 2029. DF2-HP (SEQ ID NO:24) contains the following amino acid changes: Glu at 134; Gly at 449 and Asp at 677.

TS (SEQ ID NO:25) differs from the Consensus Sequence (SEQ ID NO:33) by the following nucleotide changes: T at 90; .T at 849; T at 956; A at 1346; C at 1889; A at 1984; and G at 2029. TS (SEQ ID NO:26) contains the following amino acid changes: Val at 319; Thr at 630; Ile at 662; Asp at 449; and Asp at 677.

In addition, TS [SEQ ID NO:25) differs from the published WT WSU 1146 sequence by the following nucleotide changes: T at 2309 (C at 2372); C at 2541 (T at 2604); A at 4024 (G at 4087) and G at 4074 (A at 4137). TS (SEQ ID NO:26] differs from the amino acid sequence of WT WSU 1146 by the following amino acid changes: Ile at 770 (Thr at 768) and Thr at 1342 (Ala at 1340).

TS-BP (SEQ ID NO:27) differs from the Consensus Sequence (SEQ ID NO:33) by the following nucleotide changes: T at 849; A at 1346; G at 2029. TS-BP (SEQ ID NO:28) contains the following amino acid inserts: Asp at 449 and Asp at 677.

WT TN406 (SEQ ID NO:29) differs from the Consensus Sequence (SEQ ID NO:33) by the following nucleotide changes: T at 659. WT TN406 (SEQ ID NO:30) contains an amino acid change to Ile at position 220.

FECV (SEQ ID NO:31) differs from the Consensus Sequence (SEQ ID NO:33) by the following nucleotide changes: C at 36, T at 48, C at 53, G at 60, T at 61, C at 66, T at 72, T at 75, G at 77, A at 99, T at 120, C at 126, T at 130, T at 141, T at 158, A at 230, G at 232, A at 266, T at 276, T at 312, C at 313, T at 327, A at 336, A at 346, C at 348, C at 351, A at 360, G at 370, A at 393, G at 400, T at 412, T at 420, A at 433, G at 439, A at 445, C at 447, A at 448, C at 449, C at 450, A at 457, G at 458, G at 469, T at 476, A at 487, A at 488, G at 521, T at 525, G at 546, A at 564, G at 576, A at 598, T at 600, G at 602, A at 614, C at 618, T at 689, T at 742, T at 759, G at 765, T at 775, C at 789, C at 792, T at 795, C at 801, A at 810, T at 813, G at 814, T at 815, G at 816, A at 819, C at 849, T at 858, C at 873, A at 894, C at 906, C at 913, A at 918, G at 919, C at 924, A at 930, G at 984, T at 993, G at 996, G at 1001, A at 1008, A at 1026, T at 1046, C at 1056, G at 1089, G at 1095, T at 1096, G at 1107, G at 1126, A at 1139, T at 1160, T at 1182, T at 1200, G at 1209, G at 1245, T at 1266, A at 1346, C at 1360, A at 1376, C at 1413, G at 1419, G at 1455, G at 1491, G at 1548, T at 1551, C at 1555, T at 1557, G at 1560, T at 1586, G at 1594, C at 1597, T at 1599, A at 1606, G at 1637, C at 1641, A at 1662, A at 1665, T at 1669, T at 1680, T at 1701, C at 1704, A at 1707, G at 1734, T at 1737, T at 1755, T at 1757, T at 1761, G at 1764, A at 1797, T at 1815, C at 1818, G at 1833, A at 1878, C at 1917, C at 1923, C at 1941, A at 1965, T at 2013, G at 2085, A at 2029, G at 2079, T at 2082, A at 2120, C at 2042, C at 2207, inserts: CAA between nucleotides 135 and 136 of the consensus sequence; CCA between nucleotides 223 and 224 of the consensus sequence; and deletions at positions: 138–140; 216–218.

FECV (SEQ ID NO:32) differs from the Consensus Sequence (SEQ ID NO:33) by the following amino acid changes: Ser at 18, Ser at 21, Asn at 24, Arg at 26, Gln at 46, Ser at 47, Ile at 53, Thr at 73, Tyr at 77, Glu at 78, Asp at 89, Ile at 116, Gly at 124, Glu at 134, Leu at 138, Asn at 145, Asp at 147, Asn at 149, Thr at 150, Asp at 157, Ile at 159, Asn at 163, Arg at 174, Glu at 188, Asn at 200, Trp at 201, Asn at 205, Val at 230, Phe at 253, Tyr at 259, Val at 272, Val at 307, Ser at 334, Val at 376, Asn at 380, Phe at 388, Asp at 449, Asp at 459, Lys at 485, Leu at 519, Ile at 529, Ala at 532, His at 533, Ile at 536, Arg at 546, Ile at 586, Glu at 598, Asp at 605, Asn at 677, Glu at 693, and Gln at 707.

In addition, WT WSU 1146 differs from the nucleotide sequence of FECV by the following changes (the WT WSU 1146 nucleotide and nucleotide numbers appear before the FECV nucleotides and nucleotide numbers which are in parentheses): T at 2271 (C at 2208); C at 2372 (A at 2309); T at 2376 (C at 2313); G at 2385 (A at 2322); C at 2421 (T at 2358); G at 2426 (A at 2363); G at 2479 (A at 2416); T at 2496 (C at 2433); C at 2550 (T at 2487); A at 2579 (C at 2516); T at 2598 (C at 2535); T at 2604 (C at 2541); T at 2619 (C at 2556); G at 2628 (T at 2565); T at 2640 (C at 2577); T at 2676 (C at 2613); G at 2718 (T at 2655); A at 2739 (G at 2676); T at 2796 (C at 2733); C at 2799 (T at 2736); G at 2802 (T at 2739); T at 2859 (C at 2796); G at 2882 (A at 2819); C at 2899 (T at 2836); C at 2908 (T at 2845); T at 2916 (C at 2853); A at 2922 (G at 2859); G at 2950 (C at 2887); T at 2967 (C at 2904); A at 2982 (G at 2919); A at 2991 (T at 2928); T at 3033 (A at 2970); C at 3042 (T at 2979); A at 3051 (C at 2988); G at 3057 (A at 2994); T at 3090 (G at 3027); C at 3091 (T at 3028); A at 3096 (T at 3033); C at 3110 (A at 3047); A at 3138 (T at 3075); T at 3157 (C at 3094); G at 3183 (T at 3120); A at 3207 (T at 3144); G at 3210 (A at 3147); A at 3261 (G at 3198); T at 3312 (A at 3249); T at 3318 (C at 3255); C at 3349 (A at 3286); C at 3360 (A at 3297); G at 3375 (A at 3312); T at 3423 (C at 3360); T at 3429 (A at 3366); T at 3468 (C at 3405); T at 3540 (A at 3477); A at 3591 (G at 3528); A at 3621 (G at 3558); G at 3645 (A at 3582); T at 3648 (C at 3585); G at 3651 (A at 3588); C at 3663 (T at 3600); T at 3687 (C at 3624); A at 3699 (T at 3636); A at 3741 (G at 3678); A at 3753 (G at 3690); T at 3778 (C at 3715); C at 3813 (T at 3750); G at 3834 (A at 3771); T at 3855 (C at 3792); C at 3879 (T at 3816); T at 3905 (C at 3842); A at 3936 (G at 3873); T at 3942 (C at 3879); C at 3960 (T at 3897); G at 3963 (A at 3900); T at 3975 (C at 3912); T at 4008 (C at 3945); A at 4014 (G at 3951); C at 4026 (T at 3963); T at 4068 (G at 4005); C at 4083 (T at 4020); G at 4128 (A at 4065); T at 4149 (C at 4086); C at 4152 (T at 4089); T at 4155 (C at 4092); A at 4158 (T at 4095); T at 4182 (C at 4119); T at 4191 (C at 4128); T at 4194 (C at 4131); G at 4266 (A at 4203); T at 4272 (C at 4209); G at 4282 (A at 4219); C at 4300 (T at 4237); T at 4316 (G at 4253); C at 4320 (T at 4257); T at 4347 (C at 4284); and A at 4371 (G at 4308). FECV differs from the amino acid sequence of WT WSU 1146 by the following changes (WSU 1146 amino acids appear in parentheses): Lys at 770 (Thr at 768); Asn at 788 (Ser at 786); Ile at 806 (Val at 804); Thr at 839 (Asn at 837); Ile at 855 (Met at 853); Asn at 940 (Ser at 938); Arg at 963 (Gly at 961); Asp at 1016 (Ala at 1014); Lys at 1096 (Gln at 1094); Pro at 1239 (Ser at 1237); Ala at 1281 (Val at 1279); Leu at 1335 (Phe at 1333); Ile at 1407 (Val at 1405); Cys at 1418 (Phe at 1416); and Met at 1436 (Ile at 1434).

UCD-2 (SEQ ID NO:54) differs from the amino acid sequence of the Consensus Sequence by the following amino acid change: Tyr at #21, Ile at #22. The are no nucleotide differences between the UCD-2 nucleic acid sequence and the Consensus Sequence.

The following general conclusions can be drawn from this information. FECV and all of the viruses derived from WT DF2 contain a 2 amino acid insert (Tyr Ile) at positions #119 and 120 which is absent in the WT WSU 1146 S gene. In general, however, the homology between WT WSU 1146 and WT DF2 derived strains is quite high (>99.0%). Six changes exist in the first 748 amino acids of the DF2-HP S gene as compared to the WT DF2 sequence. The majority of the changes are conservative but several (#459, #533) may perturb protein conformation. The overall amino acid homology between DF2 HP and DF2 remains >99.0%.

In the first half of the S gene, mutagenesis of the DF2 HP could have caused the five amino acid changes observed in TS FIPV. Again, the majority of the changes are conservative in nature. However, the amino acid substitutions at position #553 and #630 may cause changes in the protein plot structure. Overall, the similarity of the two viruses is greater than 99.0%.

The 1–748 amino acid sequences of TS FIPV (SEQ ID NO:26) and TS-BP (SEQ ID NO:28) are highly homologous (>99.0%). However, comparison of TS FIPV (SEQ ID NO:26) with TS BP (SEQ ID NO:28) did show three amino acid changes. Two of these represented conservative changes, from valine to alanine at #319 and from isoleucine to valine at #662. Examination of the plot structures at these two amino acid positions predicts that these two changes will have minimal effect of the protein conformation. The third change at #630 is significant: from a tyrosine in TS FIPV to a lysine residue in the TS BP. While this amino acid change may perturb protein folding, the consensus amino acid at this portion in WT DF2 (SEQ ID NO:22), DF2 HP (SEQ ID NO:24) and FECV (SEQ ID NO:32) is a lysine. This result suggests that the change back to a lysine in TS BP is not associated with a return to virulence.

Only one amino acid change (#220, tryptophan to isoleucine) was observed in the sequence of the WT TN406 94-223 amino acid region with respect to the other FIPV strains, which are all Type II. WT TN406 is a Type I virus and typically requires greater than one exposure to 15 cause disease in cats. The illustrated TN406 sequence consists of nucleotides 302–671 [SEQ ID NO: 29] and amino acid numbers 102–223 [SEQ ID NO: 30].

Example 13—Challenge Studies

To further identify FIPV and FECV strains that contained S gene sequences sufficiently non-homologous to be capable of selectively distinguishing various FIPV strains from FECV, sera was screened from either rabbits immunized with synthetic peptides representing amino acids 137–151 or 150–180 or cats challenged with specific feline coronaviruses. The results are as follows. Sera from cats immunized with FIPV strains WT WSU 1146 or WT DF2 did not recognize a fusion protein representing amino acids 94–223 of FECV when probed on a Western blot. In contrast, a fusion protein representing amino acids 94–223 of TS FIPV was no recognized by sera from cats infected with FECV but was detected on a Western blot probes with sera from WT WSU 1146-infected or WT DF2-infected cat sera. Sera from rabbits immunized with a synthetic peptide made to the WT WSU 1146 amino acid sequence a t positions 137–151 recognized only the TS FIPV but not the FECV 94–223 fusion protein. These results suggest that specific sequences, such as 137–151 amino acids, within the 94–223 fusion protein, may be useful in differentiating FIPV from FECV. As illustrated in the following Table V, both the TS FIPV and FECV 94–223 amino acid fusion proteins were recognized by galK monoclonal antibody HIV env 41 ASI [Beckman Instruments].

TABLE V

| Challenge Virus Type | Serum Type | TS FIPV AR 58–3 94–223 aa | FECV AR 58–399 94–223 aa |
|---|---|---|---|
| WSU 1146 | post-Chall* | + | – |
| WT DF2 | Post-Chall | + | – |
| FECV | Post-Vac-3 | – | + |
| Rabbit | WT FIPV aa 137–151 | ++ | – |
| | WT FIPV aa 150–180 | ++ | NT |
| Mouse | Anti-GalK Mab | ++ | ++ |

+/– denotes reactivity on Western blot with cat sera
*symptomatic cats which died from FIPV after challenge
NT not tested

Example 14—Antibody Recognition of Non-homologous Sequences

Synthetic peptides made from the WT DF2/WT WSU 1146 sequence at amino acid positions #137–151 and #950–990 (a control) were used to immunize rabbits. As illustrated in the following Table VI, the antibody directed against the 137–151 synthetic peptide recognized fusion proteins representing WT DF2 and TS FIPV 94–223 amino acids, but not the analogous fusion protein made from FECV. As predicted, the control antibody did not recognize any 94–223 a.a. fusion protein tested. The monoclonal gal-K antibody recognized the galactokinase portion of all fusion proteins. On the following illustration of the Western Blot results, a “0” indicates no reaction and a “4” indicates a strong reaction.

TABLE VI

| Sera | TS FIPV 94–223 | TN406 94–223 | FECV 94–223 |
|---|---|---|---|
| Rabbit α 137–151 aa | 2 | 2 | 0 |
| Rabbit α 950–990 aa | 0 | 0 | 0 |
| Mouse anti-galK | 4 | 2 | 4 |

Numerous modifications and variations of the present invention are included in the above-identified specification and are expected to be obvious to one skilled in the art. Such modification and alterations are believed to be encompassed in the scope of the claims appended hereto.

What is claimed is:

1. A DNA molecule consisting of a nucleotide sequence selected from the group consisting of:

(a) SEQ ID NO: 19;

(b) SEQ ID NO: 23;

(c) SEQ ID NO: 27;

(d) SEQ ID NO: 29;

(e) SEQ ID NO: 31; and (f) SEQ ID NO: 53;

wherein said nucleotide sequence selected from (b), (c), (d), (e) and (f) is optionally fused in frame to a nucleotide sequence that encodes a fusion partner.

2. The DNA molecule of claim 1, wherein the fusion partner is selected from the group consisting of galactokinase, beta-galactosidase, ubiquitin, α mating factor, and influenza NS-1, or a portion thereof.

3. The DNA molecule of claim 2, wherein the fusion partner comprises the N-terminal 52 amino acid residues of galactokinase.

4. A DNA molecule consisting of a nucleotide sequence which encodes a peptide selected from the group consisting of FIPV or FECV S protein amino acid residue numbers 1 to about 748, 1 to 360, about 94 to about 223, 97 to 222, and about 121 to about 180.

5. A DNA molecule consisting of a nucleotide sequence selected from the group consisting of:

| | |
|---|---|
| [(l)] (a) | SEQ ID NO: 35; |
| [(m)] (b) | SEQ ID NO: 37; |
| [(n)] (c) | SEQ ID NO: 39; |
| [(o)] (d) | SEQ ID NO: 41; |
| [(p)] (e) | SEQ ID NO: 43; |
| [(q)] (f) | SEQ ID NO: 45; |
| [(r)] (g) | SEQ ID NO: 47; |
| [(s)] (h) | SEQ ID NO: 49; |
| [(t)] (i) | SEQ ID NO: 51; and |
| [(u)] (j) | a nucleotide sequence from an FIPV S gene which sequence corresponds in size and position to any of sequences [(l)–(t)] (a)–(i) |

6. An isolated DNA molecule comprising the nucleotide sequence of SEQ ID NO:31, wherein said nucleotide sequence is optionally fused in frame to a nucleotide sequence that encodes a fusion partner.

7. A recombinant expression vector, comprising the DNA molecule of any of claims 4, 2, 3, 5, 1 or 6 in operative association with a regulatory nucleotide sequence capable of directing the expression of the DNA molecule in a host cell.

8. A method for producing a peptide or protein useful in the diagnosis of a disease caused by a feline coronavirus, comprising transforming a host cell with the recombinant expression vector of claim 6, culturing the transformed host cell under conditions conducive to the expression of the peptide or protein encoded by the DNA molecule, and harvesting the expressed peptide or protein.

9. A polynucleotide molecule consisting of a nucleotide sequence selected from the group consisting of SEQ ID NOS:1–18.

* * * * *

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
(A) LENGTH: 39 base pairs
(B) TYPE: nucleic acid
(C) STRANDEDNESS: double
(D) TOPOLOGY: unknown (ii) MOLECULE TYPE: DNA (genomic)

(xi) SEQUENCE DESCRIPTION: SEQ ID NO:1:

GTGCCCCCGG GTATGATTGT GCTCGTAACT TGCCTCTTG 39

(2) INFORMATION FOR SEQ ID NO:2:

(i) SEQUENCE CHARACTERISTICS:
(A) LENGTH: 35 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:2:

AAATACCCGG GCACTGGTAA TGCACGTGGT AAACC 35

(2) INFORMATION FOR SEQ ID NO:3:

(i) SEQUENCE CHARACTERISTICS:
(A) LENGTH: 35 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:3:

GTATTCCCGG GCACGCTCAA GCACTGCTAC CTGGG 35

(2) INFORMATION FOR SEQ ID NO:4:

(i) SEQUENCE CHARACTERISTICS:
(A) LENGTH: 36 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:4:

CAGATCCCGG GGTACAATCT GGTATGGGTG CTACAG 36

(2) INFORMATION FOR SEQ ID NO:5:

(i) SEQUENCE CHARACTERISTICS:
(A) LENGTH: 39 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:5:

-continued

GCTTACCCGG GGTGGTTATG GTCAACCCAT AGCCTCGAC 39

(2) INFORMATION FOR SEQ ID NO:6:

(i) SEQUENCE CHARACTERISTICS:
(A) LENGTH: 39 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:6:

TGTGACCCGG GCGCCATGTG ATGTAAGCGC ACAAGCGGC 39

(2) INFORMATION FOR SEQ ID NO:7:

(i) SEQUENCE CHARACTERISTICS:
(A) LENGTH: 37 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:7:

GCAATCCCGG GGGGTGCCAG ACTTGAAAAC ATGGAGG 37

(2) INFORMATION FOR SEQ ID NO:8:

(i) SEQUENCE CHARACTERISTICS:
(A) LENGTH: 37 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:8:

CATTACCCGG GGGTGCACTT GGTGGTGGCG CCGTGGC 37

(2) INFORMATION FOR SEQ ID NO:9:

(i) SEQUENCE CHARACTERISTICS:
(A) LENGTH: 39 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:9:

TAGGTCCCGG GCTCAGTCTC AGAGATTCGG ATTCTGTGG 39

(2) INFORMATION FOR SEQ ID NO:10:

(i) SEQUENCE CHARACTERISTICS:
(A) LENGTH: 36 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:10:

ATAATAGGCC TGGTTTACCA CGTGCATTAC CAGTGC 36

-continued (2) INFORMATION FOR SEQ ID NO:11:

(i) SEQUENCE CHARACTERISTICS:
(A) LENGTH: 35 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:11:

GTATTAGGCC TCCCAGGTAG CAGTGCTTGA GCGTG 35

(2) INFORMATION FOR SEQ ID NO:12:

(i) SEQUENCE CHARACTERISTICS:
(A) LENGTH: 36 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:12:

AAATAAGGCC TCTGTAGCAC CCATACCAGA TTGTAC 36

(2) INFORMATION FOR SEQ ID NO:13:

(i) SEQUENCE CHARACTERISTICS:
(A) LENGTH: 39 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:13:

TTAGTAGGCC TGTCGAGGCT ATGGGTTGAC CATAACCAC 39

(2) INFORMATION FOR SEQ ID NO:14:

(i) SEQUENCE CHARACTERISTICS:
(A) LENGTH: 39 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:14:

TAACAAGGCC TGCCGCTTGT GCGCTTACAT CACATGGCG 39

(2) INFORMATION FOR SEQ ID NO:15:

(i) SEQUENCE CHARACTERISTICS:
(A) LENGTH: 37 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:15:

ATCAAAGGCC TCCTCCATGT TTTCAAGTCT GGCACCC 37

(2) INFORMATION FOR SEQ ID NO:16:

(i) SEQUENCE CHARACTERISTICS:
(A) LENGTH: 37 base pairs

-continued (B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:16:

GTATAAGGCC TGCCACGGCG CCACCACCAA GTGCACC 37

(2) INFORMATION FOR SEQ ID NO:17:

(i) SEQUENCE CHARACTERISTICS:
(A) LENGTH: 39 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:17:

CATTAAGGCC TCCACAGAAT CCGAATCTCT GAGACTGAG 39

(2) INFORMATION FOR SEQ ID NO:18:

(i) SEQUENCE CHARACTERISTICS:
(A) LENGTH: 38 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:18:

TAAATAGGCC TTTAGTGGAC ATGCACTTTT TCAATTGG 38

(2) INFORMATION FOR SEQ ID NO:19:

(i) SEQUENCE CHARACTERISTICS:
(A) LENGTH: 573 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..570

(xi) SEQUENCE DESCRIPTION: SEQ ID NO:19:

```
ATG GAT CCC GAA TTC CAA GAA AAA ACA CAA TCT CTG TTT GCC AAC GCA       48
Met Asp Pro Glu Phe Gln Glu Lys Thr Gln Ser Leu Phe Ala Asn Ala
  1               5                  10                  15

TTT GGC TAC CCT GCC ACT CAC ACC ATT CAG GGC CCT GGC CGC GTG AAT       96
Phe Gly Tyr Pro Ala Thr His Thr Ile Gln Gly Pro Gly Arg Val Asn
             20                  25                  30

TTG ATT GGT GAA CAC ACC GAC TAC AAC GAC GGT TTC GTT CTG CCC TGC      144
Leu Ile Gly Glu His Thr Asp Tyr Asn Asp Gly Phe Val Leu Pro Cys
         35                  40                  45

GCG ATT GAT TAT CAA ACC GTG ATC CCT AAT ACC CGG GGC ACT GGT AAT      192
Ala Ile Asp Tyr Gln Thr Val Ile Pro Asn Thr Arg Gly Thr Gly Asn
     50                  55                  60

GCA CGT GGT AAA CCA TTA TTA TTT CAT GTG CAT GGT GAG CCT GTT AGT      240
Ala Arg Gly Lys Pro Leu Leu Phe His Val His Gly Glu Pro Val Ser
 65                  70                  75                  80

GTT ATT ATA TAT ATA TCG GCT TAT AGG GAT GAT GTG CAA CAA AGG CCC      288
Val Ile Ile Tyr Ile Ser Ala Tyr Arg Asp Asp Val Gln Gln Arg Pro
```

-continued

```
                 85                  90                  95

CTT TTA AAA CAT GGG TTA GTG TGT ATA ACT AAA AAT CGC CAT ATT AAC      336
Leu Leu Lys His Gly Leu Val Cys Ile Thr Lys Asn Arg His Ile Asn
            100                 105                 110

TAT GAA CAA TTC GCC TCC AAC CAG TGG AAT TCC ACA TGT ACG GGT GCT      384
Tyr Glu Gln Phe Ala Ser Asn Gln Trp Asn Ser Thr Cys Thr Gly Ala
        115                 120                 125

GAC AGA AAA ATT CCC TTC TCT GTC ATA CCC ACG GAC AAT GGA ACA AAA      432
Asp Arg Lys Ile Pro Phe Ser Val Ile Pro Thr Asp Asn Gly Thr Lys
    130                 135                 140

ATC TAT GGT CTT GAG TGG AAT GAT GAC TTT GTT ACA GCT TAT ATT AGT      480
Ile Tyr Gly Leu Glu Trp Asn Asp Asp Phe Val Thr Ala Tyr Ile Ser
145                 150                 155                 160

GGT CGT TCT TAT CAC TTG AAC ATC AAT ACT AAT TGG TTT AAC AAT GTC      528
Gly Arg Ser Tyr His Leu Asn Ile Asn Thr Asn Trp Phe Asn Asn Val
                165                 170                 175

ACA CTT TTG TAT TCA CGC AGC AGC ACT GCT ACC TGG GAG GCC              570
Thr Leu Leu Tyr Ser Arg Ser Ser Thr Ala Thr Trp Glu Ala
            180                 185                 190

TAG                                                                  573
```

(2) INFORMATION FOR SEQ ID NO:20:

(i) SEQUENCE CHARACTERISTICS:
(A) LENGTH: 190 amino acids
(B) TYPE: amino acid
(D) TOPOLOGY: linear (ii) MOLECULE TYPE: protein (xi) SEQUENCE DESCRIPTION: SEQ ID NO:20:

```
Met Asp Pro Glu Phe Gln Glu Lys Thr Gln Ser Leu Phe Ala Asn Ala
  1               5                  10                  15

Phe Gly Tyr Pro Ala Thr His Thr Ile Gln Gly Pro Gly Arg Val Asn
             20                  25                  30

Leu Ile Gly Glu His Thr Asp Tyr Asn Asp Gly Phe Val Leu Pro Cys
         35                  40                  45

Ala Ile Asp Tyr Gln Thr Val Ile Pro Asn Thr Arg Gly Thr Gly Asn
     50                  55                  60

Ala Arg Gly Lys Pro Leu Leu Phe His Val His Gly Glu Pro Val Ser
 65                  70                  75                  80

Val Ile Ile Tyr Ile Ser Ala Tyr Arg Asp Asp Val Gln Gln Arg Pro
                 85                  90                  95

Leu Leu Lys His Gly Leu Val Cys Ile Thr Lys Asn Arg His Ile Asn
            100                 105                 110

Tyr Glu Gln Phe Ala Ser Asn Gln Trp Asn Ser Thr Cys Thr Gly Ala
        115                 120                 125

Asp Arg Lys Ile Pro Phe Ser Val Ile Pro Thr Asp Asn Gly Thr Lys
    130                 135                 140

Ile Tyr Gly Leu Glu Trp Asn Asp Asp Phe Val Thr Ala Tyr Ile Ser
145                 150                 155                 160

Gly Arg Ser Tyr His Leu Asn Ile Asn Thr Asn Trp Phe Asn Asn Val
                165                 170                 175

Thr Leu Leu Tyr Ser Arg Ser Ser Thr Ala Thr Trp Glu Ala
            180                 185                 190
```

(2) INFORMATION FOR SEQ ID NO:21:

-continued (i) SEQUENCE CHARACTERISTICS:
(A) LENGTH: 4365 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..4362

(xi) SEQUENCE DESCRIPTION: SEQ ID NO:21:

```
ATG ATT GTG CTC GTA ACT TGC CTC TTG TTG TTA TGT TCA TAC CAC ACA       48
Met Ile Val Leu Val Thr Cys Leu Leu Leu Leu Cys Ser Tyr His Thr
  1               5                  10                  15

GTT TTG AGT ACA ACA AAT AAT GAA TGC ATA CAA GTT AAC GTA ACA CAA       96
Val Leu Ser Thr Thr Asn Asn Glu Cys Ile Gln Val Asn Val Thr Gln
             20                  25                  30

TTG GCT GGC AAT GAA AAC CTT ATC AGA GAT TTT CTG TTT AGT AAC TTT      144
Leu Ala Gly Asn Glu Asn Leu Ile Arg Asp Phe Leu Phe Ser Asn Phe
         35                  40                  45

AAA GAA GAA GGA AGT GTA GTT GTT GGT GGT TAT TAC CCT ACA GAG GTG      192
Lys Glu Glu Gly Ser Val Val Val Gly Gly Tyr Tyr Pro Thr Glu Val
     50                  55                  60

TGG TAC AAC TGC TCT AGA ACA GCA CAA ACT ACT GCC TTT CAG TAT TTT      240
Trp Tyr Asn Cys Ser Arg Thr Ala Gln Thr Thr Ala Phe Gln Tyr Phe
 65                  70                  75                  80

AAT AAT ATA CAT GCC TTT TAT TTT GTT ATG GAA GCC ATG GAA AAT AGC      288
Asn Asn Ile His Ala Phe Tyr Phe Val Met Glu Ala Met Glu Asn Ser
                 85                  90                  95

ACT GGT AAT GCA CGT GGT AAA CCA TTA TTA TTT CAT GTG CAT GGT GAG      336
Thr Gly Asn Ala Arg Gly Lys Pro Leu Leu Phe His Val His Gly Glu
            100                 105                 110

CCT GTT AGT GTT ATT ATA TAT ATA TCG GCT TAT AGG GAT GAT GTG CAA      384
Pro Val Ser Val Ile Ile Tyr Ile Ser Ala Tyr Arg Asp Asp Val Gln
        115                 120                 125

CAA AGG CCC CTT TTA AAA CAT GGG TTA GTG TGC ATA ACT AAA AAT CGC      432
Gln Arg Pro Leu Leu Lys His Gly Leu Val Cys Ile Thr Lys Asn Arg
    130                 135                 140

CAT ATT AAC TAT GAA CAA TTC ACC TCC AAC CAG TGG AAT TCC ACA TGT      480
His Ile Asn Tyr Glu Gln Phe Thr Ser Asn Gln Trp Asn Ser Thr Cys
145                 150                 155                 160

ACG GGT GCT GAC AGA AAA ATT CCT TTC TCT GTC ATA CCC ACG GAC AAT      528
Thr Gly Ala Asp Arg Lys Ile Pro Phe Ser Val Ile Pro Thr Asp Asn
                165                 170                 175

GGA ACA AAA ATC TAT GGT CTT GAG TGG AAT GAT GAC TTT GTT ACA GCT      576
Gly Thr Lys Ile Tyr Gly Leu Glu Trp Asn Asp Asp Phe Val Thr Ala
            180                 185                 190

TAT ATT AGT GGT CGT TCT TAT CAC TTG AAC ATC AAT ACT AAT TGG TTT      624
Tyr Ile Ser Gly Arg Ser Tyr His Leu Asn Ile Asn Thr Asn Trp Phe
        195                 200                 205

AAC AAT GTC ACA CTT TTG TAT TCA CGC TCA AGC ACT GCT ACC TGG GAA      672
Asn Asn Val Thr Leu Leu Tyr Ser Arg Ser Ser Thr Ala Thr Trp Glu
    210                 215                 220

TAC AGT GCT GCA TAT GCT TAC CAA GGT GTT TCT AAC TTC ACT TAT TAC      720
Tyr Ser Ala Ala Tyr Ala Tyr Gln Gly Val Ser Asn Phe Thr Tyr Tyr
225                 230                 235                 240

AAG TTA AAT AAC ACC AAT GGT CTA AAA ACC TAT GAA TTA TGT GAA GAT      768
Lys Leu Asn Asn Thr Asn Gly Leu Lys Thr Tyr Glu Leu Cys Glu Asp
                245                 250                 255

TAT GAA CAT TGC ACT GGC TAT GCT ACC AAT GTA TTT GCT CCG ACA TCA      816
```

-continued

```
Tyr Glu His Cys Thr Gly Tyr Ala Thr Asn Val Phe Ala Pro Thr Ser
            260                 265                 270

GGT GGT TAC ATA CCT GAT GGA TTT AGT TTT AAC AAT TGG TTC TTG CTT      864
Gly Gly Tyr Ile Pro Asp Gly Phe Ser Phe Asn Asn Trp Phe Leu Leu
        275                 280                 285

ACA AAT AGT TCC ACT TTT GTT AGT GGC AGG TTT GTA ACA AAT CAA CCA      912
Thr Asn Ser Ser Thr Phe Val Ser Gly Arg Phe Val Thr Asn Gln Pro
    290                 295                 300

TTA TTG ATT AAT TGC TTG TGG CCA GTG CCC AGT TTT GGT GTA GCA GCA      960
Leu Leu Ile Asn Cys Leu Trp Pro Val Pro Ser Phe Gly Val Ala Ala
305                 310                 315                 320

CAA GAA TTT TGT TTT GAA GGT GCA CAG TTT AGC CAA TGT AAT GGT GTG     1008
Gln Glu Phe Cys Phe Glu Gly Ala Gln Phe Ser Gln Cys Asn Gly Val
                325                 330                 335

TCT TTA AAT AAC ACA GTG GAT GTT ATT AGA TTC AAC CTT AAT TTC ACT     1056
Ser Leu Asn Asn Thr Val Asp Val Ile Arg Phe Asn Leu Asn Phe Thr
            340                 345                 350

GCA GAT GTA CAA TCT GGT ATG GGT GCT ACA GTA TTT TCA CTG AAT ACA     1104
Ala Asp Val Gln Ser Gly Met Gly Ala Thr Val Phe Ser Leu Asn Thr
        355                 360                 365

ACA GGT GGT GTC ATT CTT GAA ATT TCA TGT TAT AGT GAC ACA GTG AGT     1152
Thr Gly Gly Val Ile Leu Glu Ile Ser Cys Tyr Ser Asp Thr Val Ser
    370                 375                 380

GAG TCT AGT TCT TAC AGT TAT GGT GAA ATC CCG TTC GGC ATA ACT GAC     1200
Glu Ser Ser Ser Tyr Ser Tyr Gly Glu Ile Pro Phe Gly Ile Thr Asp
385                 390                 395                 400

GGA CCA CGA TAC TGT TAT GTA CTT TAC AAT GGC ACA GCT CTT AAA TAT     1248
Gly Pro Arg Tyr Cys Tyr Val Leu Tyr Asn Gly Thr Ala Leu Lys Tyr
                405                 410                 415

TTA GGA ACA TTA CCA CCC AGT GTA AAG GAA ATT GCT ATT AGT AAG TGG     1296
Leu Gly Thr Leu Pro Pro Ser Val Lys Glu Ile Ala Ile Ser Lys Trp
            420                 425                 430

GGC CAT TTT TAT ATT AAT GGT TAC AAT TTC TTT AGC ACA TTT CCT ATT     1344
Gly His Phe Tyr Ile Asn Gly Tyr Asn Phe Phe Ser Thr Phe Pro Ile
        435                 440                 445

GGT TGT ATA TCT TTT AAT TTA ACC ACT GGT GCT AGT GGA GCT TTT TGG     1392
Gly Cys Ile Ser Phe Asn Leu Thr Thr Gly Ala Ser Gly Ala Phe Trp
    450                 455                 460

ACA ATT GCT TAC ACA TCG TAT ACT GAA GCA TTA GTA CAA GTT GAA AAC     1440
Thr Ile Ala Tyr Thr Ser Tyr Thr Glu Ala Leu Val Gln Val Glu Asn
465                 470                 475                 480

ACA GCT ATT AAA AAT GTG ACG TAT TGT AAC AGT CAC ATT AAT AAC ATT     1488
Thr Ala Ile Lys Asn Val Thr Tyr Cys Asn Ser His Ile Asn Asn Ile
                485                 490                 495

AAA TGT TCT CAA CTT ACT GCT AAT TTG AAT AAT GGA TTT TAT CCT GTT     1536
Lys Cys Ser Gln Leu Thr Ala Asn Leu Asn Asn Gly Phe Tyr Pro Val
            500                 505                 510

GCT TCA AGT GAA GTA GGT TTC GTT AAT AAG AGT GTT GTG TTA TTA CCT     1584
Ala Ser Ser Glu Val Gly Phe Val Asn Lys Ser Val Val Leu Leu Pro
        515                 520                 525

AGC TTT TTC ACA CAC ACC GCT GTC AAT ATA ACC ATT GAT CTT GGT ATG     1632
Ser Phe Phe Thr His Thr Ala Val Asn Ile Thr Ile Asp Leu Gly Met
    530                 535                 540

AAG CTT AGT GGT TAT GGT CAA CCC ATA GCC TCG ACA CTA AGT AAC ATC     1680
Lys Leu Ser Gly Tyr Gly Gln Pro Ile Ala Ser Thr Leu Ser Asn Ile
545                 550                 555                 560

ACA CTA CCA ATG CAG GAT AAC AAT ACT GAT GTG TAC TGT ATT CGT TCT     1728
Thr Leu Pro Met Gln Asp Asn Asn Thr Asp Val Tyr Cys Ile Arg Ser
                565                 570                 575
```

-continued

```
AAC CAA TTC TCA GTT TAT GTT CCT TCC ACT TGC AAA AGT TCT TTA TGG     1776
Asn Gln Phe Ser Val Tyr Val Pro Ser Thr Cys Lys Ser Ser Leu Trp
            580                 585                 590

GAC AAT ATT TTT AAT CAA GAC TGC ACG GAT GTT TTA GAG GCT ACA GCT     1824
Asp Asn Ile Phe Asn Gln Asp Cys Thr Asp Val Leu Glu Ala Thr Ala
        595                 600                 605

GTT ATA AAA ACT GGT ACT TGT CCT TTC TCA TTT GAT AAA TTG AAC AAT     1872
Val Ile Lys Thr Gly Thr Cys Pro Phe Ser Phe Asp Lys Leu Asn Asn
    610                 615                 620

TAC TTG ACT TTT AAC AAG TTC TGT TTG TCG TTG AGT CCT GTT GGT GCT     1920
Tyr Leu Thr Phe Asn Lys Phe Cys Leu Ser Leu Ser Pro Val Gly Ala
625                 630                 635                 640

AAT TGC AAG TTT GAT GTT GCT GCA CGT ACA AGA ACC AAT GAG CAG GTT     1968
Asn Cys Lys Phe Asp Val Ala Ala Arg Thr Arg Thr Asn Glu Gln Val
                645                 650                 655

GTT AGA AGT CTA TAT GTA ATA TAT GAA GAA GGA GAC AAC ATA GTG GGT     2016
Val Arg Ser Leu Tyr Val Ile Tyr Glu Glu Gly Asp Asn Ile Val Gly
            660                 665                 670

GTA CCG TCT GAT AAT AGC GGT CTG CAC GAT TTG TCT GTG CTA CAC CTA     2064
Val Pro Ser Asp Asn Ser Gly Leu His Asp Leu Ser Val Leu His Leu
        675                 680                 685

GAC TCC TGT ACA GAT TAC AAT ATA TAT GGT AGA ACT GGT GTT GGT ATT     2112
Asp Ser Cys Thr Asp Tyr Asn Ile Tyr Gly Arg Thr Gly Val Gly Ile
    690                 695                 700

ATT AGA CGA ACT AAC AGT ACG CTA CTT AGT GGC TTA TAT TAC ACA TCA     2160
Ile Arg Arg Thr Asn Ser Thr Leu Leu Ser Gly Leu Tyr Tyr Thr Ser
705                 710                 715                 720

CTA TCA GGT GAT TTG TTA GGC TTT AAA AAT GTT AGT GAT GGT GTC ATT     2208
Leu Ser Gly Asp Leu Leu Gly Phe Lys Asn Val Ser Asp Gly Val Ile
                725                 730                 735

TAT TCT GTG ACG CCA TGT GAT GTA AGC GCA CAA GCG GCT GTT ATT GAT     2256
Tyr Ser Val Thr Pro Cys Asp Val Ser Ala Gln Ala Ala Val Ile Asp
            740                 745                 750

GGT GCC ATA GTT GGA GCT ATG ACT TCC ATT AAC AGT GAA CTG TTA GGT     2304
Gly Ala Ile Val Gly Ala Met Thr Ser Ile Asn Ser Glu Leu Leu Gly
        755                 760                 765

CTA ACA CAT TGG ACA ACG ACA CCT AAT TTT TAT TAC TAC TCT ATA TAT     2352
Leu Thr His Trp Thr Thr Thr Pro Asn Phe Tyr Tyr Tyr Ser Ile Tyr
    770                 775                 780

AAT TAC ACA AGT GAG AGG ACT CGT GGC ACT GCA ATT GAC AGT AAC GAT     2400
Asn Tyr Thr Ser Glu Arg Thr Arg Gly Thr Ala Ile Asp Ser Asn Asp
785                 790                 795                 800

GTT GAT TGT GAA CCT GTC ATA ACC TAT TCT AAT ATA GGT GTT TGT AAA     2448
Val Asp Cys Glu Pro Val Ile Thr Tyr Ser Asn Ile Gly Val Cys Lys
                805                 810                 815

AAT GGT GCT TTG GTT TTT ATT AAC GTC ACA CAT TCT GAC GGA GAC GTG     2496
Asn Gly Ala Leu Val Phe Ile Asn Val Thr His Ser Asp Gly Asp Val
            820                 825                 830

CAA CCA ATT AGC ACT GGT AAT GTC ACG ATA CCT ACA AAT TTT ACC ATA     2544
Gln Pro Ile Ser Thr Gly Asn Val Thr Ile Pro Thr Asn Phe Thr Ile
        835                 840                 845

TCT GTG CAA GTT GAA TAC ATG CAG GTT TAC ACT ACA CCA GTA TCA ATA     2592
Ser Val Gln Val Glu Tyr Met Gln Val Tyr Thr Thr Pro Val Ser Ile
    850                 855                 860

GAT TGT GCA AGA TAC GTT TGT AAT GGT AAC CCT AGA TGT AAC AAA TTG     2640
Asp Cys Ala Arg Tyr Val Cys Asn Gly Asn Pro Arg Cys Asn Lys Leu
865                 870                 875                 880

TTA ACA CAA TAT GTG TCT GCA TGT CAA ACT ATT GAA CAA GCA CTT GCA     2688
Leu Thr Gln Tyr Val Ser Ala Cys Gln Thr Ile Glu Gln Ala Leu Ala
                885                 890                 895
```

-continued

```
ATG GGT GCC AGA CTT GAA AAC ATG GAG GTT GAT TCC ATG TTG TTT GTC     2736
Met Gly Ala Arg Leu Glu Asn Met Glu Val Asp Ser Met Leu Phe Val
            900                 905                 910

TCG GAA AAT GCC CTT AAA TTG GCA TCT GTT GAG GCG TTC AAT AGT ACA     2784
Ser Glu Asn Ala Leu Lys Leu Ala Ser Val Glu Ala Phe Asn Ser Thr
        915                 920                 925

GAA AAT TTA GAT CCT ATT TAC AAA GAA TGG CCT AGC ATA GGT GGT TCT     2832
Glu Asn Leu Asp Pro Ile Tyr Lys Glu Trp Pro Ser Ile Gly Gly Ser
    930                 935                 940

TGG CTA GGA GGT CTA AAA GAT ATA CTA CCG TCC CAT AAT AGC AAA CGT     2880
Trp Leu Gly Gly Leu Lys Asp Ile Leu Pro Ser His Asn Ser Lys Arg
945                 950                 955                 960

AAG TAT GGT TCT GCT ATA GAA GAT TTG CTT TTT GAT AAA GTT GTA ACA     2928
Lys Tyr Gly Ser Ala Ile Glu Asp Leu Leu Phe Asp Lys Val Val Thr
                965                 970                 975

TCT GGT TTA GGT ACA GTT GAT GAA GAT TAT AAA CGT TGT ACT GGT GGT     2976
Ser Gly Leu Gly Thr Val Asp Glu Asp Tyr Lys Arg Cys Thr Gly Gly
            980                 985                 990

TAC GAC ATA GCA GAC TTG GTG TGT GCT CAA TAT TAC AAT GGC ATC ATG     3024
Tyr Asp Ile Ala Asp Leu Val Cys Ala Gln Tyr Tyr Asn Gly Ile Met
        995                 1000                1005

GTT CTA CCA GGT GTA GCT AAT GCT GAC AAG ATG ACT ATG TAC ACA GCA     3072
Val Leu Pro Gly Val Ala Asn Ala Asp Lys Met Thr Met Tyr Thr Ala
    1010                1015                1020

TCA CTT GCA GGT GGT ATA ACA TTA GGT GCA CTT GGT GGT GGC GCC GTG     3120
Ser Leu Ala Gly Gly Ile Thr Leu Gly Ala Leu Gly Gly Gly Ala Val
1025                1030                1035                1040

GCT ATA CCT TTT GCA GTA GCA GTA CAG GCT AGA CTT AAT TAT GTT GCT     3168
Ala Ile Pro Phe Ala Val Ala Val Gln Ala Arg Leu Asn Tyr Val Ala
                1045                1050                1055

CTA CAA ACT GAT GTA TTG AAT AAA AAC CAA CAG ATC CTG GCT AAT GCT     3216
Leu Gln Thr Asp Val Leu Asn Lys Asn Gln Gln Ile Leu Ala Asn Ala
            1060                1065                1070

TTC AAT CAA GCT ATT GGT AAC ATT ACA CAG GCT TTT GGT AAG GTT AAT     3264
Phe Asn Gln Ala Ile Gly Asn Ile Thr Gln Ala Phe Gly Lys Val Asn
        1075                1080                1085

GAT GCT ATA CAT CAA ACA TCA CAA GGT CTT GCC ACT GTT GCT AAA GCG     3312
Asp Ala Ile His Gln Thr Ser Gln Gly Leu Ala Thr Val Ala Lys Ala
    1090                1095                1100

TTG GCA AAA GTG CAA GAT GTT GTC AAC ACA CAA GGG CAA GCT TTA AGT     3360
Leu Ala Lys Val Gln Asp Val Val Asn Thr Gln Gly Gln Ala Leu Ser
1105                1110                1115                1120

CAC CTT ACA GTA CAA TTG CAA AAT AAT TTT CAA GCC ATT AGT AGT TCT     3408
His Leu Thr Val Gln Leu Gln Asn Asn Phe Gln Ala Ile Ser Ser Ser
                1125                1130                1135

ATT AGT GAT ATT TAT AAC AGG CTT GAC GAA CTG AGT GCT GAT GCA CAA     3456
Ile Ser Asp Ile Tyr Asn Arg Leu Asp Glu Leu Ser Ala Asp Ala Gln
            1140                1145                1150

GTT GAT AGG CTG ATT ACA GGT AGA CTT ACA GCA CTT AAT GCA TTT GTG     3504
Val Asp Arg Leu Ile Thr Gly Arg Leu Thr Ala Leu Asn Ala Phe Val
        1155                1160                1165

TCT CAG ACT CTA ACC AGA CAA GCA GAG GTT AGG GCT AGT AGA CAA CTT     3552
Ser Gln Thr Leu Thr Arg Gln Ala Glu Val Arg Ala Ser Arg Gln Leu
    1170                1175                1180

GCC AAA GAC AAG GTT AAT GAA TGT GTT AGG TCT CAG TCT CAG AGA TTC     3600
Ala Lys Asp Lys Val Asn Glu Cys Val Arg Ser Gln Ser Gln Arg Phe
1185                1190                1195                1200

GGA TTC TGT GGT AAT GGT ACA CAT TTG TTT TCA CTA GCA AAT GCA GCA     3648
Gly Phe Cys Gly Asn Gly Thr His Leu Phe Ser Leu Ala Asn Ala Ala
```

-continued

```
                1205                1210                1215

CCA AAT GGC ATG ATT TTC TTT CAT ACA GTA CTA TTA CCA ACA GCT TAT      3696
Pro Asn Gly Met Ile Phe Phe His Thr Val Leu Leu Pro Thr Ala Tyr
            1220                1225                1230

GAA ACT GTA ACA GCT TGG TCA GGT ATT TGT GCT TCA GAT GGC GAT CGC      3744
Glu Thr Val Thr Ala Trp Ser Gly Ile Cys Ala Ser Asp Gly Asp Arg
        1235                1240                1245

ACT TTC GGA CTT GTC GTT AAA GAT GTG CAG TTG ACG TTG TTT CGT AAT      3792
Thr Phe Gly Leu Val Val Lys Asp Val Gln Leu Thr Leu Phe Arg Asn
    1250                1255                1260

CTA GAT GAC AAG TTC TAT TTG ACC CCC AGA ACT ATG TAT CAG CCT AGA      3840
Leu Asp Asp Lys Phe Tyr Leu Thr Pro Arg Thr Met Tyr Gln Pro Arg
1265                1270                1275                1280

GTT GCA ACT AGT TCT GAT TTT GTT CAA ATT GAA GGG TGT GAT GTG TTG      3888
Val Ala Thr Ser Ser Asp Phe Val Gln Ile Glu Gly Cys Asp Val Leu
                1285                1290                1295

TTT GTC AAC GCG ACT GTA ATT GAT TTG CCT AGT ATT ATA CCT GAC TAT      3936
Phe Val Asn Ala Thr Val Ile Asp Leu Pro Ser Ile Ile Pro Asp Tyr
            1300                1305                1310

ATT GAC ATT AAT CAA ACT GTT CAA GAC ATA TTA GAA AAT TAC AGA CCA      3984
Ile Asp Ile Asn Gln Thr Val Gln Asp Ile Leu Glu Asn Tyr Arg Pro
        1315                1320                1325

AAC TGG ACT GTA CCT GAA TTT ACA CTT GAT ATT TTC AAC GCA ACC TAT      4032
Asn Trp Thr Val Pro Glu Phe Thr Leu Asp Ile Phe Asn Ala Thr Tyr
    1330                1335                1340

TTA AAT CTG ACT GGT GAA ATT GAT GAC TTA GAG TTT AGG TCA GAA AAG      4080
Leu Asn Leu Thr Gly Glu Ile Asp Asp Leu Glu Phe Arg Ser Glu Lys
1345                1350                1355                1360

CTA CAT AAC ACT ACA GTA GAA CTT GCC ATT CTC ATT GAT ACC ATT AAT      4128
Leu His Asn Thr Thr Val Glu Leu Ala Ile Leu Ile Asp Thr Ile Asn
                1365                1370                1375

AAT ACA TTA GTC AAT CTT GAA TGG CTC AAT AGA ATT GAA ACT TAT GTA      4176
Asn Thr Leu Val Asn Leu Glu Trp Leu Asn Arg Ile Glu Thr Tyr Val
            1380                1385                1390

AAA TGG CCT TGG TAT GTG TGG CTA CTG ATA GGT CTA GTA GTA GTA TTT      4224
Lys Trp Pro Trp Tyr Val Trp Leu Leu Ile Gly Leu Val Val Val Phe
        1395                1400                1405

TGC ATA CCA TTA CTG CTA TTT TGC TGT TTT AGC ACA GGT TGT TGT GGA      4272
Cys Ile Pro Leu Leu Leu Phe Cys Cys Phe Ser Thr Gly Cys Cys Gly
    1410                1415                1420

TGC ATA GGT TGT TTA GGA AGT TGT TGT CAC TCT ATA TGT AGT AGA AGA      4320
Cys Ile Gly Cys Leu Gly Ser Cys Cys His Ser Ile Cys Ser Arg Arg
1425                1430                1435                1440

CAA TTT GAA TAT TAT GAA CCA ATT GAA AAA GTG CAT GTC CAC              4362
Gln Phe Glu Tyr Tyr Glu Pro Ile Glu Lys Val His Val His
                1445                1450

TAA                                                                  4365
```

(2) INFORMATION FOR SEQ ID NO:22:

(i) SEQUENCE CHARACTERISTICS:
(A) LENGTH: 1454 amino acids
(B) TYPE: amino acid
(D) TOPOLOGY: linear (ii) MOLECULE TYPE: protein (xi) SEQUENCE DESCRIPTION: SEQ ID NO:22:

```
Met Ile Val Leu Val Thr Cys Leu Leu Leu Leu Cys Ser Tyr His Thr
  1               5                  10                  15
```

-continued

```
Val Leu Ser Thr Thr Asn Asn Glu Cys Ile Gln Val Asn Val Thr Gln
            20                  25                  30

Leu Ala Gly Asn Glu Asn Leu Ile Arg Asp Phe Leu Phe Ser Asn Phe
        35                  40                  45

Lys Glu Glu Gly Ser Val Val Val Gly Gly Tyr Tyr Pro Thr Glu Val
    50                  55                  60

Trp Tyr Asn Cys Ser Arg Thr Ala Gln Thr Thr Ala Phe Gln Tyr Phe
65                  70                  75                  80

Asn Asn Ile His Ala Phe Tyr Phe Val Met Glu Ala Met Glu Asn Ser
                85                  90                  95

Thr Gly Asn Ala Arg Gly Lys Pro Leu Leu Phe His Val His Gly Glu
            100                 105                 110

Pro Val Ser Val Ile Ile Tyr Ile Ser Ala Tyr Arg Asp Asp Val Gln
        115                 120                 125

Gln Arg Pro Leu Leu Lys His Gly Leu Val Cys Ile Thr Lys Asn Arg
    130                 135                 140

His Ile Asn Tyr Glu Gln Phe Thr Ser Asn Gln Trp Asn Ser Thr Cys
145                 150                 155                 160

Thr Gly Ala Asp Arg Lys Ile Pro Phe Ser Val Ile Pro Thr Asp Asn
                165                 170                 175

Gly Thr Lys Ile Tyr Gly Leu Glu Trp Asn Asp Asp Phe Val Thr Ala
            180                 185                 190

Tyr Ile Ser Gly Arg Ser Tyr His Leu Asn Ile Asn Thr Asn Trp Phe
        195                 200                 205

Asn Asn Val Thr Leu Leu Tyr Ser Arg Ser Ser Thr Ala Thr Trp Glu
    210                 215                 220

Tyr Ser Ala Ala Tyr Ala Tyr Gln Gly Val Ser Asn Phe Thr Tyr Tyr
225                 230                 235                 240

Lys Leu Asn Asn Thr Asn Gly Leu Lys Thr Tyr Glu Leu Cys Glu Asp
                245                 250                 255

Tyr Glu His Cys Thr Gly Tyr Ala Thr Asn Val Phe Ala Pro Thr Ser
            260                 265                 270

Gly Gly Tyr Ile Pro Asp Gly Phe Ser Phe Asn Asn Trp Phe Leu Leu
        275                 280                 285

Thr Asn Ser Ser Thr Phe Val Ser Gly Arg Phe Val Thr Asn Gln Pro
    290                 295                 300

Leu Leu Ile Asn Cys Leu Trp Pro Val Pro Ser Phe Gly Val Ala Ala
305                 310                 315                 320

Gln Glu Phe Cys Phe Glu Gly Ala Gln Phe Ser Gln Cys Asn Gly Val
                325                 330                 335

Ser Leu Asn Asn Thr Val Asp Val Ile Arg Phe Asn Leu Asn Phe Thr
            340                 345                 350

Ala Asp Val Gln Ser Gly Met Gly Ala Thr Val Phe Ser Leu Asn Thr
        355                 360                 365

Thr Gly Gly Val Ile Leu Glu Ile Ser Cys Tyr Ser Asp Thr Val Ser
    370                 375                 380

Glu Ser Ser Ser Tyr Ser Tyr Gly Glu Ile Pro Phe Gly Ile Thr Asp
385                 390                 395                 400

Gly Pro Arg Tyr Cys Tyr Val Leu Tyr Asn Gly Thr Ala Leu Lys Tyr
                405                 410                 415

Leu Gly Thr Leu Pro Pro Ser Val Lys Glu Ile Ala Ile Ser Lys Trp
            420                 425                 430

Gly His Phe Tyr Ile Asn Gly Tyr Asn Phe Phe Ser Thr Phe Pro Ile
```

-continued

```
        435                 440                 445

Gly Cys Ile Ser Phe Asn Leu Thr Thr Gly Ala Ser Gly Ala Phe Trp
    450                 455                 460

Thr Ile Ala Tyr Thr Ser Tyr Thr Glu Ala Leu Val Gln Val Glu Asn
465                 470                 475                 480

Thr Ala Ile Lys Asn Val Thr Tyr Cys Asn Ser His Ile Asn Asn Ile
                485                 490                 495

Lys Cys Ser Gln Leu Thr Ala Asn Leu Asn Asn Gly Phe Tyr Pro Val
            500                 505                 510

Ala Ser Ser Glu Val Gly Phe Val Asn Lys Ser Val Val Leu Leu Pro
        515                 520                 525

Ser Phe Phe Thr His Thr Ala Val Asn Ile Thr Ile Asp Leu Gly Met
    530                 535                 540

Lys Leu Ser Gly Tyr Gly Gln Pro Ile Ala Ser Thr Leu Ser Asn Ile
545                 550                 555                 560

Thr Leu Pro Met Gln Asp Asn Asn Thr Asp Val Tyr Cys Ile Arg Ser
                565                 570                 575

Asn Gln Phe Ser Val Tyr Val Pro Ser Thr Cys Lys Ser Ser Leu Trp
            580                 585                 590

Asp Asn Ile Phe Asn Gln Asp Cys Thr Asp Val Leu Glu Ala Thr Ala
        595                 600                 605

Val Ile Lys Thr Gly Thr Cys Pro Phe Ser Phe Asp Lys Leu Asn Asn
    610                 615                 620

Tyr Leu Thr Phe Asn Lys Phe Cys Leu Ser Leu Ser Pro Val Gly Ala
625                 630                 635                 640

Asn Cys Lys Phe Asp Val Ala Ala Arg Thr Arg Thr Asn Glu Gln Val
                645                 650                 655

Val Arg Ser Leu Tyr Val Ile Tyr Glu Glu Gly Asp Asn Ile Val Gly
            660                 665                 670

Val Pro Ser Asp Asn Ser Gly Leu His Asp Leu Ser Val Leu His Leu
        675                 680                 685

Asp Ser Cys Thr Asp Tyr Asn Ile Tyr Gly Arg Thr Gly Val Gly Ile
    690                 695                 700

Ile Arg Arg Thr Asn Ser Thr Leu Leu Ser Gly Leu Tyr Tyr Thr Ser
705                 710                 715                 720

Leu Ser Gly Asp Leu Leu Gly Phe Lys Asn Val Ser Asp Gly Val Ile
                725                 730                 735

Tyr Ser Val Thr Pro Cys Asp Val Ser Ala Gln Ala Ala Val Ile Asp
            740                 745                 750

Gly Ala Ile Val Gly Ala Met Thr Ser Ile Asn Ser Glu Leu Leu Gly
        755                 760                 765

Leu Thr His Trp Thr Thr Thr Pro Asn Phe Tyr Tyr Tyr Ser Ile Tyr
    770                 775                 780

Asn Tyr Thr Ser Glu Arg Thr Arg Gly Thr Ala Ile Asp Ser Asn Asp
785                 790                 795                 800

Val Asp Cys Glu Pro Val Ile Thr Tyr Ser Asn Ile Gly Val Cys Lys
                805                 810                 815

Asn Gly Ala Leu Val Phe Ile Asn Val Thr His Ser Asp Gly Asp Val
            820                 825                 830

Gln Pro Ile Ser Thr Gly Asn Val Thr Ile Pro Thr Asn Phe Thr Ile
        835                 840                 845

Ser Val Gln Val Glu Tyr Met Gln Val Tyr Thr Thr Pro Val Ser Ile
    850                 855                 860
```

-continued

Asp Cys Ala Arg Tyr Val Cys Asn Gly Asn Pro Arg Cys Asn Lys Leu
865 870 875 880

Leu Thr Gln Tyr Val Ser Ala Cys Gln Thr Ile Glu Gln Ala Leu Ala
885 890 895

Met Gly Ala Arg Leu Glu Asn Met Glu Val Asp Ser Met Leu Phe Val
900 905 910

Ser Glu Asn Ala Leu Lys Leu Ala Ser Val Glu Ala Phe Asn Ser Thr
915 920 925

Glu Asn Leu Asp Pro Ile Tyr Lys Glu Trp Pro Ser Ile Gly Gly Ser
930 935 940

Trp Leu Gly Gly Leu Lys Asp Ile Leu Pro Ser His Asn Ser Lys Arg
945 950 955 960

Lys Tyr Gly Ser Ala Ile Glu Asp Leu Leu Phe Asp Lys Val Val Thr
965 970 975

Ser Gly Leu Gly Thr Val Asp Glu Asp Tyr Lys Arg Cys Thr Gly Gly
980 985 990

Tyr Asp Ile Ala Asp Leu Val Cys Ala Gln Tyr Tyr Asn Gly Ile Met
995 1000 1005

Val Leu Pro Gly Val Ala Asn Ala Asp Lys Met Thr Met Tyr Thr Ala
1010 1015 1020

Ser Leu Ala Gly Gly Ile Thr Leu Gly Ala Leu Gly Gly Gly Ala Val
1025 1030 1035 1040

Ala Ile Pro Phe Ala Val Ala Val Gln Ala Arg Leu Asn Tyr Val Ala
1045 1050 1055

Leu Gln Thr Asp Val Leu Asn Lys Asn Gln Gln Ile Leu Ala Asn Ala
1060 1065 1070

Phe Asn Gln Ala Ile Gly Asn Ile Thr Gln Ala Phe Gly Lys Val Asn
1075 1080 1085

Asp Ala Ile His Gln Thr Ser Gln Gly Leu Ala Thr Val Ala Lys Ala
1090 1095 1100

Leu Ala Lys Val Gln Asp Val Val Asn Thr Gln Gly Gln Ala Leu Ser
1105 1110 1115 1120

His Leu Thr Val Gln Leu Gln Asn Asn Phe Gln Ala Ile Ser Ser Ser
1125 1130 1135

Ile Ser Asp Ile Tyr Asn Arg Leu Asp Glu Leu Ser Ala Asp Ala Gln
1140 1145 1150

Val Asp Arg Leu Ile Thr Gly Arg Leu Thr Ala Leu Asn Ala Phe Val
1155 1160 1165

Ser Gln Thr Leu Thr Arg Gln Ala Glu Val Arg Ala Ser Arg Gln Leu
1170 1175 1180

Ala Lys Asp Lys Val Asn Glu Cys Val Arg Ser Gln Ser Gln Arg Phe
1185 1190 1195 1200

Gly Phe Cys Gly Asn Gly Thr His Leu Phe Ser Leu Ala Asn Ala Ala
1205 1210 1215

Pro Asn Gly Met Ile Phe Phe His Thr Val Leu Leu Pro Thr Ala Tyr
1220 1225 1230

Glu Thr Val Thr Ala Trp Ser Gly Ile Cys Ala Ser Asp Gly Asp Arg
1235 1240 1245

Thr Phe Gly Leu Val Val Lys Asp Val Gln Leu Thr Leu Phe Arg Asn
1250 1255 1260

Leu Asp Asp Lys Phe Tyr Leu Thr Pro Arg Thr Met Tyr Gln Pro Arg
1265 1270 1275 1280

-continued

```
Val Ala Thr Ser Ser Asp Phe Val Gln Ile Glu Gly Cys Asp Val Leu
                1285                1290                1295

Phe Val Asn Ala Thr Val Ile Asp Leu Pro Ser Ile Ile Pro Asp Tyr
            1300                1305                1310

Ile Asp Ile Asn Gln Thr Val Gln Asp Ile Leu Glu Asn Tyr Arg Pro
        1315                1320                1325

Asn Trp Thr Val Pro Glu Phe Thr Leu Asp Ile Phe Asn Ala Thr Tyr
    1330                1335                1340

Leu Asn Leu Thr Gly Glu Ile Asp Asp Leu Glu Phe Arg Ser Glu Lys
1345                1350                1355                1360

Leu His Asn Thr Thr Val Glu Leu Ala Ile Leu Ile Asp Thr Ile Asn
                1365                1370                1375

Asn Thr Leu Val Asn Leu Glu Trp Leu Asn Arg Ile Glu Thr Tyr Val
            1380                1385                1390

Lys Trp Pro Trp Tyr Val Trp Leu Leu Ile Gly Leu Val Val Val Phe
        1395                1400                1405

Cys Ile Pro Leu Leu Leu Phe Cys Cys Phe Ser Thr Gly Cys Cys Gly
    1410                1415                1420

Cys Ile Gly Cys Leu Gly Ser Cys Cys His Ser Ile Cys Ser Arg Arg
1425                1430                1435                1440

Gln Phe Glu Tyr Tyr Glu Pro Ile Glu Lys Val His Val His
                1445                1450
```

(2) INFORMATION FOR SEQ ID NO:23:

(i) SEQUENCE CHARACTERISTICS:
(A) LENGTH: 2246 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..2244

(xi) SEQUENCE DESCRIPTION: SEQ ID NO:23:

```
ATG ATT GTG CTC GTA ACT TGC CTC TTG TTG TTA TGT TCA TAC CAC ACA       48
Met Ile Val Leu Val Thr Cys Leu Leu Leu Leu Cys Ser Tyr His Thr
  1               5                  10                  15

GTT TTG AGT ACA ACA AAT AAT GAA TGC ATA CAA GTT AAC GTA ACA CAA       96
Val Leu Ser Thr Thr Asn Asn Glu Cys Ile Gln Val Asn Val Thr Gln
             20                  25                  30

TTG GCT GGC AAT GAA AAC CTT ATC AGA GAT TTT CTG TTT AGT AAC TTT      144
Leu Ala Gly Asn Glu Asn Leu Ile Arg Asp Phe Leu Phe Ser Asn Phe
         35                  40                  45

AAA GAA GAA GGA AGT GTA GTT GTT GGT GGT TAT TAC CCT ACA GAG GTG      192
Lys Glu Glu Gly Ser Val Val Val Gly Gly Tyr Tyr Pro Thr Glu Val
     50                  55                  60

TGG TAC AAC TGC TCT AGA ACA GCT CGA ACT ACT GCC TTT CAG TAT TTT      240
Trp Tyr Asn Cys Ser Arg Thr Ala Arg Thr Thr Ala Phe Gln Tyr Phe
 65                  70                  75                  80

AAT AAT ATA CAT GCC TTT TAT TTT GTT ATG GAA GCC ATG GAA AAT AGC      288
Asn Asn Ile His Ala Phe Tyr Phe Val Met Glu Ala Met Glu Asn Ser
                 85                  90                  95

ACT GGT AAT GCA CGT GGT AAA CCA TTA TTA TTT CAT GTG CAT GGT GAG      336
Thr Gly Asn Ala Arg Gly Lys Pro Leu Leu Phe His Val His Gly Glu
            100                 105                 110

CCT GTT AGT GTT ATT ATA TAT ATA TCG GCT TAT AGG GAT GAT GTG CAA      384
```

-continued

```
Pro Val Ser Val Ile Ile Tyr Ile Ser Ala Tyr Arg Asp Asp Val Gln
        115                 120                 125

CAA AGG CCC CTT TTA GAA CAT GGG TTA GTG TGC ATA ACT AAA AAT CGC      432
Gln Arg Pro Leu Leu Glu His Gly Leu Val Cys Ile Thr Lys Asn Arg
    130                 135                 140

CAT ATT AAC TAT GAA CAA TTC ACC TCC AAC CAG TGG AAT TCC ACA TGT      480
His Ile Asn Tyr Glu Gln Phe Thr Ser Asn Gln Trp Asn Ser Thr Cys
145                 150                 155                 160

ACG GGT GCT GAC AGA AAA ATT CCT TTC TCT GTC ATA CCC ACG GAC AAT      528
Thr Gly Ala Asp Arg Lys Ile Pro Phe Ser Val Ile Pro Thr Asp Asn
                165                 170                 175

GGA ACA AAA ATC TAT GGT CTT GAG TGG AAT GAT GAC TTT GTT ACA GCT      576
Gly Thr Lys Ile Tyr Gly Leu Glu Trp Asn Asp Asp Phe Val Thr Ala
            180                 185                 190

TAT ATT AGT GGT CGT TCT TAT CAC TTG AAC ATC AAT ACT AAT TGG TTT      624
Tyr Ile Ser Gly Arg Ser Tyr His Leu Asn Ile Asn Thr Asn Trp Phe
        195                 200                 205

AAC AAT GTC ACA CTT TTG TAT TCA CGC TCA AGC ACT GCT ACC TGG GAA      672
Asn Asn Val Thr Leu Leu Tyr Ser Arg Ser Ser Thr Ala Thr Trp Glu
    210                 215                 220

TAC AGT GCT GCA TAT GCT TAC CAA GGT GTT TCT AAC TTC ACT TAT TAC      720
Tyr Ser Ala Ala Tyr Ala Tyr Gln Gly Val Ser Asn Phe Thr Tyr Tyr
225                 230                 235                 240

AAG TTA AAT AAC ACC AAT GGT CTA AAA ACC TAT GAA TTA TGT GAA GAT      768
Lys Leu Asn Asn Thr Asn Gly Leu Lys Thr Tyr Glu Leu Cys Glu Asp
                245                 250                 255

TAT GAA CAT TGC ACT GGC TAT GCT ACC AAT GTA TTT GCT CCG ACA TCA      816
Tyr Glu His Cys Thr Gly Tyr Ala Thr Asn Val Phe Ala Pro Thr Ser
            260                 265                 270

GGT GGT TAC ATA CCT GAT GGA TTT AGT TTT AAT AAT TGG TTC TTG CTT      864
Gly Gly Tyr Ile Pro Asp Gly Phe Ser Phe Asn Asn Trp Phe Leu Leu
        275                 280                 285

ACA AAT AGT TCC ACT TTT GTT AGT GGC AGG TTT GTA ACA AAT CAA CCA      912
Thr Asn Ser Ser Thr Phe Val Ser Gly Arg Phe Val Thr Asn Gln Pro
    290                 295                 300

TTA TTG ATT AAT TGC TTG TGG CCA GTG CCC AGT TTT GGT GTA GCA GCA      960
Leu Leu Ile Asn Cys Leu Trp Pro Val Pro Ser Phe Gly Val Ala Ala
305                 310                 315                 320

CAA GAA TTT TGT TTT GAA GGT GCA CAG TTT AGC CAA TGT AAT GGT GTG     1008
Gln Glu Phe Cys Phe Glu Gly Ala Gln Phe Ser Gln Cys Asn Gly Val
                325                 330                 335

TCT TTA AAT AAC ACA GTG GAT GTT ATT AGA TTC AAC CTT AAT TTC ACT     1056
Ser Leu Asn Asn Thr Val Asp Val Ile Arg Phe Asn Leu Asn Phe Thr
            340                 345                 350

GCA GAT GTA CAA TCT GGT ATG GGT GCC ACA GTA TTT TCA CTG AAT ACA     1104
Ala Asp Val Gln Ser Gly Met Gly Ala Thr Val Phe Ser Leu Asn Thr
        355                 360                 365

ACA GGT GGT GTC ATT CTT GAA ATT TCA TGT TAT AGT GAC ACA GTG AGT     1152
Thr Gly Gly Val Ile Leu Glu Ile Ser Cys Tyr Ser Asp Thr Val Ser
    370                 375                 380

GAG TCT AGT TCT TAC AGT TAT GGT GAA ATC CCG TTC GGC ATA ACT GAC     1200
Glu Ser Ser Ser Tyr Ser Tyr Gly Glu Ile Pro Phe Gly Ile Thr Asp
385                 390                 395                 400

GGA CCA CGA TAC TGT TAT GTA CTT TAC AAT GGC ACA GCT CTT AAA TAT     1248
Gly Pro Arg Tyr Cys Tyr Val Leu Tyr Asn Gly Thr Ala Leu Lys Tyr
                405                 410                 415

TTA GGA ACA TTA CCA CCC AGT GTA AAG GAA ATT GCT ATT AGT AAG TGG     1296
Leu Gly Thr Leu Pro Pro Ser Val Lys Glu Ile Ala Ile Ser Lys Trp
            420                 425                 430
```

-continued

```
GGC CAT TTT TAT ATT AAT GGT TAC AAT TTC TTT AGC ACA TTT CCT ATT        1344
Gly His Phe Tyr Ile Asn Gly Tyr Asn Phe Phe Ser Thr Phe Pro Ile
        435                 440                 445

GGT TGT ATA TCT TTT AAT TTA ACC ACT GGT GTT AGT GGA GCT TTT TGG        1392
Gly Cys Ile Ser Phe Asn Leu Thr Thr Gly Val Ser Gly Ala Phe Trp
    450                 455                 460

ACA ATT GCT TAC ACA TCG TAT ACT GAA GCA TTA GTA CAA GTT GAA AAC        1440
Thr Ile Ala Tyr Thr Ser Tyr Thr Glu Ala Leu Val Gln Val Glu Asn
465                 470                 475                 480

ACA GCT ATT AAA AAT GTG ACG TAT TGT AAC AGT CAC ATT AAT AAC ATT        1488
Thr Ala Ile Lys Asn Val Thr Tyr Cys Asn Ser His Ile Asn Asn Ile
                485                 490                 495

AAA TGT TCT CAA CTT ACT GCT AAT TTG AAT AAT GGA TTT TAT CCT GTT        1536
Lys Cys Ser Gln Leu Thr Ala Asn Leu Asn Asn Gly Phe Tyr Pro Val
            500                 505                 510

GCT TCA AGT GAA GTA GGT TTC GTT AAT AAG AGT GTT GTG TTA TTA CCT        1584
Ala Ser Ser Glu Val Gly Phe Val Asn Lys Ser Val Val Leu Leu Pro
        515                 520                 525

AGC TTT TTC ACA TAC ACC GCT GTC AAT ATA ACC ATT GAT CTT GGT ATG        1632
Ser Phe Phe Thr Tyr Thr Ala Val Asn Ile Thr Ile Asp Leu Gly Met
    530                 535                 540

AAG CTT AGT GGT TAT GGT CAA CCC ATA GCC TCG ACA CTA AGT AAC ATC        1680
Lys Leu Ser Gly Tyr Gly Gln Pro Ile Ala Ser Thr Leu Ser Asn Ile
545                 550                 555                 560

ACA CTA CCA ATG CAG GAT AAC AAT ACT GAT GTG TAC TGT ATT CGT TCT        1728
Thr Leu Pro Met Gln Asp Asn Asn Thr Asp Val Tyr Cys Ile Arg Ser
                565                 570                 575

AAC CAA TTC TCA GTT TAT GTT CAT TCC ACT TGC AAA AGT TCT TTA TGG        1776
Asn Gln Phe Ser Val Tyr Val His Ser Thr Cys Lys Ser Ser Leu Trp
            580                 585                 590

GAC AAT ATC TTT AAT CAA GAC TGC ACG GAT GTT TTA GAG GCT ACA GCT        1824
Asp Asn Ile Phe Asn Gln Asp Cys Thr Asp Val Leu Glu Ala Thr Ala
        595                 600                 605

GTT ATA AAA ACT GGT ACT TGT CCT TTC TCA TTT GAT AAA TTG AAC AAT        1872
Val Ile Lys Thr Gly Thr Cys Pro Phe Ser Phe Asp Lys Leu Asn Asn
    610                 615                 620

TAC TTG ACT TTT AAC AAG TTC TGT TTG TCG TTG AGT CCT GTT GGT GCT        1920
Tyr Leu Thr Phe Asn Lys Phe Cys Leu Ser Leu Ser Pro Val Gly Ala
625                 630                 635                 640

AAT TGC AAG TTT GAT GTT GCT GCA CGT ACA AGA ACC AAT GAG CAG GTT        1968
Asn Cys Lys Phe Asp Val Ala Ala Arg Thr Arg Thr Asn Glu Gln Val
                645                 650                 655

GTT AGA AGT CTA TAT GTA ATA TAT GAA GAA GGA GAC AAC ATA GTG GGT        2016
Val Arg Ser Leu Tyr Val Ile Tyr Glu Glu Gly Asp Asn Ile Val Gly
            660                 665                 670

GTA CCG TCT GAT GAT AGC GGT CTG CAC GAT TTG TCT GTG CTA CAC CTA        2064
Val Pro Ser Asp Asp Ser Gly Leu His Asp Leu Ser Val Leu His Leu
        675                 680                 685

GAC TCC TGT ACA GAT TAC AAT ATA TAT GGT AGA ACT GGT GTT GGT ATT        2112
Asp Ser Cys Thr Asp Tyr Asn Ile Tyr Gly Arg Thr Gly Val Gly Ile
    690                 695                 700

ATT AGA CGA ACT AAC AGT ACG CTA CTT AGT GGC TTA TAT TAC ACA TCA        2160
Ile Arg Arg Thr Asn Ser Thr Leu Leu Ser Gly Leu Tyr Tyr Thr Ser
705                 710                 715                 720

CTA TCA GGT GAT TTG TTA GGC TTT AAA AAT GTT AGT GAT GGT GTC ATT        2208
Leu Ser Gly Asp Leu Leu Gly Phe Lys Asn Val Ser Asp Gly Val Ile
                725                 730                 735

TAT TCT GTG ACG CCA TGT GAT GTA AGC GCA CAA GCG GC                     2246
Tyr Ser Val Thr Pro Cys Asp Val Ser Ala Gln Ala
            740                 745
```

(2) INFORMATION FOR SEQ ID NO:24:

(i) SEQUENCE CHARACTERISTICS:
(A) LENGTH: 748 amino acids
(B) TYPE: amino acid
(D) TOPOLOGY: linear (ii) MOLECULE TYPE: protein (xi) SEQUENCE DESCRIPTION: SEQ ID NO:24:

```
Met Ile Val Leu Val Thr Cys Leu Leu Leu Leu Cys Ser Tyr His Thr
  1               5                  10                  15

Val Leu Ser Thr Thr Asn Asn Glu Cys Ile Gln Val Asn Val Thr Gln
             20                  25                  30

Leu Ala Gly Asn Glu Asn Leu Ile Arg Asp Phe Leu Phe Ser Asn Phe
         35                  40                  45

Lys Glu Glu Gly Ser Val Val Val Gly Gly Tyr Tyr Pro Thr Glu Val
     50                  55                  60

Trp Tyr Asn Cys Ser Arg Thr Ala Arg Thr Thr Ala Phe Gln Tyr Phe
 65                  70                  75                  80

Asn Asn Ile His Ala Phe Tyr Phe Val Met Glu Ala Met Glu Asn Ser
                 85                  90                  95

Thr Gly Asn Ala Arg Gly Lys Pro Leu Leu Phe His Val His Gly Glu
            100                 105                 110

Pro Val Ser Val Ile Ile Tyr Ile Ser Ala Tyr Arg Asp Asp Val Gln
        115                 120                 125

Gln Arg Pro Leu Leu Glu His Gly Leu Val Cys Ile Thr Lys Asn Arg
    130                 135                 140

His Ile Asn Tyr Glu Gln Phe Thr Ser Asn Gln Trp Asn Ser Thr Cys
145                 150                 155                 160

Thr Gly Ala Asp Arg Lys Ile Pro Phe Ser Val Ile Pro Thr Asp Asn
                165                 170                 175

Gly Thr Lys Ile Tyr Gly Leu Glu Trp Asn Asp Asp Phe Val Thr Ala
            180                 185                 190

Tyr Ile Ser Gly Arg Ser Tyr His Leu Asn Ile Asn Thr Asn Trp Phe
        195                 200                 205

Asn Asn Val Thr Leu Leu Tyr Ser Arg Ser Ser Thr Ala Thr Trp Glu
    210                 215                 220

Tyr Ser Ala Ala Tyr Ala Tyr Gln Gly Val Ser Asn Phe Thr Tyr Tyr
225                 230                 235                 240

Lys Leu Asn Asn Thr Asn Gly Leu Lys Thr Tyr Glu Leu Cys Glu Asp
                245                 250                 255

Tyr Glu His Cys Thr Gly Tyr Ala Thr Asn Val Phe Ala Pro Thr Ser
            260                 265                 270

Gly Gly Tyr Ile Pro Asp Gly Phe Ser Phe Asn Asn Trp Phe Leu Leu
        275                 280                 285

Thr Asn Ser Ser Thr Phe Val Ser Gly Arg Phe Val Thr Asn Gln Pro
    290                 295                 300

Leu Leu Ile Asn Cys Leu Trp Pro Val Pro Ser Phe Gly Val Ala Ala
305                 310                 315                 320

Gln Glu Phe Cys Phe Glu Gly Ala Gln Phe Ser Gln Cys Asn Gly Val
                325                 330                 335

Ser Leu Asn Asn Thr Val Asp Val Ile Arg Phe Asn Leu Asn Phe Thr
            340                 345                 350
```

-continued

```
Ala Asp Val Gln Ser Gly Met Gly Ala Thr Val Phe Ser Leu Asn Thr
        355                 360                 365

Thr Gly Gly Val Ile Leu Glu Ile Ser Cys Tyr Ser Asp Thr Val Ser
    370                 375                 380

Glu Ser Ser Ser Tyr Ser Tyr Gly Glu Ile Pro Phe Gly Ile Thr Asp
385                 390                 395                 400

Gly Pro Arg Tyr Cys Tyr Val Leu Tyr Asn Gly Thr Ala Leu Lys Tyr
                405                 410                 415

Leu Gly Thr Leu Pro Pro Ser Val Lys Glu Ile Ala Ile Ser Lys Trp
            420                 425                 430

Gly His Phe Tyr Ile Asn Gly Tyr Asn Phe Phe Ser Thr Phe Pro Ile
        435                 440                 445

Gly Cys Ile Ser Phe Asn Leu Thr Thr Gly Val Ser Gly Ala Phe Trp
    450                 455                 460

Thr Ile Ala Tyr Thr Ser Tyr Thr Glu Ala Leu Val Gln Val Glu Asn
465                 470                 475                 480

Thr Ala Ile Lys Asn Val Thr Tyr Cys Asn Ser His Ile Asn Asn Ile
                485                 490                 495

Lys Cys Ser Gln Leu Thr Ala Asn Leu Asn Asn Gly Phe Tyr Pro Val
            500                 505                 510

Ala Ser Ser Glu Val Gly Phe Val Asn Lys Ser Val Val Leu Leu Pro
        515                 520                 525

Ser Phe Phe Thr Tyr Thr Ala Val Asn Ile Thr Ile Asp Leu Gly Met
    530                 535                 540

Lys Leu Ser Gly Tyr Gly Gln Pro Ile Ala Ser Thr Leu Ser Asn Ile
545                 550                 555                 560

Thr Leu Pro Met Gln Asp Asn Asn Thr Asp Val Tyr Cys Ile Arg Ser
                565                 570                 575

Asn Gln Phe Ser Val Tyr Val His Ser Thr Cys Lys Ser Ser Leu Trp
            580                 585                 590

Asp Asn Ile Phe Asn Gln Asp Cys Thr Asp Val Leu Glu Ala Thr Ala
        595                 600                 605

Val Ile Lys Thr Gly Thr Cys Pro Phe Ser Phe Asp Lys Leu Asn Asn
    610                 615                 620

Tyr Leu Thr Phe Asn Lys Phe Cys Leu Ser Leu Ser Pro Val Gly Ala
625                 630                 635                 640

Asn Cys Lys Phe Asp Val Ala Ala Arg Thr Arg Thr Asn Glu Gln Val
                645                 650                 655

Val Arg Ser Leu Tyr Val Ile Tyr Glu Glu Gly Asp Asn Ile Val Gly
            660                 665                 670

Val Pro Ser Asp Asp Ser Gly Leu His Asp Leu Ser Val Leu His Leu
        675                 680                 685

Asp Ser Cys Thr Asp Tyr Asn Ile Tyr Gly Arg Thr Gly Val Gly Ile
    690                 695                 700

Ile Arg Arg Thr Asn Ser Thr Leu Leu Ser Gly Leu Tyr Tyr Thr Ser
705                 710                 715                 720

Leu Ser Gly Asp Leu Leu Gly Phe Lys Asn Val Ser Asp Gly Val Ile
                725                 730                 735

Tyr Ser Val Thr Pro Cys Asp Val Ser Ala Gln Ala
            740                 745
```

(2) INFORMATION FOR SEQ ID NO:25:

(i) SEQUENCE CHARACTERISTICS:

-continued (A) LENGTH: 4365 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..4362

(xi) SEQUENCE DESCRIPTION: SEQ ID NO:25:

```
ATG ATT GTG CTC GTA ACT TGC CTC TTG TTG TTA TGT TCA TAC CAC ACA       48
Met Ile Val Leu Val Thr Cys Leu Leu Leu Leu Cys Ser Tyr His Thr
  1               5                  10                  15

GTT TTG AGT ACA ACA AAT AAT GAA TGC ATA CAA GTT AAC GTT ACA CAA       96
Val Leu Ser Thr Thr Asn Asn Glu Cys Ile Gln Val Asn Val Thr Gln
             20                  25                  30

TTG GCT GGC AAT GAA AAC CTT ATC AGA GAT TTT CTG TTT AGT AAC TTT      144
Leu Ala Gly Asn Glu Asn Leu Ile Arg Asp Phe Leu Phe Ser Asn Phe
         35                  40                  45

AAA GAA GAA GGA AGT GTA GTT GTT GGT GGT TAT TAC CCT ACA GAG GTG      192
Lys Glu Glu Gly Ser Val Val Val Gly Gly Tyr Tyr Pro Thr Glu Val
     50                  55                  60

TGG TAC AAC TGC TCT AGA ACA GCT CGA ACT ACT GCC TTT CAG TAT TTT      240
Trp Tyr Asn Cys Ser Arg Thr Ala Arg Thr Thr Ala Phe Gln Tyr Phe
 65                  70                  75                  80

AAT AAT ATA CAT GCC TTT TAT TTT GTT ATG GAA GCC ATG GAA AAT AGC      288
Asn Asn Ile His Ala Phe Tyr Phe Val Met Glu Ala Met Glu Asn Ser
                 85                  90                  95

ACT GGT AAT GCA CGT GGT AAA CCA TTA TTA TTT CAT GTG CAT GGT GAG      336
Thr Gly Asn Ala Arg Gly Lys Pro Leu Leu Phe His Val His Gly Glu
            100                 105                 110

CCT GTT AGT GTT ATT ATA TAT ATA TCG GCT TAT AGG GAT GAT GTG CAA      384
Pro Val Ser Val Ile Ile Tyr Ile Ser Ala Tyr Arg Asp Asp Val Gln
        115                 120                 125

CAA AGG CCC CTT TTA AAA CAT GGG TTA GTG TGC ATA ACT AAA AAT CGC      432
Gln Arg Pro Leu Leu Lys His Gly Leu Val Cys Ile Thr Lys Asn Arg
    130                 135                 140

CAT ATT AAC TAT GAA CAA TTC ACC TCC AAC CAG TGG AAT TCC ACA TGT      480
His Ile Asn Tyr Glu Gln Phe Thr Ser Asn Gln Trp Asn Ser Thr Cys
145                 150                 155                 160

ACG GGT GCT GAC AGA AAA ATT CCT TTC TCT GTC ATA CCC ACG GAC AAT      528
Thr Gly Ala Asp Arg Lys Ile Pro Phe Ser Val Ile Pro Thr Asp Asn
                165                 170                 175

GGA ACA AAA ATC TAT GGT CTT GAG TGG AAT GAT GAC TTT GTT ACA GCT      576
Gly Thr Lys Ile Tyr Gly Leu Glu Trp Asn Asp Asp Phe Val Thr Ala
            180                 185                 190

TAT ATT AGT GGT CGT TCT TAT CAC TTG AAC ATC AAT ACT AAT TGG TTT      624
Tyr Ile Ser Gly Arg Ser Tyr His Leu Asn Ile Asn Thr Asn Trp Phe
        195                 200                 205

AAC AAT GTC ACA CTT TTG TAT TCA CGC TCA AGC ACT GCT ACC TGG GAA      672
Asn Asn Val Thr Leu Leu Tyr Ser Arg Ser Ser Thr Ala Thr Trp Glu
    210                 215                 220

TAC AGT GCT GCA TAT GCT TAC CAA GGT GTT TCT AAC TTC ACT TAT TAC      720
Tyr Ser Ala Ala Tyr Ala Tyr Gln Gly Val Ser Asn Phe Thr Tyr Tyr
225                 230                 235                 240

AAG TTA AAT AAC ACC AAT GGT CTA AAA ACC TAT GAA TTA TGT GAA GAT      768
Lys Leu Asn Asn Thr Asn Gly Leu Lys Thr Tyr Glu Leu Cys Glu Asp
                245                 250                 255

TAT GAA CAT TGC ACT GGC TAT GCT ACC AAT GTA TTT GCT CCG ACA TCA      816
Tyr Glu His Cys Thr Gly Tyr Ala Thr Asn Val Phe Ala Pro Thr Ser
```

-continued

```
            260                 265                 270

GGT GGT TAC ATA CCT GAT GGA TTT AGT TTT AAT AAT TGG TTC TTG CTT      864
Gly Gly Tyr Ile Pro Asp Gly Phe Ser Phe Asn Asn Trp Phe Leu Leu
        275                 280                 285

ACA AAT AGT TCC ACT TTT GTT AGT GGC AGG TTT GTA ACA AAT CAA CCA      912
Thr Asn Ser Ser Thr Phe Val Ser Gly Arg Phe Val Thr Asn Gln Pro
    290                 295                 300

TTA TTG ATT AAT TGC TTG TGG CCA GTG CCC AGT TTT GGT GTA GTA GCA      960
Leu Leu Ile Asn Cys Leu Trp Pro Val Pro Ser Phe Gly Val Val Ala
305                 310                 315                 320

CAA GAA TTT TGT TTT GAA GGT GCA CAG TTT AGC CAA TGT AAT GGT GTG     1008
Gln Glu Phe Cys Phe Glu Gly Ala Gln Phe Ser Gln Cys Asn Gly Val
                325                 330                 335

TCT TTA AAT AAC ACA GTG GAT GTT ATT AGA TTC AAC CTT AAT TTC ACT     1056
Ser Leu Asn Asn Thr Val Asp Val Ile Arg Phe Asn Leu Asn Phe Thr
            340                 345                 350

GCA GAT GTA CAA TCT GGT ATG GGT GCT ACA GTA TTT TCA CTG AAT ACA     1104
Ala Asp Val Gln Ser Gly Met Gly Ala Thr Val Phe Ser Leu Asn Thr
        355                 360                 365

ACA GGT GGT GTC ATT CTT GAA ATT TCA TGT TAT AGT GAC ACA GTG AGT     1152
Thr Gly Gly Val Ile Leu Glu Ile Ser Cys Tyr Ser Asp Thr Val Ser
    370                 375                 380

GAG TCT AGT TCT TAC AGT TAT GGT GAA ATC CCG TTC GGC ATA ACT GAC     1200
Glu Ser Ser Ser Tyr Ser Tyr Gly Glu Ile Pro Phe Gly Ile Thr Asp
385                 390                 395                 400

GGA CCA CGA TAC TGT TAT GTA CTT TAC AAT GGC ACA GCT CTT AAA TAT     1248
Gly Pro Arg Tyr Cys Tyr Val Leu Tyr Asn Gly Thr Ala Leu Lys Tyr
                405                 410                 415

TTA GGA ACA TTA CCA CCC AGT GTA AAG GAA ATT GCT ATT AGT AAG TGG     1296
Leu Gly Thr Leu Pro Pro Ser Val Lys Glu Ile Ala Ile Ser Lys Trp
            420                 425                 430

GGC CAT TTT TAT ATT AAT GGT TAC AAT TTC TTT AGC ACA TTT CCT ATT     1344
Gly His Phe Tyr Ile Asn Gly Tyr Asn Phe Phe Ser Thr Phe Pro Ile
        435                 440                 445

GAT TGT ATA TCT TTT AAT TTA ACC ACT GGT GTT AGT GGA GCT TTT TGG     1392
Asp Cys Ile Ser Phe Asn Leu Thr Thr Gly Val Ser Gly Ala Phe Trp
    450                 455                 460

ACA ATT GCT TAC ACA TCG TAT ACT GAA GCA TTA GTA CAA GTT GAA AAC     1440
Thr Ile Ala Tyr Thr Ser Tyr Thr Glu Ala Leu Val Gln Val Glu Asn
465                 470                 475                 480

ACA GCT ATT AAA AAT GTG ACG TAT TGT AAC AGT CAC ATT AAT AAC ATT     1488
Thr Ala Ile Lys Asn Val Thr Tyr Cys Asn Ser His Ile Asn Asn Ile
                485                 490                 495

AAA TGT TCT CAA CTT ACT GCT AAT TTG AAT AAT GGA TTT TAT CCT GTT     1536
Lys Cys Ser Gln Leu Thr Ala Asn Leu Asn Asn Gly Phe Tyr Pro Val
            500                 505                 510

GCT TCA AGT GAA GTA GGT TTC GTT AAT AAG AGT GTT GTG TTA TTA CCT     1584
Ala Ser Ser Glu Val Gly Phe Val Asn Lys Ser Val Val Leu Leu Pro
        515                 520                 525

AGC TTT TTC ACA TAC ACC GCT GTC AAT ATA ACC ATT GAT CTT GGT ATG     1632
Ser Phe Phe Thr Tyr Thr Ala Val Asn Ile Thr Ile Asp Leu Gly Met
    530                 535                 540

AAG CTT AGT GGT TAT GGT CAA CCC ATA GCC TCG ACA CTA AGT AAC ATC     1680
Lys Leu Ser Gly Tyr Gly Gln Pro Ile Ala Ser Thr Leu Ser Asn Ile
545                 550                 555                 560

ACA CTA CCA ATG CAG GAT AAC AAT ACT GAT GTG TAC TGT ATT CGT TCT     1728
Thr Leu Pro Met Gln Asp Asn Asn Thr Asp Val Tyr Cys Ile Arg Ser
                565                 570                 575

AAC CAA TTC TCA GTT TAT GTT CAT TCC ACT TGC AAA AGT TCT TTA TGG     1776
```

-continued

```
Asn Gln Phe Ser Val Tyr Val His Ser Thr Cys Lys Ser Ser Leu Trp
            580                 585                 590

GAC AAT ATT TTT AAT CAA GAC TGC ACG GAT GTT TTA GAG GCT ACA GCT      1824
Asp Asn Ile Phe Asn Gln Asp Cys Thr Asp Val Leu Glu Ala Thr Ala
        595                 600                 605

GTT ATA AAA ACT GGT ACT TGT CCT TTC TCA TTT GAT AAA TTG AAC AAT      1872
Val Ile Lys Thr Gly Thr Cys Pro Phe Ser Phe Asp Lys Leu Asn Asn
    610                 615                 620

TAC TTG ACT TTT AAC ACG TTC TGT TTG TCG TTG AGT CCT GTT GGT GCT      1920
Tyr Leu Thr Phe Asn Thr Phe Cys Leu Ser Leu Ser Pro Val Gly Ala
625                 630                 635                 640

AAT TGC AAG TTT GAT GTT GCT GCA CGT ACA AGA ACC AAT GAG CAG GTT      1968
Asn Cys Lys Phe Asp Val Ala Ala Arg Thr Arg Thr Asn Glu Gln Val
                645                 650                 655

GTT AGA AGT CTA TAT ATA ATA TAT GAA GAA GGA GAC AAC ATA GTG GGT      2016
Val Arg Ser Leu Tyr Ile Ile Tyr Glu Glu Gly Asp Asn Ile Val Gly
            660                 665                 670

GTA CCG TCT GAT GAT AGC GGT CTG CAC GAT TTG TCT GTG CTA CAC CTA      2064
Val Pro Ser Asp Asp Ser Gly Leu His Asp Leu Ser Val Leu His Leu
        675                 680                 685

GAC TCC TGT ACA GAT TAC AAT ATA TAT GGT AGA ACT GGT GTT GGT ATT      2112
Asp Ser Cys Thr Asp Tyr Asn Ile Tyr Gly Arg Thr Gly Val Gly Ile
    690                 695                 700

ATT AGA CGA ACT AAC AGT ACG CTA CTT AGT GGC TTA TAT TAC ACA TCA      2160
Ile Arg Arg Thr Asn Ser Thr Leu Leu Ser Gly Leu Tyr Tyr Thr Ser
705                 710                 715                 720

CTA TCA GGT GAT TTG TTA GGC TTT AAA AAT GTT AGT GAT GGT GTC ATT      2208
Leu Ser Gly Asp Leu Leu Gly Phe Lys Asn Val Ser Asp Gly Val Ile
                725                 730                 735

TAT TCT GTG ACG CCA TGT GAT GTA AGC GCA CAA GCG GCT GTT ATT GAT      2256
Tyr Ser Val Thr Pro Cys Asp Val Ser Ala Gln Ala Ala Val Ile Asp
            740                 745                 750

GGT GCC ATA GTT GGA GCT ATG ACT TCC ATT AAC AGT GAA CTG TTA GGT      2304
Gly Ala Ile Val Gly Ala Met Thr Ser Ile Asn Ser Glu Leu Leu Gly
        755                 760                 765

CTA ATA CAT TGG ACA ACG ACA CCT AAT TTT TAT TAC TAC TCT ATA TAT      2352
Leu Ile His Trp Thr Thr Thr Pro Asn Phe Tyr Tyr Tyr Ser Ile Tyr
    770                 775                 780

AAT TAC ACA AGT GAG AGG ACT CGT GGC ACT GCA ATT GAC AGT AAC GAT      2400
Asn Tyr Thr Ser Glu Arg Thr Arg Gly Thr Ala Ile Asp Ser Asn Asp
785                 790                 795                 800

GTT GAT TGT GAA CCT GTC ATA ACC TAT TCT AAT ATA GGT GTT TGT AAA      2448
Val Asp Cys Glu Pro Val Ile Thr Tyr Ser Asn Ile Gly Val Cys Lys
                805                 810                 815

AAT GGT GCT TTG GTT TTT ATT AAC GTC ACA CAT TCT GAC GGA GAC GTG      2496
Asn Gly Ala Leu Val Phe Ile Asn Val Thr His Ser Asp Gly Asp Val
            820                 825                 830

CAA CCA ATT AGC ACT GGT AAT GTC ACG ATA CCT ACA AAT TTT ACC ATA      2544
Gln Pro Ile Ser Thr Gly Asn Val Thr Ile Pro Thr Asn Phe Thr Ile
        835                 840                 845

TCT GTG CAA GTT GAA TAC ATG CAG GTT TAC ACT ACA CCA GTA TCA ATA      2592
Ser Val Gln Val Glu Tyr Met Gln Val Tyr Thr Thr Pro Val Ser Ile
    850                 855                 860

GAT TGT GCA AGA TAC GTT TGT AAT GGT AAC CCT AGA TGT AAC AAA TTG      2640
Asp Cys Ala Arg Tyr Val Cys Asn Gly Asn Pro Arg Cys Asn Lys Leu
865                 870                 875                 880

TTA ACA CAA TAT GTG TCT GCA TGT CAA ACT ATT GAA CAA GCA CTT GCA      2688
Leu Thr Gln Tyr Val Ser Ala Cys Gln Thr Ile Glu Gln Ala Leu Ala
                885                 890                 895
```

-continued

```
ATG GGT GCC AGA CTT GAA AAC ATG GAG GTT GAT TCC ATG TTG TTT GTC      2736
Met Gly Ala Arg Leu Glu Asn Met Glu Val Asp Ser Met Leu Phe Val
            900                 905                 910

TCG GAA AAT GCC CTT AAA TTG GCA TCT GTT GAG GCG TTC AAT AGT ACA      2784
Ser Glu Asn Ala Leu Lys Leu Ala Ser Val Glu Ala Phe Asn Ser Thr
        915                 920                 925

GAA AAT TTA GAT CCT ATT TAC AAA GAA TGG CCT AGC ATA GGT GGT TCT      2832
Glu Asn Leu Asp Pro Ile Tyr Lys Glu Trp Pro Ser Ile Gly Gly Ser
    930                 935                 940

TGG CTA GGA GGT CTA AAA GAT ATA CTA CCG TCC CAT AAT AGC AAA CGT      2880
Trp Leu Gly Gly Leu Lys Asp Ile Leu Pro Ser His Asn Ser Lys Arg
945                 950                 955                 960

AAG TAT GGT TCT GCT ATA GAA GAT TTG CTT TTT GAT AAA GTT GTA ACA      2928
Lys Tyr Gly Ser Ala Ile Glu Asp Leu Leu Phe Asp Lys Val Val Thr
                965                 970                 975

TCT GGT TTA GGT ACA GTT GAT GAA GAT TAT AAA CGT TGT ACT GGT GGT      2976
Ser Gly Leu Gly Thr Val Asp Glu Asp Tyr Lys Arg Cys Thr Gly Gly
            980                 985                 990

TAC GAC ATA GCA GAC TTG GTG TGT GCT CAA TAT TAC AAT GGC ATC ATG      3024
Tyr Asp Ile Ala Asp Leu Val Cys Ala Gln Tyr Tyr Asn Gly Ile Met
        995                 1000                1005

GTT CTA CCA GGT GTA GCT AAT GCT GAC AAG ATG ACT ATG TAC ACA GCA      3072
Val Leu Pro Gly Val Ala Asn Ala Asp Lys Met Thr Met Tyr Thr Ala
    1010                1015                1020

TCA CTT GCA GGT GGT ATA ACA TTA GGT GCA CTT GGT GGT GGC GCC GTG      3120
Ser Leu Ala Gly Gly Ile Thr Leu Gly Ala Leu Gly Gly Gly Ala Val
1025                1030                1035                1040

GCT ATA CCT TTT GCA GTA GCA GTA CAG GCT AGA CTT AAT TAT GTT GCT      3168
Ala Ile Pro Phe Ala Val Ala Val Gln Ala Arg Leu Asn Tyr Val Ala
                1045                1050                1055

CTA CAA ACT GAT GTA TTG AAT AAA AAC CAA CAG ATC CTG GCT AAT GCT      3216
Leu Gln Thr Asp Val Leu Asn Lys Asn Gln Gln Ile Leu Ala Asn Ala
            1060                1065                1070

TTC AAT CAA GCT ATT GGT AAC ATT ACA CAG GCT TTT GGT AAG GTT AAT      3264
Phe Asn Gln Ala Ile Gly Asn Ile Thr Gln Ala Phe Gly Lys Val Asn
        1075                1080                1085

GAT GCT ATA CAT CAA ACA TCA CAA GGT CTT GCC ACT GTT GCT AAA GCG      3312
Asp Ala Ile His Gln Thr Ser Gln Gly Leu Ala Thr Val Ala Lys Ala
    1090                1095                1100

TTG GCA AAA GTG CAA GAT GTT GTC AAC ACA CAA GGG CAA GCT TTA AGT      3360
Leu Ala Lys Val Gln Asp Val Val Asn Thr Gln Gly Gln Ala Leu Ser
1105                1110                1115                1120

CAC CTT ACA GTA CAA TTG CAA AAT AAT TTT CAA GCC ATT AGT AGT TCT      3408
His Leu Thr Val Gln Leu Gln Asn Asn Phe Gln Ala Ile Ser Ser Ser
                1125                1130                1135

ATT AGT GAT ATT TAT AAC AGG CTT GAC GAA CTG AGT GCT GAT GCA CAA      3456
Ile Ser Asp Ile Tyr Asn Arg Leu Asp Glu Leu Ser Ala Asp Ala Gln
            1140                1145                1150

GTT GAT AGG CTG ATT ACA GGT AGA CTT ACA GCA CTT AAT GCA TTT GTG      3504
Val Asp Arg Leu Ile Thr Gly Arg Leu Thr Ala Leu Asn Ala Phe Val
        1155                1160                1165

TCT CAG ACT CTA ACC AGA CAA GCA GAG GTT AGG GCT AGT AGA CAA CTT      3552
Ser Gln Thr Leu Thr Arg Gln Ala Glu Val Arg Ala Ser Arg Gln Leu
    1170                1175                1180

GCC AAA GAC AAG GTT AAT GAA TGT GTT AGG TCT CAG TCT CAG AGA TTC      3600
Ala Lys Asp Lys Val Asn Glu Cys Val Arg Ser Gln Ser Gln Arg Phe
1185                1190                1195                1200

GGA TTC TGT GGT AAT GGT ACA CAT TTG TTT TCA CTA GCA AAT GCA GCA      3648
Gly Phe Cys Gly Asn Gly Thr His Leu Phe Ser Leu Ala Asn Ala Ala
                1205                1210                1215
```

-continued

```
CCA AAT GGC ATG ATT TTC TTT CAT ACA GTA CTA TTA CCA ACA GCT TAT     3696
Pro Asn Gly Met Ile Phe Phe His Thr Val Leu Leu Pro Thr Ala Tyr
            1220                1225                1230

GAA ACT GTA ACA GCT TGG TCA GGT ATT TGT GCT TCA GAT GGC GAT CGC     3744
Glu Thr Val Thr Ala Trp Ser Gly Ile Cys Ala Ser Asp Gly Asp Arg
        1235                1240                1245

ACT TTC GGA CTT GTC GTT AAA GAT GTG CAG TTG ACG TTG TTT CGT AAT     3792
Thr Phe Gly Leu Val Val Lys Asp Val Gln Leu Thr Leu Phe Arg Asn
    1250                1255                1260

CTA GAT GAC AAG TTC TAT TTG ACC CCC AGA ACT ATG TAT CAG CCT AGA     3840
Leu Asp Asp Lys Phe Tyr Leu Thr Pro Arg Thr Met Tyr Gln Pro Arg
1265                1270                1275                1280

GTT GCA ACT AGT TCT GAT TTT GTT CAA ATT GAA GGG TGT GAT GTG TTG     3888
Val Ala Thr Ser Ser Asp Phe Val Gln Ile Glu Gly Cys Asp Val Leu
                1285                1290                1295

TTT GTC AAC GCG ACT GTA ATT GAT TTG CCT AGT ATT ATA CCT GAC TAT     3936
Phe Val Asn Ala Thr Val Ile Asp Leu Pro Ser Ile Ile Pro Asp Tyr
            1300                1305                1310

ATT GAC ATT AAT CAA ACT GTT CAA GAC ATA TTA GAA AAT TAC AGA CCA     3984
Ile Asp Ile Asn Gln Thr Val Gln Asp Ile Leu Glu Asn Tyr Arg Pro
        1315                1320                1325

AAC TGG ACT GTA CCT GAA TTT ACA CTT GAT ATT TTC AAC ACA ACC TAT     4032
Asn Trp Thr Val Pro Glu Phe Thr Leu Asp Ile Phe Asn Thr Thr Tyr
    1330                1335                1340

TTA AAT CTG ACT GGT GAA ATT GAT GAC TTA GAG TTT AGG TCG GAA AAG     4080
Leu Asn Leu Thr Gly Glu Ile Asp Asp Leu Glu Phe Arg Ser Glu Lys
1345                1350                1355                1360

CTA CAT AAC ACT ACA GTA GAA CTT GCC ATT CTC ATT GAT AAC ATT AAT     4128
Leu His Asn Thr Thr Val Glu Leu Ala Ile Leu Ile Asp Asn Ile Asn
                1365                1370                1375

AAT ACA TTA GTC AAT CTT GAA TGG CTC AAT AGA ATT GAA ACT TAT GTA     4176
Asn Thr Leu Val Asn Leu Glu Trp Leu Asn Arg Ile Glu Thr Tyr Val
            1380                1385                1390

AAA TGG CCT TGG TAT GTG TGG CTA CTG ATA GGT TTA GTA GTA GTA TTT     4224
Lys Trp Pro Trp Tyr Val Trp Leu Leu Ile Gly Leu Val Val Val Phe
        1395                1400                1405

TGC ATA CCA TTA CTG CTA TTT TGC TGT TTT AGC ACA GGT TGT TGT GGA     4272
Cys Ile Pro Leu Leu Leu Phe Cys Cys Phe Ser Thr Gly Cys Cys Gly
    1410                1415                1420

TGC ATA GGT TGT TTA GGA AGT TGT TGT CAC TCT ATA TGT AGT AGA AGA     4320
Cys Ile Gly Cys Leu Gly Ser Cys Cys His Ser Ile Cys Ser Arg Arg
1425                1430                1435                1440

CAA TTT GAA AAT TAT GAA CCA ATT GAA AAA GTG CAT GTC CAC             4362
Gln Phe Glu Asn Tyr Glu Pro Ile Glu Lys Val His Val His
                1445                1450

TAA                                                                 4365
```

(2) INFORMATION FOR SEQ ID NO:26:

(i) SEQUENCE CHARACTERISTICS:
(A) LENGTH: 1454 amino acids
(B) TYPE: amino acid
(D) TOPOLOGY: linear (ii) MOLECULE TYPE: protein (xi) SEQUENCE DESCRIPTION: SEQ ID NO:26:

```
Met Ile Val Leu Val Thr Cys Leu Leu Leu Leu Cys Ser Tyr His Thr
  1               5                  10                  15

Val Leu Ser Thr Thr Asn Asn Glu Cys Ile Gln Val Asn Val Thr Gln
```

-continued

```
            20                  25                  30

Leu Ala Gly Asn Glu Asn Leu Ile Arg Asp Phe Leu Phe Ser Asn Phe
        35                  40                  45

Lys Glu Glu Gly Ser Val Val Val Gly Gly Tyr Tyr Pro Thr Glu Val
    50                  55                  60

Trp Tyr Asn Cys Ser Arg Thr Ala Arg Thr Thr Ala Phe Gln Tyr Phe
65                  70                  75                  80

Asn Asn Ile His Ala Phe Tyr Phe Val Met Glu Ala Met Glu Asn Ser
                85                  90                  95

Thr Gly Asn Ala Arg Gly Lys Pro Leu Leu Phe His Val His Gly Glu
            100                 105                 110

Pro Val Ser Val Ile Ile Tyr Ile Ser Ala Tyr Arg Asp Asp Val Gln
        115                 120                 125

Gln Arg Pro Leu Leu Lys His Gly Leu Val Cys Ile Thr Lys Asn Arg
    130                 135                 140

His Ile Asn Tyr Glu Gln Phe Thr Ser Asn Gln Trp Asn Ser Thr Cys
145                 150                 155                 160

Thr Gly Ala Asp Arg Lys Ile Pro Phe Ser Val Ile Pro Thr Asp Asn
                165                 170                 175

Gly Thr Lys Ile Tyr Gly Leu Glu Trp Asn Asp Asp Phe Val Thr Ala
            180                 185                 190

Tyr Ile Ser Gly Arg Ser Tyr His Leu Asn Ile Asn Thr Asn Trp Phe
        195                 200                 205

Asn Asn Val Thr Leu Leu Tyr Ser Arg Ser Ser Thr Ala Thr Trp Glu
    210                 215                 220

Tyr Ser Ala Ala Tyr Ala Tyr Gln Gly Val Ser Asn Phe Thr Tyr Tyr
225                 230                 235                 240

Lys Leu Asn Asn Thr Asn Gly Leu Lys Thr Tyr Glu Leu Cys Glu Asp
                245                 250                 255

Tyr Glu His Cys Thr Gly Tyr Ala Thr Asn Val Phe Ala Pro Thr Ser
            260                 265                 270

Gly Gly Tyr Ile Pro Asp Gly Phe Ser Phe Asn Asn Trp Phe Leu Leu
        275                 280                 285

Thr Asn Ser Ser Thr Phe Val Ser Gly Arg Phe Val Thr Asn Gln Pro
    290                 295                 300

Leu Leu Ile Asn Cys Leu Trp Pro Val Pro Ser Phe Gly Val Val Ala
305                 310                 315                 320

Gln Glu Phe Cys Phe Glu Gly Ala Gln Phe Ser Gln Cys Asn Gly Val
                325                 330                 335

Ser Leu Asn Asn Thr Val Asp Val Ile Arg Phe Asn Leu Asn Phe Thr
            340                 345                 350

Ala Asp Val Gln Ser Gly Met Gly Ala Thr Val Phe Ser Leu Asn Thr
        355                 360                 365

Thr Gly Gly Val Ile Leu Glu Ile Ser Cys Tyr Ser Asp Thr Val Ser
    370                 375                 380

Glu Ser Ser Ser Tyr Ser Tyr Gly Glu Ile Pro Phe Gly Ile Thr Asp
385                 390                 395                 400

Gly Pro Arg Tyr Cys Tyr Val Leu Tyr Asn Gly Thr Ala Leu Lys Tyr
                405                 410                 415

Leu Gly Thr Leu Pro Pro Ser Val Lys Glu Ile Ala Ile Ser Lys Trp
            420                 425                 430

Gly His Phe Tyr Ile Asn Gly Tyr Asn Phe Phe Ser Thr Phe Pro Ile
        435                 440                 445
```

-continued

```
Asp Cys Ile Ser Phe Asn Leu Thr Thr Gly Val Ser Gly Ala Phe Trp
    450                 455                 460

Thr Ile Ala Tyr Thr Ser Tyr Thr Glu Ala Leu Val Gln Val Glu Asn
465                 470                 475                 480

Thr Ala Ile Lys Asn Val Thr Tyr Cys Asn Ser His Ile Asn Asn Ile
                485                 490                 495

Lys Cys Ser Gln Leu Thr Ala Asn Leu Asn Asn Gly Phe Tyr Pro Val
            500                 505                 510

Ala Ser Ser Glu Val Gly Phe Val Asn Lys Ser Val Val Leu Leu Pro
        515                 520                 525

Ser Phe Phe Thr Tyr Thr Ala Val Asn Ile Thr Ile Asp Leu Gly Met
    530                 535                 540

Lys Leu Ser Gly Tyr Gly Gln Pro Ile Ala Ser Thr Leu Ser Asn Ile
545                 550                 555                 560

Thr Leu Pro Met Gln Asp Asn Asn Thr Asp Val Tyr Cys Ile Arg Ser
                565                 570                 575

Asn Gln Phe Ser Val Tyr Val His Ser Thr Cys Lys Ser Ser Leu Trp
            580                 585                 590

Asp Asn Ile Phe Asn Gln Asp Cys Thr Asp Val Leu Glu Ala Thr Ala
        595                 600                 605

Val Ile Lys Thr Gly Thr Cys Pro Phe Ser Phe Asp Lys Leu Asn Asn
    610                 615                 620

Tyr Leu Thr Phe Asn Thr Phe Cys Leu Ser Leu Ser Pro Val Gly Ala
625                 630                 635                 640

Asn Cys Lys Phe Asp Val Ala Ala Arg Thr Arg Thr Asn Glu Gln Val
                645                 650                 655

Val Arg Ser Leu Tyr Ile Ile Tyr Glu Glu Gly Asp Asn Ile Val Gly
            660                 665                 670

Val Pro Ser Asp Asp Ser Gly Leu His Asp Leu Ser Val Leu His Leu
        675                 680                 685

Asp Ser Cys Thr Asp Tyr Asn Ile Tyr Gly Arg Thr Gly Val Gly Ile
    690                 695                 700

Ile Arg Arg Thr Asn Ser Thr Leu Leu Ser Gly Leu Tyr Tyr Thr Ser
705                 710                 715                 720

Leu Ser Gly Asp Leu Leu Gly Phe Lys Asn Val Ser Asp Gly Val Ile
                725                 730                 735

Tyr Ser Val Thr Pro Cys Asp Val Ser Ala Gln Ala Ala Val Ile Asp
            740                 745                 750

Gly Ala Ile Val Gly Ala Met Thr Ser Ile Asn Ser Glu Leu Leu Gly
        755                 760                 765

Leu Ile His Trp Thr Thr Thr Pro Asn Phe Tyr Tyr Tyr Ser Ile Tyr
    770                 775                 780

Asn Tyr Thr Ser Glu Arg Thr Arg Gly Thr Ala Ile Asp Ser Asn Asp
785                 790                 795                 800

Val Asp Cys Glu Pro Val Ile Thr Tyr Ser Asn Ile Gly Val Cys Lys
                805                 810                 815

Asn Gly Ala Leu Val Phe Ile Asn Val Thr His Ser Asp Gly Asp Val
            820                 825                 830

Gln Pro Ile Ser Thr Gly Asn Val Thr Ile Pro Thr Asn Phe Thr Ile
        835                 840                 845

Ser Val Gln Val Glu Tyr Met Gln Val Tyr Thr Thr Pro Val Ser Ile
    850                 855                 860
```

-continued

```
Asp Cys Ala Arg Tyr Val Cys Asn Gly Asn Pro Arg Cys Asn Lys Leu
865                 870                 875                 880

Leu Thr Gln Tyr Val Ser Ala Cys Gln Thr Ile Glu Gln Ala Leu Ala
                885                 890                 895

Met Gly Ala Arg Leu Glu Asn Met Glu Val Asp Ser Met Leu Phe Val
            900                 905                 910

Ser Glu Asn Ala Leu Lys Leu Ala Ser Val Glu Ala Phe Asn Ser Thr
        915                 920                 925

Glu Asn Leu Asp Pro Ile Tyr Lys Glu Trp Pro Ser Ile Gly Gly Ser
    930                 935                 940

Trp Leu Gly Gly Leu Lys Asp Ile Leu Pro Ser His Asn Ser Lys Arg
945                 950                 955                 960

Lys Tyr Gly Ser Ala Ile Glu Asp Leu Leu Phe Asp Lys Val Val Thr
                965                 970                 975

Ser Gly Leu Gly Thr Val Asp Glu Asp Tyr Lys Arg Cys Thr Gly Gly
            980                 985                 990

Tyr Asp Ile Ala Asp Leu Val Cys Ala Gln Tyr Tyr Asn Gly Ile Met
        995                 1000                1005

Val Leu Pro Gly Val Ala Asn Ala Asp Lys Met Thr Met Tyr Thr Ala
    1010                1015                1020

Ser Leu Ala Gly Gly Ile Thr Leu Gly Ala Leu Gly Gly Gly Ala Val
1025                1030                1035                1040

Ala Ile Pro Phe Ala Val Ala Val Gln Ala Arg Leu Asn Tyr Val Ala
                1045                1050                1055

Leu Gln Thr Asp Val Leu Asn Lys Asn Gln Gln Ile Leu Ala Asn Ala
            1060                1065                1070

Phe Asn Gln Ala Ile Gly Asn Ile Thr Gln Ala Phe Gly Lys Val Asn
        1075                1080                1085

Asp Ala Ile His Gln Thr Ser Gln Gly Leu Ala Thr Val Ala Lys Ala
    1090                1095                1100

Leu Ala Lys Val Gln Asp Val Val Asn Thr Gln Gly Gln Ala Leu Ser
1105                1110                1115                1120

His Leu Thr Val Gln Leu Gln Asn Asn Phe Gln Ala Ile Ser Ser Ser
                1125                1130                1135

Ile Ser Asp Ile Tyr Asn Arg Leu Asp Glu Leu Ser Ala Asp Ala Gln
            1140                1145                1150

Val Asp Arg Leu Ile Thr Gly Arg Leu Thr Ala Leu Asn Ala Phe Val
        1155                1160                1165

Ser Gln Thr Leu Thr Arg Gln Ala Glu Val Arg Ala Ser Arg Gln Leu
    1170                1175                1180

Ala Lys Asp Lys Val Asn Glu Cys Val Arg Ser Gln Ser Gln Arg Phe
1185                1190                1195                1200

Gly Phe Cys Gly Asn Gly Thr His Leu Phe Ser Leu Ala Asn Ala Ala
                1205                1210                1215

Pro Asn Gly Met Ile Phe Phe His Thr Val Leu Leu Pro Thr Ala Tyr
            1220                1225                1230

Glu Thr Val Thr Ala Trp Ser Gly Ile Cys Ala Ser Asp Gly Asp Arg
        1235                1240                1245

Thr Phe Gly Leu Val Val Lys Asp Val Gln Leu Thr Leu Phe Arg Asn
    1250                1255                1260

Leu Asp Asp Lys Phe Tyr Leu Thr Pro Arg Thr Met Tyr Gln Pro Arg
1265                1270                1275                1280

Val Ala Thr Ser Ser Asp Phe Val Gln Ile Glu Gly Cys Asp Val Leu
```

-continued

```
            1285                1290                1295

Phe Val Asn Ala Thr Val Ile Asp Leu Pro Ser Ile Ile Pro Asp Tyr
        1300                1305                1310

Ile Asp Ile Asn Gln Thr Val Gln Asp Ile Leu Glu Asn Tyr Arg Pro
    1315                1320                1325

Asn Trp Thr Val Pro Glu Phe Thr Leu Asp Ile Phe Asn Thr Thr Tyr
    1330                1335                1340

Leu Asn Leu Thr Gly Glu Ile Asp Asp Leu Glu Phe Arg Ser Glu Lys
1345                1350                1355                1360

Leu His Asn Thr Thr Val Glu Leu Ala Ile Leu Ile Asp Asn Ile Asn
            1365                1370                1375

Asn Thr Leu Val Asn Leu Glu Trp Leu Asn Arg Ile Glu Thr Tyr Val
        1380                1385                1390

Lys Trp Pro Trp Tyr Val Trp Leu Leu Ile Gly Leu Val Val Val Phe
    1395                1400                1405

Cys Ile Pro Leu Leu Leu Phe Cys Cys Phe Ser Thr Gly Cys Cys Gly
    1410                1415                1420

Cys Ile Gly Cys Leu Gly Ser Cys Cys His Ser Ile Cys Ser Arg Arg
1425                1430                1435                1440

Gln Phe Glu Asn Tyr Glu Pro Ile Glu Lys Val His Val His
            1445                1450
```

(2) INFORMATION FOR SEQ ID NO:27:

(i) SEQUENCE CHARACTERISTICS:
(A) LENGTH: 2246 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..2244

(xi) SEQUENCE DESCRIPTION: SEQ ID NO:27:

```
ATG ATT GTG CTC GTA ACT TGC CTC TTG TTG TTA TGT TCA TAC CAC ACA       48
Met Ile Val Leu Val Thr Cys Leu Leu Leu Leu Cys Ser Tyr His Thr
  1               5                  10                  15

GTT TTG AGT ACA ACA AAT AAT GAA TGC ATA CAA GTT AAC GTA ACA CAA       96
Val Leu Ser Thr Thr Asn Asn Glu Cys Ile Gln Val Asn Val Thr Gln
             20                  25                  30

TTG GCT GGC AAT GAA AAC CTT ATC AGA GAT TTT CTG TTT AGT AAC TTT      144
Leu Ala Gly Asn Glu Asn Leu Ile Arg Asp Phe Leu Phe Ser Asn Phe
         35                  40                  45

AAA GAA GAA GGA AGT GTA GTT GTT GGT GGT TAT TAC CCT ACA GAG GTG      192
Lys Glu Glu Gly Ser Val Val Val Gly Gly Tyr Tyr Pro Thr Glu Val
     50                  55                  60

TGG TAC AAC TGC TCT AGA ACA GCT CGA ACT ACT GCC TTT CAG TAT TTT      240
Trp Tyr Asn Cys Ser Arg Thr Ala Arg Thr Thr Ala Phe Gln Tyr Phe
 65                  70                  75                  80

AAT AAT ATA CAT GCC TTT TAT TTT GTT ATG GAA GCC ATG GAA AAT AGC      288
Asn Asn Ile His Ala Phe Tyr Phe Val Met Glu Ala Met Glu Asn Ser
                 85                  90                  95

ACT GGT AAT GCA CGT GGT AAA CCA TTA TTA TTT CAT GTG CAT GGT GAG      336
Thr Gly Asn Ala Arg Gly Lys Pro Leu Leu Phe His Val His Gly Glu
            100                 105                 110

CCT GTT AGT GTT ATT ATA TAT ATA TCG GCT TAT AGG GAT GAT GTG CAA      384
Pro Val Ser Val Ile Ile Tyr Ile Ser Ala Tyr Arg Asp Asp Val Gln
```

-continued

```
        115                 120                 125

CAA AGG CCC CTT TTA AAA CAT GGG TTA GTG TGC ATA ACT AAA AAT CGC      432
Gln Arg Pro Leu Leu Lys His Gly Leu Val Cys Ile Thr Lys Asn Arg
    130                 135                 140

CAT ATT AAC TAT GAA CAA TTC ACC TCC AAC CAG TGG AAT TCC ACA TGT      480
His Ile Asn Tyr Glu Gln Phe Thr Ser Asn Gln Trp Asn Ser Thr Cys
145                 150                 155                 160

ACG GGT GCT GAC AGA AAA ATT CCT TTC TCT GTC ATA CCC ACG GAC AAT      528
Thr Gly Ala Asp Arg Lys Ile Pro Phe Ser Val Ile Pro Thr Asp Asn
                165                 170                 175

GGA ACA AAA ATC TAT GGT CTT GAG TGG AAT GAT GAC TTT GTT ACA GCT      576
Gly Thr Lys Ile Tyr Gly Leu Glu Trp Asn Asp Asp Phe Val Thr Ala
            180                 185                 190

TAT ATT AGT GGT CGT TCT TAT CAC TTG AAC ATC AAT ACT AAT TGG TTT      624
Tyr Ile Ser Gly Arg Ser Tyr His Leu Asn Ile Asn Thr Asn Trp Phe
        195                 200                 205

AAC AAT GTC ACA CTT TTG TAT TCA CGC TCA AGC ACT GCT ACC TGG GAA      672
Asn Asn Val Thr Leu Leu Tyr Ser Arg Ser Ser Thr Ala Thr Trp Glu
    210                 215                 220

TAC AGT GCT GCA TAT GCT TAC CAA GGT GTT TCT AAC TTC ACT TAT TAC      720
Tyr Ser Ala Ala Tyr Ala Tyr Gln Gly Val Ser Asn Phe Thr Tyr Tyr
225                 230                 235                 240

AAG TTA AAT AAC ACC AAT GGT CTA AAA ACC TAT GAA TTA TGT GAA GAT      768
Lys Leu Asn Asn Thr Asn Gly Leu Lys Thr Tyr Glu Leu Cys Glu Asp
                245                 250                 255

TAT GAA CAT TGC ACT GGC TAT GCT ACC AAT GTA TTT GCT CCG ACA TCA      816
Tyr Glu His Cys Thr Gly Tyr Ala Thr Asn Val Phe Ala Pro Thr Ser
            260                 265                 270

GGT GGT TAC ATA CCT GAT GGA TTT AGT TTT AAT AAT TGG TTC TTG CTT      864
Gly Gly Tyr Ile Pro Asp Gly Phe Ser Phe Asn Asn Trp Phe Leu Leu
        275                 280                 285

ACA AAT AGT TCC ACT TTT GTT AGT GGC AGG TTT GTA ACA AAT CAA CCA      912
Thr Asn Ser Ser Thr Phe Val Ser Gly Arg Phe Val Thr Asn Gln Pro
    290                 295                 300

TTA TTG ATT AAT TGC TTG TGG CCA GTG CCC AGT TTT GGT GTA GCA GCA      960
Leu Leu Ile Asn Cys Leu Trp Pro Val Pro Ser Phe Gly Val Ala Ala
305                 310                 315                 320

CAA GAA TTT TGT TTT GAA GGT GCA CAG TTT AGC CAA TGT AAT GGT GTG     1008
Gln Glu Phe Cys Phe Glu Gly Ala Gln Phe Ser Gln Cys Asn Gly Val
                325                 330                 335

TCT TTA AAT AAC ACA GTG GAT GTT ATT AGA TTC AAC CTT AAT TTC ACT     1056
Ser Leu Asn Asn Thr Val Asp Val Ile Arg Phe Asn Leu Asn Phe Thr
            340                 345                 350

GCA GAT GTA CAA TCT GGT ATG GGT GCT ACA GTA TTT TCA CTG AAT ACA     1104
Ala Asp Val Gln Ser Gly Met Gly Ala Thr Val Phe Ser Leu Asn Thr
        355                 360                 365

ACA GGT GGT GTC ATT CTT GAA ATT TCA TGT TAT AGT GAC ACA GTG AGT     1152
Thr Gly Gly Val Ile Leu Glu Ile Ser Cys Tyr Ser Asp Thr Val Ser
    370                 375                 380

GAG TCT AGT TCT TAC AGT TAT GGT GAA ATC CCG TTC GGC ATA ACT GAC     1200
Glu Ser Ser Ser Tyr Ser Tyr Gly Glu Ile Pro Phe Gly Ile Thr Asp
385                 390                 395                 400

GGA CCA CGA TAC TGT TAT GTA CTT TAC AAT GGC ACA GCT CTT AAA TAT     1248
Gly Pro Arg Tyr Cys Tyr Val Leu Tyr Asn Gly Thr Ala Leu Lys Tyr
                405                 410                 415

TTA GGA ACA TTA CCA CCC AGT GTA AAG GAA ATT GCT ATT AGT AAG TGG     1296
Leu Gly Thr Leu Pro Pro Ser Val Lys Glu Ile Ala Ile Ser Lys Trp
            420                 425                 430

GGC CAT TTT TAT ATT AAT GGT TAC AAT TTC TTT AGC ACA TTT CCT ATT     1344
```

-continued

```
Gly His Phe Tyr Ile Asn Gly Tyr Asn Phe Phe Ser Thr Phe Pro Ile
        435                 440                 445

GAT TGT ATA TCT TTT AAT TTA ACC ACT GGT GTT AGT GGA GCT TTT TGG      1392
Asp Cys Ile Ser Phe Asn Leu Thr Thr Gly Val Ser Gly Ala Phe Trp
    450                 455                 460

ACA ATT GCT TAC ACA TCG TAT ACT GAA GCA TTA GTA CAA GTT GAA AAC      1440
Thr Ile Ala Tyr Thr Ser Tyr Thr Glu Ala Leu Val Gln Val Glu Asn
465                 470                 475                 480

ACA GCT ATT AAA AAT GTG ACG TAT TGT AAC AGT CAC ATT AAT AAC ATT      1488
Thr Ala Ile Lys Asn Val Thr Tyr Cys Asn Ser His Ile Asn Asn Ile
                485                 490                 495

AAA TGT TCT CAA CTT ACT GCT AAT TTG AAT AAT GGA TTT TAT CCT GTT      1536
Lys Cys Ser Gln Leu Thr Ala Asn Leu Asn Asn Gly Phe Tyr Pro Val
            500                 505                 510

GCT TCA AGT GAA GTA GGT TTC GTT AAT AAG AGT GTT GTG TTA TTA CCT      1584
Ala Ser Ser Glu Val Gly Phe Val Asn Lys Ser Val Val Leu Leu Pro
        515                 520                 525

AGC TTT TTC ACA TAC ACC GCT GTC AAT ATA ACC ATT GAT CTT GGT ATG      1632
Ser Phe Phe Thr Tyr Thr Ala Val Asn Ile Thr Ile Asp Leu Gly Met
    530                 535                 540

AAG CTT AGT GGT TAT GGT CAA CCC ATA GCC TCG ACA CTA AGT AAC ATC      1680
Lys Leu Ser Gly Tyr Gly Gln Pro Ile Ala Ser Thr Leu Ser Asn Ile
545                 550                 555                 560

ACA CTA CCA ATG CAG GAT AAC AAT ACT GAT GTG TAC TGT ATT CGT TCT      1728
Thr Leu Pro Met Gln Asp Asn Asn Thr Asp Val Tyr Cys Ile Arg Ser
                565                 570                 575

AAC CAA TTC TCA GTT TAT GTT CAT TCC ACT TGC AAA AGT TCT TTA TGG      1776
Asn Gln Phe Ser Val Tyr Val His Ser Thr Cys Lys Ser Ser Leu Trp
            580                 585                 590

GAC AAT ATT TTT AAT CAA GAC TGC ACG GAT GTT TTA GAG GCT ACA GCT      1824
Asp Asn Ile Phe Asn Gln Asp Cys Thr Asp Val Leu Glu Ala Thr Ala
        595                 600                 605

GTT ATA AAA ACT GGT ACT TGT CCT TTC TCA TTT GAT AAA TTG AAC AAT      1872
Val Ile Lys Thr Gly Thr Cys Pro Phe Ser Phe Asp Lys Leu Asn Asn
    610                 615                 620

TAC TTG ACT TTT AAC AAG TTC TGT TTG TCG TTG AGT CCT GTT GGT GCT      1920
Tyr Leu Thr Phe Asn Lys Phe Cys Leu Ser Leu Ser Pro Val Gly Ala
625                 630                 635                 640

AAT TGC AAG TTT GAT GTT GCT GCA CGT ACA AGA ACC AAT GAG CAG GTT      1968
Asn Cys Lys Phe Asp Val Ala Ala Arg Thr Arg Thr Asn Glu Gln Val
                645                 650                 655

GTT AGA AGT CTA TAT GTA ATA TAT GAA GAA GGA GAC AAC ATA GTG GGT      2016
Val Arg Ser Leu Tyr Val Ile Tyr Glu Glu Gly Asp Asn Ile Val Gly
            660                 665                 670

GTA CCG TCT GAT GAT AGC GGT CTG CAC GAT TTG TCT GTG CTA CAC CTA      2064
Val Pro Ser Asp Asp Ser Gly Leu His Asp Leu Ser Val Leu His Leu
        675                 680                 685

GAC TCC TGT ACA GAT TAC AAT ATA TAT GGT AGA ACT GGT GTT GGT ATT      2112
Asp Ser Cys Thr Asp Tyr Asn Ile Tyr Gly Arg Thr Gly Val Gly Ile
    690                 695                 700

ATT AGA CGA ACT AAC AGT ACG CTA CTT AGT GGC TTA TAT TAC ACA TCA      2160
Ile Arg Arg Thr Asn Ser Thr Leu Leu Ser Gly Leu Tyr Tyr Thr Ser
705                 710                 715                 720

CTA TCA GGT GAT TTG TTA GGC TTT AAA AAT GTT AGT GAT GGT GTC ATT      2208
Leu Ser Gly Asp Leu Leu Gly Phe Lys Asn Val Ser Asp Gly Val Ile
                725                 730                 735

TAT TCT GTG ACG CCA TGT GAT GTA AGC GCA CAA GCG GC                   2246
Tyr Ser Val Thr Pro Cys Asp Val Ser Ala Gln Ala
            740                 745
```

-continued (2) INFORMATION FOR SEQ ID NO:28:

(i) SEQUENCE CHARACTERISTICS:
(A) LENGTH: 748 amino acids
(B) TYPE: amino acid
(D) TOPOLOGY: linear (ii) MOLECULE TYPE: protein (xi) SEQUENCE DESCRIPTION: SEQ ID NO:28:

```
Met Ile Val Leu Val Thr Cys Leu Leu Leu Leu Cys Ser Tyr His Thr
  1               5                  10                  15

Val Leu Ser Thr Thr Asn Asn Glu Cys Ile Gln Val Asn Val Thr Gln
             20                  25                  30

Leu Ala Gly Asn Glu Asn Leu Ile Arg Asp Phe Leu Phe Ser Asn Phe
         35                  40                  45

Lys Glu Glu Gly Ser Val Val Val Gly Gly Tyr Tyr Pro Thr Glu Val
     50                  55                  60

Trp Tyr Asn Cys Ser Arg Thr Ala Arg Thr Thr Ala Phe Gln Tyr Phe
 65                  70                  75                  80

Asn Asn Ile His Ala Phe Tyr Phe Val Met Glu Ala Met Glu Asn Ser
                 85                  90                  95

Thr Gly Asn Ala Arg Gly Lys Pro Leu Leu Phe His Val His Gly Glu
            100                 105                 110

Pro Val Ser Val Ile Ile Tyr Ile Ser Ala Tyr Arg Asp Asp Val Gln
        115                 120                 125

Gln Arg Pro Leu Leu Lys His Gly Leu Val Cys Ile Thr Lys Asn Arg
    130                 135                 140

His Ile Asn Tyr Glu Gln Phe Thr Ser Asn Gln Trp Asn Ser Thr Cys
145                 150                 155                 160

Thr Gly Ala Asp Arg Lys Ile Pro Phe Ser Val Ile Pro Thr Asp Asn
                165                 170                 175

Gly Thr Lys Ile Tyr Gly Leu Glu Trp Asn Asp Asp Phe Val Thr Ala
            180                 185                 190

Tyr Ile Ser Gly Arg Ser Tyr His Leu Asn Ile Asn Thr Asn Trp Phe
        195                 200                 205

Asn Asn Val Thr Leu Leu Tyr Ser Arg Ser Ser Thr Ala Thr Trp Glu
    210                 215                 220

Tyr Ser Ala Ala Tyr Ala Tyr Gln Gly Val Ser Asn Phe Thr Tyr Tyr
225                 230                 235                 240

Lys Leu Asn Asn Thr Asn Gly Leu Lys Thr Tyr Glu Leu Cys Glu Asp
                245                 250                 255

Tyr Glu His Cys Thr Gly Tyr Ala Thr Asn Val Phe Ala Pro Thr Ser
            260                 265                 270

Gly Gly Tyr Ile Pro Asp Gly Phe Ser Phe Asn Asn Trp Phe Leu Leu
        275                 280                 285

Thr Asn Ser Ser Thr Phe Val Ser Gly Arg Phe Val Thr Asn Gln Pro
    290                 295                 300

Leu Leu Ile Asn Cys Leu Trp Pro Val Pro Ser Phe Gly Val Ala Ala
305                 310                 315                 320

Gln Glu Phe Cys Phe Glu Gly Ala Gln Phe Ser Gln Cys Asn Gly Val
                325                 330                 335

Ser Leu Asn Asn Thr Val Asp Val Ile Arg Phe Asn Leu Asn Phe Thr
            340                 345                 350

Ala Asp Val Gln Ser Gly Met Gly Ala Thr Val Phe Ser Leu Asn Thr
```

-continued

```
        355                 360                 365

Thr Gly Gly Val Ile Leu Glu Ile Ser Cys Tyr Ser Asp Thr Val Ser
    370                 375                 380

Glu Ser Ser Ser Tyr Ser Tyr Gly Glu Ile Pro Phe Gly Ile Thr Asp
385                 390                 395                 400

Gly Pro Arg Tyr Cys Tyr Val Leu Tyr Asn Gly Thr Ala Leu Lys Tyr
                405                 410                 415

Leu Gly Thr Leu Pro Pro Ser Val Lys Glu Ile Ala Ile Ser Lys Trp
            420                 425                 430

Gly His Phe Tyr Ile Asn Gly Tyr Asn Phe Phe Ser Thr Phe Pro Ile
        435                 440                 445

Asp Cys Ile Ser Phe Asn Leu Thr Thr Gly Val Ser Gly Ala Phe Trp
    450                 455                 460

Thr Ile Ala Tyr Thr Ser Tyr Thr Glu Ala Leu Val Gln Val Glu Asn
465                 470                 475                 480

Thr Ala Ile Lys Asn Val Thr Tyr Cys Asn Ser His Ile Asn Asn Ile
                485                 490                 495

Lys Cys Ser Gln Leu Thr Ala Asn Leu Asn Asn Gly Phe Tyr Pro Val
            500                 505                 510

Ala Ser Ser Glu Val Gly Phe Val Asn Lys Ser Val Val Leu Leu Pro
        515                 520                 525

Ser Phe Phe Thr Tyr Thr Ala Val Asn Ile Thr Ile Asp Leu Gly Met
    530                 535                 540

Lys Leu Ser Gly Tyr Gly Gln Pro Ile Ala Ser Thr Leu Ser Asn Ile
545                 550                 555                 560

Thr Leu Pro Met Gln Asp Asn Asn Thr Asp Val Tyr Cys Ile Arg Ser
                565                 570                 575

Asn Gln Phe Ser Val Tyr Val His Ser Thr Cys Lys Ser Ser Leu Trp
            580                 585                 590

Asp Asn Ile Phe Asn Gln Asp Cys Thr Asp Val Leu Glu Ala Thr Ala
        595                 600                 605

Val Ile Lys Thr Gly Thr Cys Pro Phe Ser Phe Asp Lys Leu Asn Asn
    610                 615                 620

Tyr Leu Thr Phe Asn Lys Phe Cys Leu Ser Leu Ser Pro Val Gly Ala
625                 630                 635                 640

Asn Cys Lys Phe Asp Val Ala Ala Arg Thr Arg Thr Asn Glu Gln Val
                645                 650                 655

Val Arg Ser Leu Tyr Val Ile Tyr Glu Glu Gly Asp Asn Ile Val Gly
            660                 665                 670

Val Pro Ser Asp Asp Ser Gly Leu His Asp Leu Ser Val Leu His Leu
        675                 680                 685

Asp Ser Cys Thr Asp Tyr Asn Ile Tyr Gly Arg Thr Gly Val Gly Ile
    690                 695                 700

Ile Arg Arg Thr Asn Ser Thr Leu Leu Ser Gly Leu Tyr Tyr Thr Ser
705                 710                 715                 720

Leu Ser Gly Asp Leu Leu Gly Phe Lys Asn Val Ser Asp Gly Val Ile
                725                 730                 735

Tyr Ser Val Thr Pro Cys Asp Val Ser Ala Gln Ala
            740                 745
```

(2) INFORMATION FOR SEQ ID NO:29:

(i) SEQUENCE CHARACTERISTICS:
(A) LENGTH: 370 base pairs

-continued

```
          (B) TYPE: nucleic acid
          (C) STRANDEDNESS: double
          (D) TOPOLOGY: unknown

    (ii) MOLECULE TYPE: cDNA

    (ix) FEATURE:
          (A) NAME/KEY: CDS
          (B) LOCATION: 3..368

    (xi) SEQUENCE DESCRIPTION: SEQ ID NO:29:

GT GGT AAA CCA TTA TTA TTT CAT GTG CAT GGT GAG CCT GTT AGT GTT        47
   Gly Lys Pro Leu Leu Phe His Val His Gly Glu Pro Val Ser Val
     1               5                  10                  15

ATT ATA TAT ATA TCG GCT TAT AGG GAT GAT GTG CAA CAA AGG CCC CTT       95
Ile Ile Tyr Ile Ser Ala Tyr Arg Asp Asp Val Gln Gln Arg Pro Leu
                 20                  25                  30

TTA AAA CAT GGG TTA GTG TGC ATA ACT AAA AAT CGC CAT ATT AAC TAT      143
Leu Lys His Gly Leu Val Cys Ile Thr Lys Asn Arg His Ile Asn Tyr
             35                  40                  45

GAA CAA TTC ACC TCC AAC CAG TGG AAT TCC ACA TGT ACG GGT GCT GAC      191
Glu Gln Phe Thr Ser Asn Gln Trp Asn Ser Thr Cys Thr Gly Ala Asp
         50                  55                  60

AGA AAA ATT CCT TTC TCT GTC ATA CCC ACG GAC AAT GGA ACA AAA ATC      239
Arg Lys Ile Pro Phe Ser Val Ile Pro Thr Asp Asn Gly Thr Lys Ile
     65                  70                  75

TAT GGT CTT GAG TGG AAT GAT GAC TTT GTT ACA GCT TAT ATT AGT GGT      287
Tyr Gly Leu Glu Trp Asn Asp Asp Phe Val Thr Ala Tyr Ile Ser Gly
 80                  85                  90                  95

CGT TCT TAT CAC TTG AAC ATC AAT ACT AAT TGG TTT AAC AAT GTC ACA      335
Arg Ser Tyr His Leu Asn Ile Asn Thr Asn Trp Phe Asn Asn Val Thr
                100                 105                 110

CTT TTG TAT TCA CGC TCA AGC ATT GCT ACC TGG GA                       370
Leu Leu Tyr Ser Arg Ser Ser Ile Ala Thr Trp
            115                 120


(2) INFORMATION FOR SEQ ID NO:30:

     (i) SEQUENCE CHARACTERISTICS:
          (A) LENGTH: 122 amino acids
          (B) TYPE: amino acid
          (D) TOPOLOGY: linear

    (ii) MOLECULE TYPE: protein

    (xi) SEQUENCE DESCRIPTION: SEQ ID NO:30:

Gly Lys Pro Leu Leu Phe His Val His Gly Glu Pro Val Ser Val Ile
  1               5                  10                  15

Ile Tyr Ile Ser Ala Tyr Arg Asp Asp Val Gln Gln Arg Pro Leu Leu
             20                  25                  30

Lys His Gly Leu Val Cys Ile Thr Lys Asn Arg His Ile Asn Tyr Glu
         35                  40                  45

Gln Phe Thr Ser Asn Gln Trp Asn Ser Thr Cys Thr Gly Ala Asp Arg
     50                  55                  60

Lys Ile Pro Phe Ser Val Ile Pro Thr Asp Asn Gly Thr Lys Ile Tyr
 65                  70                  75                  80

Gly Leu Glu Trp Asn Asp Asp Phe Val Thr Ala Tyr Ile Ser Gly Arg
                 85                  90                  95

Ser Tyr His Leu Asn Ile Asn Thr Asn Trp Phe Asn Asn Val Thr Leu
            100                 105                 110

Leu Tyr Ser Arg Ser Ser Ile Ala Thr Trp
        115                 120
```

-continued

```
(2) INFORMATION FOR SEQ ID NO:31:

     (i) SEQUENCE CHARACTERISTICS:
          (A) LENGTH: 4365 base pairs
          (B) TYPE: nucleic acid
          (C) STRANDEDNESS: double
          (D) TOPOLOGY: unknown

    (ii) MOLECULE TYPE: cDNA

    (ix) FEATURE:
          (A) NAME/KEY: CDS
          (B) LOCATION: 1..4362

    (xi) SEQUENCE DESCRIPTION: SEQ ID NO:31:

ATG ATT GTG CTC GTA ACT TGC CTC TTG TTG TTA TGC TCA TAC CAC ACT       48
Met Ile Val Leu Val Thr Cys Leu Leu Leu Leu Cys Ser Tyr His Thr
  1               5                  10                  15

GTT TCG AGT ACG TCA AAC AAT GAT TGT AGA CAA GTT AAC GTA ACA CAA       96
Val Ser Ser Thr Ser Asn Asn Asp Cys Arg Gln Val Asn Val Thr Gln
             20                  25                  30

TTA GCT GGC AAT GAA AAC CTT ATT AGA GAC TTT TTG TTT CAA AGT TTT      144
Leu Ala Gly Asn Glu Asn Leu Ile Arg Asp Phe Leu Phe Gln Ser Phe
         35                  40                  45

AAA GAA GAA GGA ATT GTA GTT GTT GGT GGT TAT TAC CCT ACA GAG GTG      192
Lys Glu Glu Gly Ile Val Val Val Gly Gly Tyr Tyr Pro Thr Glu Val
     50                  55                  60

TGG TAC AAC TGC TCT AGA ACA GCA ACT ACC ACT GCC TAT GAG TAT TTT      240
Trp Tyr Asn Cys Ser Arg Thr Ala Thr Thr Thr Ala Tyr Glu Tyr Phe
 65                  70                  75                  80

AAT AAT ATA CAT GCC TTT TAT TTT GAT ATG GAA GCT ATG GAA AAT AGC      288
Asn Asn Ile His Ala Phe Tyr Phe Asp Met Glu Ala Met Glu Asn Ser
                 85                  90                  95

ACT GGT AAT GCA CGT GGT AAA CCT CTA TTA TTT CAT GTT CAT GGT GAA      336
Thr Gly Asn Ala Arg Gly Lys Pro Leu Leu Phe His Val His Gly Glu
            100                 105                 110

CCT GTT AGT ATC ATC ATA TAT ATA TCA GCT TAT GGG GAT GAT GTG CAA      384
Pro Val Ser Ile Ile Ile Tyr Ile Ser Ala Tyr Gly Asp Asp Val Gln
        115                 120                 125

CAA AGG CCA CTT TTA GAA CAT GGG TTA TTG TGC ATT ACT AAA AAT CGC      432
Gln Arg Pro Leu Leu Glu His Gly Leu Leu Cys Ile Thr Lys Asn Arg
    130                 135                 140

AAT ATT GAC TAT AAC ACC TTC ACC AGC AAC CAG TGG GAT TCC ATA TGT      480
Asn Ile Asp Tyr Asn Thr Phe Thr Ser Asn Gln Trp Asp Ser Ile Cys
145                 150                 155                 160

ACG GGT AAT GAC AGA AAA ATT CCT TTC TCT GTC ATA CCC AGG GAT AAT      528
Thr Gly Asn Asp Arg Lys Ile Pro Phe Ser Val Ile Pro Arg Asp Asn
                165                 170                 175

GGA ACA AAA ATC TAT GGG CTT GAG TGG AAT GAT GAA TTT GTT ACA GCG      576
Gly Thr Lys Ile Tyr Gly Leu Glu Trp Asn Asp Glu Phe Val Thr Ala
            180                 185                 190

TAT ATT AGT GGT CGT TCT TAT AAT TGG AAC ATC AAT AAT AAC TGG TTT      624
Tyr Ile Ser Gly Arg Ser Tyr Asn Trp Asn Ile Asn Asn Asn Trp Phe
        195                 200                 205

AAC AAT GTC ACA CTT TTG TAT TCA CGC TCA AGC ACT GCT ACC TGG GAA      672
Asn Asn Val Thr Leu Leu Tyr Ser Arg Ser Ser Thr Ala Thr Trp Glu
    210                 215                 220

TAC AGT GCT GCA TAT GTT TAC CAA GGT GTT TCT AAC TTC ACT TAT TAC      720
Tyr Ser Ala Ala Tyr Val Tyr Gln Gly Val Ser Asn Phe Thr Tyr Tyr
225                 230                 235                 240

AAG TTA AAT AAC ACC AAT GGT TTA AAA ACC TAT GAA TTT TGT GAG GAT      768
```

-continued

```
Lys Leu Asn Asn Thr Asn Gly Leu Lys Thr Tyr Glu Phe Cys Glu Asp
                245                 250                 255

TAT GAA TAT TGC ACT GGC TAC GCC ACT AAT GTC TTT GCT CCA ACT GTG      816
Tyr Glu Tyr Cys Thr Gly Tyr Ala Thr Asn Val Phe Ala Pro Thr Val
            260                 265                 270

GGA GGT TAC ATA CCT GAT GGA TTT AGT TTT AAC AAT TGG TTT TTG CTT      864
Gly Gly Tyr Ile Pro Asp Gly Phe Ser Phe Asn Asn Trp Phe Leu Leu
        275                 280                 285

ACA AAT AGC TCC ACT TTT GTT AGT GGC AGA TTT GTA ACA AAC CAA CCA      912
Thr Asn Ser Ser Thr Phe Val Ser Gly Arg Phe Val Thr Asn Gln Pro
    290                 295                 300

CTA TTA GTT AAC TGC TTA TGG CCA GTG CCC AGT TTT GGT GTA GCA GCA      960
Leu Leu Val Asn Cys Leu Trp Pro Val Pro Ser Phe Gly Val Ala Ala
305                 310                 315                 320

CAA GAA TTT TGT TTT GAA GGT GCG CAG TTT AGT CAG TGT AGT GGT GTA     1008
Gln Glu Phe Cys Phe Glu Gly Ala Gln Phe Ser Gln Cys Ser Gly Val
                325                 330                 335

TCT TTA AAT AAC ACA GTA GAT GTT ATT AGA TTC AAT CTT AAT TTC ACC     1056
Ser Leu Asn Asn Thr Val Asp Val Ile Arg Phe Asn Leu Asn Phe Thr
            340                 345                 350

GCA GAT GTA CAA TCT GGT ATG GGT GCT ACA GTG TTT TCG TTG AAT ACA     1104
Ala Asp Val Gln Ser Gly Met Gly Ala Thr Val Phe Ser Leu Asn Thr
        355                 360                 365

ACG GGT GGT GTC ATT CTT GAA GTT TCA TGT TAT AAT GAC ACA GTG AGT     1152
Thr Gly Gly Val Ile Leu Glu Val Ser Cys Tyr Asn Asp Thr Val Ser
    370                 375                 380

GAG TCT AGT TTT TAC AGT TAT GGT GAA ATT CCG TTC GGC ATA ACT GAT     1200
Glu Ser Ser Phe Tyr Ser Tyr Gly Glu Ile Pro Phe Gly Ile Thr Asp
385                 390                 395                 400

GGA CCA CGG TAC TGT TAT GTA CTT TAC AAT GGC ACA GCT CTT AAG TAT     1248
Gly Pro Arg Tyr Cys Tyr Val Leu Tyr Asn Gly Thr Ala Leu Lys Tyr
                405                 410                 415

TTA GGA ACA TTA CCA CCT AGT GTA AAG GAA ATT GCT ATT AGT AAG TGG     1296
Leu Gly Thr Leu Pro Pro Ser Val Lys Glu Ile Ala Ile Ser Lys Trp
            420                 425                 430

GGC CAT TTT TAT ATT AAT GGT TAC AAT TTC TTT AGC ACA TTT CCT ATT     1344
Gly His Phe Tyr Ile Asn Gly Tyr Asn Phe Phe Ser Thr Phe Pro Ile
        435                 440                 445

GAT TGT ATA TCT TTT AAC TTA ACC ACT GGT GAT AGT GGA GCT TTT TGG     1392
Asp Cys Ile Ser Phe Asn Leu Thr Thr Gly Asp Ser Gly Ala Phe Trp
    450                 455                 460

ACA ATT GCT TAC ACA TCG TAC ACT GAG GCA TTA GTA CAA GTT GAA AAC     1440
Thr Ile Ala Tyr Thr Ser Tyr Thr Glu Ala Leu Val Gln Val Glu Asn
465                 470                 475                 480

ACA GCT ATT AAA AAG GTG ACG TAT TGT AAC AGT CAC ATT AAT AAC ATT     1488
Thr Ala Ile Lys Lys Val Thr Tyr Cys Asn Ser His Ile Asn Asn Ile
                485                 490                 495

AAG TGT TCT CAA CTT ACT GCT AAT TTG AAT AAT GGA TTT TAT CCT GTT     1536
Lys Cys Ser Gln Leu Thr Ala Asn Leu Asn Asn Gly Phe Tyr Pro Val
            500                 505                 510

GCT TCA AGT GAG GTT GGT CTT GTG AAT AAG AGT GTT GTG TTA TTA CCT     1584
Ala Ser Ser Glu Val Gly Leu Val Asn Lys Ser Val Val Leu Leu Pro
        515                 520                 525

ATC TTT TTC GCA CAT ACC GCT ATC AAT ATA ACC ATT GAT CTT GGT ATG     1632
Ile Phe Phe Ala His Thr Ala Ile Asn Ile Thr Ile Asp Leu Gly Met
    530                 535                 540

AAG CGT AGC GGT TAT GGT CAA CCC ATA GCA TCA ACA TTA AGT AAC ATT     1680
Lys Arg Ser Gly Tyr Gly Gln Pro Ile Ala Ser Thr Leu Ser Asn Ile
545                 550                 555                 560
```

-continued

```
ACA CTA CCA ATG CAG GAT AAT AAC ACA GAT GTG TAC TGT ATT CGT TCT      1728
Thr Leu Pro Met Gln Asp Asn Asn Thr Asp Val Tyr Cys Ile Arg Ser
                565                 570                 575

AAC CAG TTT TCA GTT TAT GTT CAT TCT ATT TGT AAG AGT TCT TTA TGG      1776
Asn Gln Phe Ser Val Tyr Val His Ser Ile Cys Lys Ser Ser Leu Trp
            580                 585                 590

GAC AAT ATT TTT AAT CAA GAA TGC ACG GAT GTT TTA GAT GCC ACA GCT      1824
Asp Asn Ile Phe Asn Gln Glu Cys Thr Asp Val Leu Asp Ala Thr Ala
        595                 600                 605

GTT ATA AAG ACT GGT ACT TGT CCT TTC TCA TTT GAT AAA TTG AAC AAT      1872
Val Ile Lys Thr Gly Thr Cys Pro Phe Ser Phe Asp Lys Leu Asn Asn
    610                 615                 620

TAC TTA ACT TTT AAC AAG TTC TGT TTG TCG TTG AGT CCT GTT GGC GCT      1920
Tyr Leu Thr Phe Asn Lys Phe Cys Leu Ser Leu Ser Pro Val Gly Ala
625                 630                 635                 640

AAC TGC AAG TTT GAT GTT GCC GCA CGT ACA AGA ACC AAT GAG CAA GTT      1968
Asn Cys Lys Phe Asp Val Ala Ala Arg Thr Arg Thr Asn Glu Gln Val
                645                 650                 655

GTT AGA AGT CTA TAT GTA ATA TAT GAA GAA GGA GAC AAC ATA GTT GGT      2016
Val Arg Ser Leu Tyr Val Ile Tyr Glu Glu Gly Asp Asn Ile Val Gly
            660                 665                 670

GTA CCG TCT GAT AAT AGC GGT CTG CAC GAT TTG TCT GTG CTA CAC CTA      2064
Val Pro Ser Asp Asn Ser Gly Leu His Asp Leu Ser Val Leu His Leu
        675                 680                 685

GAC TCC TGT ACA GAG TAT AAT ATA TAT GGT AGA ACT GGT GTT GGT ATT      2112
Asp Ser Cys Thr Glu Tyr Asn Ile Tyr Gly Arg Thr Gly Val Gly Ile
    690                 695                 700

ATT AGA CAA ACT AAC AGT ACG CTA CTT AGC GGC TTA TAT TAC ACA TCA      2160
Ile Arg Gln Thr Asn Ser Thr Leu Leu Ser Gly Leu Tyr Tyr Thr Ser
705                 710                 715                 720

CTA TCA GGT GAT TTG TTA GGC TTT AAA AAT GTT AGT GAT GGT GTC ATC      2208
Leu Ser Gly Asp Leu Leu Gly Phe Lys Asn Val Ser Asp Gly Val Ile
                725                 730                 735

TAT TCT GTG ACG CCA TGT GAT GTA AGC GCA CAA GCG GCT GTT ATT GAT      2256
Tyr Ser Val Thr Pro Cys Asp Val Ser Ala Gln Ala Ala Val Ile Asp
            740                 745                 750

GGT GCC ATA GTT GGA GCT ATG ACT TCC ATT AAC AGT GAA CTG TTA GGT      2304
Gly Ala Ile Val Gly Ala Met Thr Ser Ile Asn Ser Glu Leu Leu Gly
        755                 760                 765

CTA AAA CAC TGG ACA ACA ACA CCT AAT TTT TAT TAC TAC TCT ATA TAT      2352
Leu Lys His Trp Thr Thr Thr Pro Asn Phe Tyr Tyr Tyr Ser Ile Tyr
    770                 775                 780

AAT TAT ACA AAT GAG AGG ACT CGT GGC ACT GCA ATT GAC AGT AAC GAT      2400
Asn Tyr Thr Asn Glu Arg Thr Arg Gly Thr Ala Ile Asp Ser Asn Asp
785                 790                 795                 800

GTT GAT TGT GAA CCT ATC ATA ACC TAT TCT AAC ATA GGT GTT TGT AAA      2448
Val Asp Cys Glu Pro Ile Ile Thr Tyr Ser Asn Ile Gly Val Cys Lys
                805                 810                 815

AAT GGT GCT TTG GTT TTT ATT AAC GTC ACA CAT TCT GAT GGA GAC GTG      2496
Asn Gly Ala Leu Val Phe Ile Asn Val Thr His Ser Asp Gly Asp Val
            820                 825                 830

CAA CCA ATT AGC ACT GGT ACT GTC ACG ATA CCT ACA AAC TTT ACC ATA      2544
Gln Pro Ile Ser Thr Gly Thr Val Thr Ile Pro Thr Asn Phe Thr Ile
        835                 840                 845

TCT GTG CAA GTC GAA TAC ATT CAG GTT TAC ACC ACA CCA GTA TCA ATA      2592
Ser Val Gln Val Glu Tyr Ile Gln Val Tyr Thr Thr Pro Val Ser Ile
    850                 855                 860

GAT TGT GCA AGA TAC GTT TGC AAT GGT AAC CCT AGA TGT AAC AAA TTG      2640
Asp Cys Ala Arg Tyr Val Cys Asn Gly Asn Pro Arg Cys Asn Lys Leu
865                 870                 875                 880
```

-continued

```
TTA ACA CAA TAT GTT TCT GCA TGT CAA ACT ATT GAG CAA GCA CTT GCA     2688
Leu Thr Gln Tyr Val Ser Ala Cys Gln Thr Ile Glu Gln Ala Leu Ala
                885                 890                 895

ATG GGT GCC AGA CTT GAA AAC ATG GAG GTT GAT TCC ATG TTG TTC GTT     2736
Met Gly Ala Arg Leu Glu Asn Met Glu Val Asp Ser Met Leu Phe Val
            900                 905                 910

TCT GAA AAT GCC CTT AAA TTG GCA TCT GTT GAG GCG TTC AAT AGT ACA     2784
Ser Glu Asn Ala Leu Lys Leu Ala Ser Val Glu Ala Phe Asn Ser Thr
        915                 920                 925

GAA AAT TTA GAC CCT ATT TAC AAA GAA TGG CCT AAC ATA GGT GGT TCT     2832
Glu Asn Leu Asp Pro Ile Tyr Lys Glu Trp Pro Asn Ile Gly Gly Ser
    930                 935                 940

TGG TTA GGA GGT TTA AAA GAC ATA CTG CCG TCC CAT AAT AGC AAA CGT     2880
Trp Leu Gly Gly Leu Lys Asp Ile Leu Pro Ser His Asn Ser Lys Arg
945                 950                 955                 960

AAG TAT CGT TCT GCT ATA GAA GAC TTG CTT TTT GAT AAG GTT GTA ACT     2928
Lys Tyr Arg Ser Ala Ile Glu Asp Leu Leu Phe Asp Lys Val Val Thr
                965                 970                 975

TCT GGT TTA GGT ACA GTT GAT GAA GAT TAT AAA CGT TGT ACA GGT GGT     2976
Ser Gly Leu Gly Thr Val Asp Glu Asp Tyr Lys Arg Cys Thr Gly Gly
            980                 985                 990

TAT GAC ATA GCC GAC TTA GTG TGT GCT CAA TAT TAC AAT GGC ATC ATG     3024
Tyr Asp Ile Ala Asp Leu Val Cys Ala Gln Tyr Tyr Asn Gly Ile Met
        995                 1000                1005

GTG TTA CCT GGT GTA GCT AAT GAT GAC AAG ATG ACT ATG TAC ACA GCA     3072
Val Leu Pro Gly Val Ala Asn Asp Asp Lys Met Thr Met Tyr Thr Ala
    1010                1015                1020

TCT CTT GCA GGT GGT ATA ACA CTA GGT GCA CTT GGT GGT GGC GCC GTT     3120
Ser Leu Ala Gly Gly Ile Thr Leu Gly Ala Leu Gly Gly Gly Ala Val
1025                1030                1035                1040

GCT ATA CCT TTT GCA GTA GCA GTT CAA GCT AGA CTT AAT TAT GTT GCT     3168
Ala Ile Pro Phe Ala Val Ala Val Gln Ala Arg Leu Asn Tyr Val Ala
                1045                1050                1055

CTA CAA ACT GAT GTA TTG AAT AAA AAC CAG CAG ATC CTG GCT AAT GCT     3216
Leu Gln Thr Asp Val Leu Asn Lys Asn Gln Gln Ile Leu Ala Asn Ala
            1060                1065                1070

TTC AAT CAA GCT ATT GGT AAC ATT ACA CAG GCA TTT GGC AAG GTT AAT     3264
Phe Asn Gln Ala Ile Gly Asn Ile Thr Gln Ala Phe Gly Lys Val Asn
        1075                1080                1085

GAT GCT ATA CAT CAA ACA TCA AAA GGT CTT GCA ACT GTT GCT AAA GCA     3312
Asp Ala Ile His Gln Thr Ser Lys Gly Leu Ala Thr Val Ala Lys Ala
    1090                1095                1100

TTG GCA AAA GTG CAA GAT GTT GTC AAC ACA CAA GGG CAA GCT TTA AGC     3360
Leu Ala Lys Val Gln Asp Val Val Asn Thr Gln Gly Gln Ala Leu Ser
1105                1110                1115                1120

CAC CTA ACA GTA CAA TTG CAA AAT AAT TTT CAA GCC ATT AGT AGC TCT     3408
His Leu Thr Val Gln Leu Gln Asn Asn Phe Gln Ala Ile Ser Ser Ser
                1125                1130                1135

ATT AGT GAT ATT TAT AAC AGG CTT GAC GAA CTG AGT GCT GAT GCA CAA     3456
Ile Ser Asp Ile Tyr Asn Arg Leu Asp Glu Leu Ser Ala Asp Ala Gln
            1140                1145                1150

GTT GAT AGG CTG ATT ACA GGA AGA CTT ACA GCA CTT AAT GCA TTT GTG     3504
Val Asp Arg Leu Ile Thr Gly Arg Leu Thr Ala Leu Asn Ala Phe Val
        1155                1160                1165

TCT CAG ACT CTA ACC AGA CAA GCG GAG GTT AGG GCT AGT AGA CAA CTT     3552
Ser Gln Thr Leu Thr Arg Gln Ala Glu Val Arg Ala Ser Arg Gln Leu
    1170                1175                1180

GCC AAG GAC AAG GTT AAT GAA TGT GTT AGA TCC CAA TCT CAG AGA TTT     3600
Ala Lys Asp Lys Val Asn Glu Cys Val Arg Ser Gln Ser Gln Arg Phe
```

-continued

```
1185                1190                1195                1200

GGA TTC TGT GGT AAT GGT ACA CAC TTG TTT TCA CTT GCA AAT GCA GCA     3648
Gly Phe Cys Gly Asn Gly Thr His Leu Phe Ser Leu Ala Asn Ala Ala
                1205                1210                1215

CCA AAT GGC ATG ATT TTC TTT CAT ACA GTG CTA TTA CCA ACG GCT TAT     3696
Pro Asn Gly Met Ile Phe Phe His Thr Val Leu Leu Pro Thr Ala Tyr
            1220                1225                1230

GAA ACT GTA ACA GCT TGG CCA GGT ATT TGT GCT TCA GAT GGC GAT CGC     3744
Glu Thr Val Thr Ala Trp Pro Gly Ile Cys Ala Ser Asp Gly Asp Arg
        1235                1240                1245

ACT TTT GGA CTT GTC GTT AAA GAT GTA CAG TTG ACG TTG TTT CGT AAC     3792
Thr Phe Gly Leu Val Val Lys Asp Val Gln Leu Thr Leu Phe Arg Asn
    1250                1255                1260

CTA GAT GAC AAG TTC TAT TTG ACT CCC AGA ACT ATG TAT CAG CCT AGA     3840
Leu Asp Asp Lys Phe Tyr Leu Thr Pro Arg Thr Met Tyr Gln Pro Arg
1265                1270                1275                1280

GCT GCA ACT AGT TCT GAT TTT GTT CAA ATT GAG GGG TGC GAT GTG TTG     3888
Ala Ala Thr Ser Ser Asp Phe Val Gln Ile Glu Gly Cys Asp Val Leu
                1285                1290                1295

TTT GTC AAT GCA ACT GTA ATT GAC TTG CCT AGT ATT ATA CCT GAC TAT     3936
Phe Val Asn Ala Thr Val Ile Asp Leu Pro Ser Ile Ile Pro Asp Tyr
            1300                1305                1310

ATT GAC ATC AAT CAG ACT GTT CAA GAT ATA TTA GAA AAT TAC AGA CCA     3984
Ile Asp Ile Asn Gln Thr Val Gln Asp Ile Leu Glu Asn Tyr Arg Pro
        1315                1320                1325

AAC TGG ACT GTA CCT GAA TTG ACA CTT GAT ATT TTT AAC GCA ACC TAT     4032
Asn Trp Thr Val Pro Glu Leu Thr Leu Asp Ile Phe Asn Ala Thr Tyr
    1330                1335                1340

TTA AAT CTG ACT GGT GAA ATT GAT GAC TTA GAA TTT AGG TCA GAA AAG     4080
Leu Asn Leu Thr Gly Glu Ile Asp Asp Leu Glu Phe Arg Ser Glu Lys
1345                1350                1355                1360

CTA CAC AAT ACC ACT GTA GAA CTT GCC ATT CTC ATT GAC AAC ATT AAC     4128
Leu His Asn Thr Thr Val Glu Leu Ala Ile Leu Ile Asp Asn Ile Asn
                1365                1370                1375

AAC ACA TTA GTC AAT CTT GAA TGG CTC AAT AGA ATT GAA ACT TAT GTA     4176
Asn Thr Leu Val Asn Leu Glu Trp Leu Asn Arg Ile Glu Thr Tyr Val
            1380                1385                1390

AAA TGG CCT TGG TAT GTG TGG CTA CTA ATA GGC TTA GTA GTA ATA TTT     4224
Lys Trp Pro Trp Tyr Val Trp Leu Leu Ile Gly Leu Val Val Ile Phe
        1395                1400                1405

TGC ATA CCA TTA TTG CTA TTT TGC TGT TGT AGT ACA GGT TGT TGT GGA     4272
Cys Ile Pro Leu Leu Leu Phe Cys Cys Cys Ser Thr Gly Cys Cys Gly
    1410                1415                1420

TGC ATA GGT TGC TTA GGA AGT TGT TGT CAC TCT ATG TGT AGT AGA AGA     4320
Cys Ile Gly Cys Leu Gly Ser Cys Cys His Ser Met Cys Ser Arg Arg
1425                1430                1435                1440

CAA TTT GAA AAT TAT GAA CCA ATT GAA AAA GTG CAT GTC CAC             4362
Gln Phe Glu Asn Tyr Glu Pro Ile Glu Lys Val His Val His
                1445                1450

TAA                                                                 4365
```

(2) INFORMATION FOR SEQ ID NO:32:

(i) SEQUENCE CHARACTERISTICS:
(A) LENGTH: 1454 amino acids
(B) TYPE: amino acid
(D) TOPOLOGY: linear (ii) MOLECULE TYPE: protein (xi) SEQUENCE DESCRIPTION: SEQ ID NO:32:

-continued

Met Ile Val Leu Val Thr Cys Leu Leu Leu Leu Cys Ser Tyr His Thr
1 5 10 15

Val Ser Ser Thr Ser Asn Asn Asp Cys Arg Gln Val Asn Val Thr Gln
20 25 30

Leu Ala Gly Asn Glu Asn Leu Ile Arg Asp Phe Leu Phe Gln Ser Phe
35 40 45

Lys Glu Glu Gly Ile Val Val Val Gly Gly Tyr Tyr Pro Thr Glu Val
50 55 60

Trp Tyr Asn Cys Ser Arg Thr Ala Thr Thr Thr Ala Tyr Glu Tyr Phe
65 70 75 80

Asn Asn Ile His Ala Phe Tyr Phe Asp Met Glu Ala Met Glu Asn Ser
85 90 95

Thr Gly Asn Ala Arg Gly Lys Pro Leu Leu Phe His Val His Gly Glu
100 105 110

Pro Val Ser Ile Ile Ile Tyr Ile Ser Ala Tyr Gly Asp Asp Val Gln
115 120 125

Gln Arg Pro Leu Leu Glu His Gly Leu Leu Cys Ile Thr Lys Asn Arg
130 135 140

Asn Ile Asp Tyr Asn Thr Phe Thr Ser Asn Gln Trp Asp Ser Ile Cys
145 150 155 160

Thr Gly Asn Asp Arg Lys Ile Pro Phe Ser Val Ile Pro Arg Asp Asn
165 170 175

Gly Thr Lys Ile Tyr Gly Leu Glu Trp Asn Asp Glu Phe Val Thr Ala
180 185 190

Tyr Ile Ser Gly Arg Ser Tyr Asn Trp Asn Ile Asn Asn Asn Trp Phe
195 200 205

Asn Asn Val Thr Leu Leu Tyr Ser Arg Ser Ser Thr Ala Thr Trp Glu
210 215 220

Tyr Ser Ala Ala Tyr Val Tyr Gln Gly Val Ser Asn Phe Thr Tyr Tyr
225 230 235 240

Lys Leu Asn Asn Thr Asn Gly Leu Lys Thr Tyr Glu Phe Cys Glu Asp
245 250 255

Tyr Glu Tyr Cys Thr Gly Tyr Ala Thr Asn Val Phe Ala Pro Thr Val
260 265 270

Gly Gly Tyr Ile Pro Asp Gly Phe Ser Phe Asn Asn Trp Phe Leu Leu
275 280 285

Thr Asn Ser Ser Thr Phe Val Ser Gly Arg Phe Val Thr Asn Gln Pro
290 295 300

Leu Leu Val Asn Cys Leu Trp Pro Val Pro Ser Phe Gly Val Ala Ala
305 310 315 320

Gln Glu Phe Cys Phe Glu Gly Ala Gln Phe Ser Gln Cys Ser Gly Val
325 330 335

Ser Leu Asn Asn Thr Val Asp Val Ile Arg Phe Asn Leu Asn Phe Thr
340 345 350

Ala Asp Val Gln Ser Gly Met Gly Ala Thr Val Phe Ser Leu Asn Thr
355 360 365

Thr Gly Gly Val Ile Leu Glu Val Ser Cys Tyr Asn Asp Thr Val Ser
370 375 380

Glu Ser Ser Phe Tyr Ser Tyr Gly Glu Ile Pro Phe Gly Ile Thr Asp
385 390 395 400

Gly Pro Arg Tyr Cys Tyr Val Leu Tyr Asn Gly Thr Ala Leu Lys Tyr
405 410 415

-continued

```
Leu Gly Thr Leu Pro Pro Ser Val Lys Glu Ile Ala Ile Ser Lys Trp
            420                 425                 430

Gly His Phe Tyr Ile Asn Gly Tyr Asn Phe Phe Ser Thr Phe Pro Ile
        435                 440                 445

Asp Cys Ile Ser Phe Asn Leu Thr Thr Gly Asp Ser Gly Ala Phe Trp
    450                 455                 460

Thr Ile Ala Tyr Thr Ser Tyr Thr Glu Ala Leu Val Gln Val Glu Asn
465                 470                 475                 480

Thr Ala Ile Lys Lys Val Thr Tyr Cys Asn Ser His Ile Asn Asn Ile
                485                 490                 495

Lys Cys Ser Gln Leu Thr Ala Asn Leu Asn Asn Gly Phe Tyr Pro Val
            500                 505                 510

Ala Ser Ser Glu Val Gly Leu Val Asn Lys Ser Val Val Leu Leu Pro
        515                 520                 525

Ile Phe Phe Ala His Thr Ala Ile Asn Ile Thr Ile Asp Leu Gly Met
    530                 535                 540

Lys Arg Ser Gly Tyr Gly Gln Pro Ile Ala Ser Thr Leu Ser Asn Ile
545                 550                 555                 560

Thr Leu Pro Met Gln Asp Asn Asn Thr Asp Val Tyr Cys Ile Arg Ser
                565                 570                 575

Asn Gln Phe Ser Val Tyr Val His Ser Ile Cys Lys Ser Ser Leu Trp
            580                 585                 590

Asp Asn Ile Phe Asn Gln Glu Cys Thr Asp Val Leu Asp Ala Thr Ala
        595                 600                 605

Val Ile Lys Thr Gly Thr Cys Pro Phe Ser Phe Asp Lys Leu Asn Asn
    610                 615                 620

Tyr Leu Thr Phe Asn Lys Phe Cys Leu Ser Leu Ser Pro Val Gly Ala
625                 630                 635                 640

Asn Cys Lys Phe Asp Val Ala Ala Arg Thr Arg Thr Asn Glu Gln Val
                645                 650                 655

Val Arg Ser Leu Tyr Val Ile Tyr Glu Glu Gly Asp Asn Ile Val Gly
            660                 665                 670

Val Pro Ser Asp Asn Ser Gly Leu His Asp Leu Ser Val Leu His Leu
        675                 680                 685

Asp Ser Cys Thr Glu Tyr Asn Ile Tyr Gly Arg Thr Gly Val Gly Ile
    690                 695                 700

Ile Arg Gln Thr Asn Ser Thr Leu Leu Ser Gly Leu Tyr Tyr Thr Ser
705                 710                 715                 720

Leu Ser Gly Asp Leu Leu Gly Phe Lys Asn Val Ser Asp Gly Val Ile
                725                 730                 735

Tyr Ser Val Thr Pro Cys Asp Val Ser Ala Gln Ala Ala Val Ile Asp
            740                 745                 750

Gly Ala Ile Val Gly Ala Met Thr Ser Ile Asn Ser Glu Leu Leu Gly
        755                 760                 765

Leu Lys His Trp Thr Thr Thr Pro Asn Phe Tyr Tyr Tyr Ser Ile Tyr
    770                 775                 780

Asn Tyr Thr Asn Glu Arg Thr Arg Gly Thr Ala Ile Asp Ser Asn Asp
785                 790                 795                 800

Val Asp Cys Glu Pro Ile Ile Thr Tyr Ser Asn Ile Gly Val Cys Lys
                805                 810                 815

Asn Gly Ala Leu Val Phe Ile Asn Val Thr His Ser Asp Gly Asp Val
            820                 825                 830

Gln Pro Ile Ser Thr Gly Thr Val Thr Ile Pro Thr Asn Phe Thr Ile
```

-continued

```
        835                 840                 845

Ser Val Gln Val Glu Tyr Ile Gln Val Tyr Thr Thr Pro Val Ser Ile
    850                 855                 860

Asp Cys Ala Arg Tyr Val Cys Asn Gly Asn Pro Arg Cys Asn Lys Leu
865                 870                 875                 880

Leu Thr Gln Tyr Val Ser Ala Cys Gln Thr Ile Glu Gln Ala Leu Ala
                885                 890                 895

Met Gly Ala Arg Leu Glu Asn Met Glu Val Asp Ser Met Leu Phe Val
            900                 905                 910

Ser Glu Asn Ala Leu Lys Leu Ala Ser Val Glu Ala Phe Asn Ser Thr
        915                 920                 925

Glu Asn Leu Asp Pro Ile Tyr Lys Glu Trp Pro Asn Ile Gly Gly Ser
    930                 935                 940

Trp Leu Gly Gly Leu Lys Asp Ile Leu Pro Ser His Asn Ser Lys Arg
945                 950                 955                 960

Lys Tyr Arg Ser Ala Ile Glu Asp Leu Leu Phe Asp Lys Val Val Thr
                965                 970                 975

Ser Gly Leu Gly Thr Val Asp Glu Asp Tyr Lys Arg Cys Thr Gly Gly
            980                 985                 990

Tyr Asp Ile Ala Asp Leu Val Cys Ala Gln Tyr Tyr Asn Gly Ile Met
        995                 1000                1005

Val Leu Pro Gly Val Ala Asn Asp Asp Lys Met Thr Met Tyr Thr Ala
    1010                1015                1020

Ser Leu Ala Gly Gly Ile Thr Leu Gly Ala Leu Gly Gly Gly Ala Val
1025                1030                1035                1040

Ala Ile Pro Phe Ala Val Ala Val Gln Ala Arg Leu Asn Tyr Val Ala
                1045                1050                1055

Leu Gln Thr Asp Val Leu Asn Lys Asn Gln Gln Ile Leu Ala Asn Ala
            1060                1065                1070

Phe Asn Gln Ala Ile Gly Asn Ile Thr Gln Ala Phe Gly Lys Val Asn
        1075                1080                1085

Asp Ala Ile His Gln Thr Ser Lys Gly Leu Ala Thr Val Ala Lys Ala
    1090                1095                1100

Leu Ala Lys Val Gln Asp Val Val Asn Thr Gln Gly Gln Ala Leu Ser
1105                1110                1115                1120

His Leu Thr Val Gln Leu Gln Asn Asn Phe Gln Ala Ile Ser Ser Ser
                1125                1130                1135

Ile Ser Asp Ile Tyr Asn Arg Leu Asp Glu Leu Ser Ala Asp Ala Gln
            1140                1145                1150

Val Asp Arg Leu Ile Thr Gly Arg Leu Thr Ala Leu Asn Ala Phe Val
        1155                1160                1165

Ser Gln Thr Leu Thr Arg Gln Ala Glu Val Arg Ala Ser Arg Gln Leu
    1170                1175                1180

Ala Lys Asp Lys Val Asn Glu Cys Val Arg Ser Gln Ser Gln Arg Phe
1185                1190                1195                1200

Gly Phe Cys Gly Asn Gly Thr His Leu Phe Ser Leu Ala Asn Ala Ala
                1205                1210                1215

Pro Asn Gly Met Ile Phe Phe His Thr Val Leu Leu Pro Thr Ala Tyr
            1220                1225                1230

Glu Thr Val Thr Ala Trp Pro Gly Ile Cys Ala Ser Asp Gly Asp Arg
        1235                1240                1245

Thr Phe Gly Leu Val Val Lys Asp Val Gln Leu Thr Leu Phe Arg Asn
    1250                1255                1260
```

-continued

```
Leu Asp Asp Lys Phe Tyr Leu Thr Pro Arg Thr Met Tyr Gln Pro Arg
1265                1270                1275                1280

Ala Ala Thr Ser Ser Asp Phe Val Gln Ile Glu Gly Cys Asp Val Leu
                1285                1290                1295

Phe Val Asn Ala Thr Val Ile Asp Leu Pro Ser Ile Ile Pro Asp Tyr
            1300                1305                1310

Ile Asp Ile Asn Gln Thr Val Gln Asp Ile Leu Glu Asn Tyr Arg Pro
        1315                1320                1325

Asn Trp Thr Val Pro Glu Leu Thr Leu Asp Ile Phe Asn Ala Thr Tyr
    1330                1335                1340

Leu Asn Leu Thr Gly Glu Ile Asp Asp Leu Glu Phe Arg Ser Glu Lys
1345                1350                1355                1360

Leu His Asn Thr Thr Val Glu Leu Ala Ile Leu Ile Asp Asn Ile Asn
                1365                1370                1375

Asn Thr Leu Val Asn Leu Glu Trp Leu Asn Arg Ile Glu Thr Tyr Val
            1380                1385                1390

Lys Trp Pro Trp Tyr Val Trp Leu Leu Ile Gly Leu Val Val Ile Phe
        1395                1400                1405

Cys Ile Pro Leu Leu Leu Phe Cys Cys Cys Ser Thr Gly Cys Cys Gly
    1410                1415                1420

Cys Ile Gly Cys Leu Gly Ser Cys Cys His Ser Met Cys Ser Arg Arg
1425                1430                1435                1440

Gln Phe Glu Asn Tyr Glu Pro Ile Glu Lys Val His Val His
                1445                1450
```

(2) INFORMATION FOR SEQ ID NO:33:

(i) SEQUENCE CHARACTERISTICS:
(A) LENGTH: 2246 base pairs
(B) TYPE: nucleic acid
(C) STRANDEDNESS: unknown
(D) TOPOLOGY: unknown (ii) MOLECULE TYPE: cDNA (ix) FEATURE:
(A) NAME/KEY: CDS
(B) LOCATION: 1..2244

(xi) SEQUENCE DESCRIPTION: SEQ ID NO:33:

```
ATGATTGTGC TCGTAACTTG CCTCTTGTTG TTATGTTCAT ACCACACAGT TTTGAGTACA     60

ACAAATAATG AATGCATACA AGTTAACGTA ACACAATTGG CTGGCAATGA AAACCTTATC    120

AGAGATTTTC TGTTTAGTAA CTTTAAAGAA GAAGGAAGTG TAGTTGTTGG TGGTTATTAC    180

CCTACAGAGG TGTGGTACAA CTGCTCTAGA ACAGCTCGAA CTACTGCCTT TCAGTATTTT    240

AATAATATAC ATGCCTTTTA TTTTGTTATG GAAGCCATGG AAAATAGCAC TGGTAATGCA    300

CGTGGTAAAC CATTATTATT TCATGTGCAT GGTGAGCCTG TTAGTGTTAT TATATATATA    360

TCGGCTTATA GGGATGATGT GCAACAAAGG CCCCTTTTAA AACATGGGTT AGTGTGCATA    420

ACTAAAAATC GCCATATTAA CTATGAACAA TTCACCTCCA ACCAGTGGAA TTCCACATGT    480

ACGGGTGCTG ACAGAAAAAT TCCTTTCTCT GTCATACCCA CGGACAATGG AACAAAAATC    540

TATGGTCTTG AGTGGAATGA TGACTTTGTT ACAGCTTATA TTAGTGGTCG TTCTTATCAC    600

TTGAACATCA ATACTAATTG GTTTAACAAT GTCACACTTT TGTATTCACG CTCAAGCACT    660

GCTACCTGGG AATACAGTGC TGCATATGCT TACCAAGGTG TTTCTAACTT CACTTATTAC    720

AAGTTAAATA ACACCAATGG TCTAAAAACC TATGAATTAT GTGAAGATTA TGAACATTGC    780
```

-continued

```
ACTGGCTATG CTACCAATGT ATTTGCTCCG ACATCAGGTG GTTACATACC TGATGGATTT    840

AGTTTTAAYA ATTGGTTCTT GCTTACAAAT AGTTCCACTT TTGTTAGTGG CAGGTTTGTA    900

ACAAATCAAC CATTATTGAT TAATTGCTTG TGGCCAGTGC CCAGTTTTGG TGTAGCAGCA    960

CAAGAATTTT GTTTTGAAGG TGCACAGTTT AGCCAATGTA ATGGTGTGTC TTTAAATAAC   1020

ACAGTGGATG TTATTAGATT CAACCTTAAT TTCACTGCAG ATGTACAATC TGGTATGGGT   1080

GCTACAGTAT TTTCACTGAA TACAACAGGT GGTGTCATTC TTGAAATTTC ATGTTATAGT   1140

GACACAGTGA GTGAGTCTAG TTCTTACAGT TATGGTGAAA TCCCGTTCGG CATAACTGAC   1200

GGACCACGAT ACTGTTATGT ACTTTACAAT GGCACAGCTC TTAAATATTT AGGAACATTA   1260

CCACCCAGTG TAAAGGAAAT TGCTATTAGT AAGTGGGGCC ATTTTTATAT TAATGGTTAC   1320

AATTTCTTTA GCACATTTCC TATTGRTTGT ATATCTTTTA ATTTAACCAC TGGTGTTAGT   1380

GGAGCTTTTT GGACAATTGC TTACACATCG TATACTGAAG CATTAGTACA AGTTGAAAAC   1440

ACAGCTATTA AAAATGTGAC GTATTGTAAC AGTCACATTA ATAACATTAA ATGTTCTCAA   1500

CTTACTGCTA ATTTGAATAA TGGATTTTAT CCTGTTGCTT CAAGTGAAGT AGGTTTCGTT   1560

AATAAGAGTG TTGTGTTATT ACCTAGCTTT TTCACATACA CCGCTGTCAA TATAACCATT   1620

GATCTTGGTA TGAAGCTTAG TGGTTATGGT CAACCCATAG CCTCGACACT AAGTAACATC   1680

ACACTACCAA TGCAGGATAA CAATACTGAT GTGTACTGTA TTCGTTCTAA CCAATTCTCA   1740

GTTTATGTTC ATTCCACTTG CAAAAGTTCT TTATGGGACA ATATTTTTAA TCAAGACTGC   1800

ACGGATGTTT TAGAGGCTAC AGCTGTTATA AAAACTGGTA CTTGTCCTTT CTCATTTGAT   1860

AAATTGAACA ATTACTTGAC TTTTAACAAG TTCTGTTTGT CGTTGAGTCC TGTTGGTGCT   1920

AATTGCAAGT TTGATGTTGC TGCACGTACA AGAACCAATG AGCAGGTTGT TAGAAGTCTA   1980

TATGTAATAT ATGAAGAAGG AGACAACATA GTGGGTGTAC CGTCTGATRA TAGCGGTCTG   2040

CACGATTTGT CTGTGCTACA CCTAGACTCC TGTACAGATT ACAATATATA TGGTAGAACT   2100

GGTGTTGGTA TTATTAGACG AACTAACAGT ACGCTACTTA GTGGCTTATA TTACACATCA   2160

CTATCAGGTG ATTTGTTAGG CTTTAAAAAT GTTAGTGATG GTGTCATTTA TTCTGTGACG   2220

CCATGTGATG TAAGCGCACA AGCGGC                                         2246
```

(2) INFORMATION FOR SEQ ID NO:34:

(i) SEQUENCE CHARACTERISTICS:
(A) LENGTH: 748 amino acids
(B) TYPE: amino acid
(D) TOPOLOGY: unknown (ii) MOLECULE TYPE: peptide (xi) SEQUENCE DESCRIPTION: SEQ ID NO:34:

```
Met Ile Val Leu Val Thr Cys Leu Leu Leu Leu Cys Ser Tyr His Thr
1               5                   10                  15

Val Leu Ser Thr Thr Asn Asn Glu Cys Ile Gln Val Asn Val Thr Gln
            20                  25                  30

Leu Ala Gly Asn Glu Asn Leu Ile Arg Asp Phe Leu Phe Ser Asn Phe
        35                  40                  45

Lys Glu Glu Gly Ser Val Val Val Gly Gly Tyr Tyr Pro Thr Glu Val
    50                  55                  60

Trp Tyr Asn Cys Ser Arg Thr Ala Arg Thr Thr Ala Phe Gln Tyr Phe
65                  70                  75                  80

Asn Asn Ile His Ala Phe Tyr Phe Val Met Glu Ala Met Glu Asn Ser
```

-continued

```
                85                  90                  95

Thr Gly Asn Ala Arg Gly Lys Pro Leu Leu Phe His Val His Gly Glu
            100                 105                 110

Pro Val Ser Val Ile Ile Tyr Ile Ser Ala Tyr Arg Asp Asp Val Gln
        115                 120                 125

Gln Arg Pro Leu Leu Lys His Gly Leu Val Cys Ile Thr Lys Asn Arg
    130                 135                 140

His Ile Asn Tyr Glu Gln Phe Thr Ser Asn Gln Trp Asn Ser Thr Cys
145                 150                 155                 160

Thr Gly Ala Asp Arg Lys Ile Pro Phe Ser Val Ile Pro Thr Asp Asn
                165                 170                 175

Gly Thr Lys Ile Tyr Gly Leu Glu Trp Asn Asp Asp Phe Val Thr Ala
            180                 185                 190

Tyr Ile Ser Gly Arg Ser Tyr His Leu Asn Ile Asn Thr Asn Trp Phe
        195                 200                 205

Asn Asn Val Thr Leu Leu Tyr Ser Arg Ser Ser Thr Ala Thr Trp Glu
    210                 215                 220

Tyr Ser Ala Ala Tyr Ala Tyr Gln Gly Val Ser Asn Phe Thr Tyr Tyr
225                 230                 235                 240

Lys Leu Asn Asn Thr Asn Gly Leu Lys Thr Tyr Glu Leu Cys Glu Asp
                245                 250                 255

Tyr Glu His Cys Thr Gly Tyr Ala Thr Asn Val Phe Ala Pro Thr Ser
            260                 265                 270

Gly Gly Tyr Ile Pro Asp Gly Phe Ser Phe Asn Asn Trp Phe Leu Leu
        275                 280                 285

Thr Asn Ser Ser Thr Phe Val Ser Gly Arg Phe Val Thr Asn Gln Pro
    290                 295                 300

Leu Leu Ile Asn Cys Leu Trp Pro Val Pro Ser Phe Gly Val Ala Ala
305                 310                 315                 320

Gln Glu Phe Cys Phe Glu Gly Ala Gln Phe Ser Gln Cys Asn Gly Val
                325                 330                 335

Ser Leu Asn Asn Thr Val Asp Val Ile Arg Phe Asn Leu Asn Phe Thr
            340                 345                 350

Ala Asp Val Gln Ser Gly Met Gly Ala Thr Val Phe Ser Leu Asn Thr
        355                 360                 365

Thr Gly Gly Val Ile Leu Glu Ile Ser Cys Tyr Ser Asp Thr Val Ser
    370                 375                 380

Glu Ser Ser Ser Tyr Ser Tyr Gly Glu Ile Pro Phe Gly Ile Thr Asp
385                 390                 395                 400

Gly Pro Arg Tyr Cys Tyr Val Leu Tyr Asn Gly Thr Ala Leu Lys Tyr
                405                 410                 415

Leu Gly Thr Leu Pro Pro Ser Val Lys Glu Ile Ala Ile Ser Lys Trp
            420                 425                 430

Gly His Phe Tyr Ile Asn Gly Tyr Asn Phe Phe Ser Thr Phe Pro Ile
        435                 440                 445

Xaa Cys Ile Ser Phe Asn Leu Thr Thr Gly Val Ser Gly Ala Phe Trp
    450                 455                 460

Thr Ile Ala Tyr Thr Ser Tyr Thr Glu Ala Leu Val Gln Val Glu Asn
465                 470                 475                 480

Thr Ala Ile Lys Asn Val Thr Tyr Cys Asn Ser His Ile Asn Asn Ile
                485                 490                 495

Lys Cys Ser Gln Leu Thr Ala Asn Leu Asn Asn Gly Phe Tyr Pro Val
            500                 505                 510
```

-continued

```
Ala Ser Ser Glu Val Gly Phe Val Asn Lys Ser Val Val Leu Leu Pro
        515                 520                 525

Ser Phe Phe Thr Tyr Thr Ala Val Asn Ile Thr Ile Asp Leu Gly Met
    530                 535                 540

Lys Leu Ser Gly Tyr Gly Gln Pro Ile Ala Ser Thr Leu Ser Asn Ile
545                 550                 555                 560

Thr Leu Pro Met Gln Asp Asn Asn Thr Asp Val Tyr Cys Ile Arg Ser
                565                 570                 575

Asn Gln Phe Ser Val Tyr Val His Ser Thr Cys Lys Ser Ser Leu Trp
            580                 585                 590

Asp Asn Ile Phe Asn Gln Asp Cys Thr Asp Val Leu Glu Ala Thr Ala
        595                 600                 605

Val Ile Lys Thr Gly Thr Cys Pro Phe Ser Phe Asp Lys Leu Asn Asn
    610                 615                 620

Tyr Leu Thr Phe Asn Lys Phe Cys Leu Ser Leu Ser Pro Val Gly Ala
625                 630                 635                 640

Asn Cys Lys Phe Asp Val Ala Ala Arg Thr Arg Thr Asn Glu Gln Val
                645                 650                 655

Val Arg Ser Leu Tyr Val Ile Tyr Glu Glu Gly Asp Asn Ile Val Gly
            660                 665                 670

Val Pro Ser Asp Xaa Ser Gly Leu His Asp Leu Ser Val Leu His Leu
        675                 680                 685

Asp Ser Cys Thr Asp Tyr Asn Ile Tyr Gly Arg Thr Gly Val Gly Ile
    690                 695                 700

Ile Arg Arg Thr Asn Ser Thr Leu Leu Ser Gly Leu Tyr Tyr Thr Ser
705                 710                 715                 720

Leu Ser Gly Asp Leu Leu Gly Phe Lys Asn Val Ser Asp Gly Val Ile
                725                 730                 735

Tyr Ser Val Thr Pro Cys Asp Val Ser Ala Gln Ala
            740                 745
```

(2) INFORMATION FOR SEQ ID NO:35:

(i) SEQUENCE CHARACTERISTICS:
(A) LENGTH: 27 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..27

(xi) SEQUENCE DESCRIPTION: SEQ ID NO:35:

```
TCG AGT ACG TCA AAC AAT GAT TGT AGA                                  27
Ser Ser Thr Ser Asn Asn Asp Cys Arg
  1               5
```

(2) INFORMATION FOR SEQ ID NO:36:

(i) SEQUENCE CHARACTERISTICS:
(A) LENGTH: 9 amino acids
(B) TYPE: amino acid
(D) TOPOLOGY: linear (ii) MOLECULE TYPE: protein (xi) SEQUENCE DESCRIPTION: SEQ ID NO:36:

-continued

```
Ser Ser Thr Ser Asn Asn Asp Cys Arg
  1               5


(2) INFORMATION FOR SEQ ID NO:37:

     (i) SEQUENCE CHARACTERISTICS:
          (A) LENGTH: 24 base pairs
          (B) TYPE: nucleic acid
          (C) STRANDEDNESS: double
          (D) TOPOLOGY: unknown

    (ii) MOLECULE TYPE: cDNA

    (ix) FEATURE:
          (A) NAME/KEY: CDS
          (B) LOCATION: 1..24

    (xi) SEQUENCE DESCRIPTION: SEQ ID NO:37:

CAA AGT TTT AAA GAA GAA GGA ATT                                       24
Gln Ser Phe Lys Glu Glu Gly Ile
  1               5


(2) INFORMATION FOR SEQ ID NO:38:

     (i) SEQUENCE CHARACTERISTICS:
          (A) LENGTH: 8 amino acids
          (B) TYPE: amino acid
          (D) TOPOLOGY: linear

    (ii) MOLECULE TYPE: protein

    (xi) SEQUENCE DESCRIPTION: SEQ ID NO:38:

Gln Ser Phe Lys Glu Glu Gly Ile
  1               5


(2) INFORMATION FOR SEQ ID NO:39:

     (i) SEQUENCE CHARACTERISTICS:
          (A) LENGTH: 18 base pairs
          (B) TYPE: nucleic acid
          (C) STRANDEDNESS: double
          (D) TOPOLOGY: unknown

    (ii) MOLECULE TYPE: cDNA

    (ix) FEATURE:
          (A) NAME/KEY: CDS
          (B) LOCATION: 1..18

    (xi) SEQUENCE DESCRIPTION: SEQ ID NO:39:

GCA ACT ACC ACT GCC TAT                                               18
Ala Thr Thr Thr Ala Tyr
  1               5


(2) INFORMATION FOR SEQ ID NO:40:

     (i) SEQUENCE CHARACTERISTICS:
          (A) LENGTH: 6 amino acids
          (B) TYPE: amino acid
          (D) TOPOLOGY: linear

    (ii) MOLECULE TYPE: protein

    (xi) SEQUENCE DESCRIPTION: SEQ ID NO:40:

Ala Thr Thr Thr Ala Tyr
  1               5


(2) INFORMATION FOR SEQ ID NO:41:

     (i) SEQUENCE CHARACTERISTICS:
```

-continued (A) LENGTH: 150 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..150

(xi) SEQUENCE DESCRIPTION: SEQ ID NO:41:

```
GGG GAT GAT GTG CAA CAA AGG CCA CTT TTA GAA CAT GGG TTA TTG TGC       48
Gly Asp Asp Val Gln Gln Arg Pro Leu Leu Glu His Gly Leu Leu Cys
  1               5                  10                  15

ATT ACT AAA AAT CGC AAT ATT GAC TAT AAC ACC TTC ACC AGC AAC CAG       96
Ile Thr Lys Asn Arg Asn Ile Asp Tyr Asn Thr Phe Thr Ser Asn Gln
             20                  25                  30

TGG GAT TCC ATA TGT ACG GGT AAT GAC AGA AAA ATT CCT TTC TCT GTC      144
Trp Asp Ser Ile Cys Thr Gly Asn Asp Arg Lys Ile Pro Phe Ser Val
         35                  40                  45

ATA CCC                                                              150
Ile Pro
     50
```

(2) INFORMATION FOR SEQ ID NO:42:

(i) SEQUENCE CHARACTERISTICS:
(A) LENGTH: 50 amino acids
(B) TYPE: amino acid
(D) TOPOLOGY: linear (ii) MOLECULE TYPE: protein (xi) SEQUENCE DESCRIPTION: SEQ ID NO:42:

```
Gly Asp Asp Val Gln Gln Arg Pro Leu Leu Glu His Gly Leu Leu Cys
  1               5                  10                  15

Ile Thr Lys Asn Arg Asn Ile Asp Tyr Asn Thr Phe Thr Ser Asn Gln
             20                  25                  30

Trp Asp Ser Ile Cys Thr Gly Asn Asp Arg Lys Ile Pro Phe Ser Val
         35                  40                  45

Ile Pro
     50
```

(2) INFORMATION FOR SEQ ID NO:43:

(i) SEQUENCE CHARACTERISTICS:
(A) LENGTH: 18 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..18

(xi) SEQUENCE DESCRIPTION: SEQ ID NO:43:

```
AAT ATT GAC TAT AAC ACC                                               18
Asn Ile Asp Tyr Asn Thr
  1               5
```

(2) INFORMATION FOR SEQ ID NO:44:

(i) SEQUENCE CHARACTERISTICS:
(A) LENGTH: 6 amino acids

-continued (B) TYPE: amino acid
(D) TOPOLOGY: linear (ii) MOLECULE TYPE: protein (xi) SEQUENCE DESCRIPTION: SEQ ID NO:44:

```
Asn Ile Asp Tyr Asn Thr
  1               5
```

(2) INFORMATION FOR SEQ ID NO:45:

(i) SEQUENCE CHARACTERISTICS:
(A) LENGTH: 66 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..66

(xi) SEQUENCE DESCRIPTION: SEQ ID NO:45:

```
TTG TGC ATT ACT AAA AAT CGC AAT ATT GAC TAT AAC ACC TTC ACC AGC       48
Leu Cys Ile Thr Lys Asn Arg Asn Ile Asp Tyr Asn Thr Phe Thr Ser
  1               5                  10                  15

AAC CAG TGG GAT TCC ATA                                               66
Asn Gln Trp Asp Ser Ile
             20
```

(2) INFORMATION FOR SEQ ID NO:46:

(i) SEQUENCE CHARACTERISTICS:
(A) LENGTH: 22 amino acids
(B) TYPE: amino acid
(D) TOPOLOGY: linear (ii) MOLECULE TYPE: protein (xi) SEQUENCE DESCRIPTION: SEQ ID NO:46:

```
Leu Cys Ile Thr Lys Asn Arg Asn Ile Asp Tyr Asn Thr Phe Thr Ser
  1               5                  10                  15

Asn Gln Trp Asp Ser Ile
             20
```

(2) INFORMATION FOR SEQ ID NO:47:

(i) SEQUENCE CHARACTERISTICS:
(A) LENGTH: 24 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..24

(xi) SEQUENCE DESCRIPTION: SEQ ID NO:47:

```
AAT CGC AAT ATT GAC TAT AAC ACC                                       24
Asn Arg Asn Ile Asp Tyr Asn Thr
  1               5
```

(2) INFORMATION FOR SEQ ID NO:48:

(i) SEQUENCE CHARACTERISTICS:
(A) LENGTH: 8 amino acids

-continued (B) TYPE: amino acid
(D) TOPOLOGY: linear (ii) MOLECULE TYPE: protein (xi) SEQUENCE DESCRIPTION: SEQ ID NO:48:

```
Asn Arg Asn Ile Asp Tyr Asn Thr
  1               5
```

(2) INFORMATION FOR SEQ ID NO:49:

(i) SEQUENCE CHARACTERISTICS:
(A) LENGTH: 18 base pairs
(B) TYPE: nucleic acid
(C) STRANDEDNESS: double
(D) TOPOLOGY: unknown (ii) MOLECULE TYPE: cDNA (ix) FEATURE:
(A) NAME/KEY: CDS
(B) LOCATION: 1..18

(xi) SEQUENCE DESCRIPTION: SEQ ID NO:49:

```
AAT TGG AAC ATC AAT AAT                                         18
Asn Trp Asn Ile Asn Asn
  1               5
```

(2) INFORMATION FOR SEQ ID NO:50:

(i) SEQUENCE CHARACTERISTICS:
(A) LENGTH: 6 amino acids
(B) TYPE: amino acid
(D) TOPOLOGY: linear (ii) MOLECULE TYPE: protein (xi) SEQUENCE DESCRIPTION: SEQ ID NO:50:

```
Asn Trp Asn Ile Asn Asn
  1               5
```

(2) INFORMATION FOR SEQ ID NO:51:

(i) SEQUENCE CHARACTERISTICS:
(A) LENGTH: 24 base pairs
(B) TYPE: nucleic acid
(C) STRANDEDNESS: unknown
(D) TOPOLOGY: unknown (ii) MOLECULE TYPE: cDNA (ix) FEATURE:
(A) NAME/KEY: CDS
(B) LOCATION: 1..24

(xi) SEQUENCE DESCRIPTION: SEQ ID NO:51:

```
ATC TTT TTC GCA CAT ACC GCT ATC                                 24
Ile Phe Phe Ala His Thr Ala Ile
  1               5
```

(2) INFORMATION FOR SEQ ID NO:52:

(i) SEQUENCE CHARACTERISTICS:
(A) LENGTH: 8 amino acids
(B) TYPE: amino acid
(D) TOPOLOGY: linear (ii) MOLECULE TYPE: protein (xi) SEQUENCE DESCRIPTION: SEQ ID NO:52:

-continued

```
Ile Phe Phe Ala His Thr Ala Ile
  1               5


(2) INFORMATION FOR SEQ ID NO:53:

     (i) SEQUENCE CHARACTERISTICS:
          (A) LENGTH: 377 base pairs
          (B) TYPE: nucleic acid
          (C) STRANDEDNESS: double
          (D) TOPOLOGY: unknown

    (ii) MOLECULE TYPE: cDNA

    (ix) FEATURE:
          (A) NAME/KEY: CDS
          (B) LOCATION: 1..375

    (xi) SEQUENCE DESCRIPTION: SEQ ID NO:53:

AAT GCT CGT GGT AAA CCA TTA TTA TTT CAT GTG CAT GGT GAG CCT GTT        48
Asn Ala Arg Gly Lys Pro Leu Leu Phe His Val His Gly Glu Pro Val
  1               5                  10                  15

AGT GTT ATT ATA TAT ATA TCG GCT TAT AGG GAT GAT GTG CAA CAA AGG        96
Ser Val Ile Ile Tyr Ile Ser Ala Tyr Arg Asp Asp Val Gln Gln Arg
             20                  25                  30

CCC CTT TTA AAA CAT GGG TTA GTG TGC ATA ACT AAA AAT CGC CAT ATT       144
Pro Leu Leu Lys His Gly Leu Val Cys Ile Thr Lys Asn Arg His Ile
         35                  40                  45

AAC TAT GAA CAA TTC ACC TCC AAC CAG TGG AAT TCC ACA TGT ACG GGT       192
Asn Tyr Glu Gln Phe Thr Ser Asn Gln Trp Asn Ser Thr Cys Thr Gly
     50                  55                  60

GCT GAC AGA AAA ATT CCT TTC TCT GTC ATA CCC ACG GAC AAT GGA ACA       240
Ala Asp Arg Lys Ile Pro Phe Ser Val Ile Pro Thr Asp Asn Gly Thr
 65                  70                  75                  80

AAA ATC TAT GGT CTT GAG TGG AAT GAT GAC TTT GTT ACA GCT TAT ATT       288
Lys Ile Tyr Gly Leu Glu Trp Asn Asp Asp Phe Val Thr Ala Tyr Ile
                 85                  90                  95

AGT GGT CGT TCT TAT CAC TTG AAC ATC AAT ACT AAT TGG TTT AAC AAT       336
Ser Gly Arg Ser Tyr His Leu Asn Ile Asn Thr Asn Trp Phe Asn Asn
            100                 105                 110

GTC ACA CTT TTG TAT TCA CGC TCA AGC ACT GCT ACC TGG GA                377
Val Thr Leu Leu Tyr Ser Arg Ser Ser Thr Ala Thr Trp
        115                 120                 125


(2) INFORMATION FOR SEQ ID NO:54:

     (i) SEQUENCE CHARACTERISTICS:
          (A) LENGTH: 125 amino acids
          (B) TYPE: amino acid
          (D) TOPOLOGY: linear

    (ii) MOLECULE TYPE: protein

    (xi) SEQUENCE DESCRIPTION: SEQ ID NO:54:

Asn Ala Arg Gly Lys Pro Leu Leu Phe His Val His Gly Glu Pro Val
  1               5                  10                  15

Ser Val Ile Ile Tyr Ile Ser Ala Tyr Arg Asp Asp Val Gln Gln Arg
             20                  25                  30

Pro Leu Leu Lys His Gly Leu Val Cys Ile Thr Lys Asn Arg His Ile
         35                  40                  45

Asn Tyr Glu Gln Phe Thr Ser Asn Gln Trp Asn Ser Thr Cys Thr Gly
     50                  55                  60

Ala Asp Arg Lys Ile Pro Phe Ser Val Ile Pro Thr Asp Asn Gly Thr
 65                  70                  75                  80
```

-continued

```
Lys Ile Tyr Gly Leu Glu Trp Asn Asp Asp Phe Val Thr Ala Tyr Ile
                85                  90                  95

Ser Gly Arg Ser Tyr His Leu Asn Ile Asn Thr Asn Trp Phe Asn Asn
            100                 105                 110

Val Thr Leu Leu Tyr Ser Arg Ser Ser Thr Ala Thr Trp
        115                 120                 125
```